(12) United States Patent
Hsin et al.

(10) Patent No.: US 11,505,529 B2
(45) Date of Patent: Nov. 22, 2022

(54) 8-PHENYL-ISOQUINOLINES AND PHARMACEUTICAL COMPOSITION THEREOF USED IN THE TREATMENT OF IRRITABLE BOWEL SYNDROME

(71) Applicant: Linda Chia-Hui Yu, Taipei (TW)

(72) Inventors: Ling-Wei Hsin, Taipei (TW); Linda Chia-Hui Yu, Taipei (TW); Tsung-Chun Lee, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 612 days.

(21) Appl. No.: 16/490,070

(22) PCT Filed: Mar. 2, 2018

(86) PCT No.: PCT/CA2018/000043
§ 371 (c)(1),
(2) Date: Aug. 29, 2019

(87) PCT Pub. No.: WO2018/157233
PCT Pub. Date: Sep. 7, 2018

(65) Prior Publication Data
US 2020/0071274 A1 Mar. 5, 2020

Related U.S. Application Data

(60) Provisional application No. 62/466,370, filed on Mar. 3, 2017.

(51) Int. Cl.
*C07D 217/04* (2006.01)
*A61P 1/00* (2006.01)
*C07D 401/06* (2006.01)

(52) U.S. Cl.
CPC .......... *C07D 217/04* (2013.01); *A61P 1/00* (2018.01); *C07D 401/06* (2013.01)

(58) Field of Classification Search
CPC ........ C07D 271/04; C07D 401/06; A61P 1/00
See application file for complete search history.

(56) References Cited

U.S. PATENT DOCUMENTS 8,552,028 B2 * 10/2013 Su .................. C07D 217/04
514/307

* cited by examiner

*Primary Examiner* — Timothy R Rozof
(74) *Attorney, Agent, or Firm* — Hannah M. Tien

(57) ABSTRACT

A series of 8-phenyl-isoquinoline derivatives (I) exhibit high binding affinity to 5-HT$_7$ receptor (5-HT$_7$R) and demonstrate potent antinociceptive activity in two animal models for Irritable Bowel Syndrome (IBS) by intraperitoneal injection (i.p.) or by oral administration (p.o.). These 5-HT$_7$ receptor antagonists are a new class of therapeutic agents for the treatment of IBS.

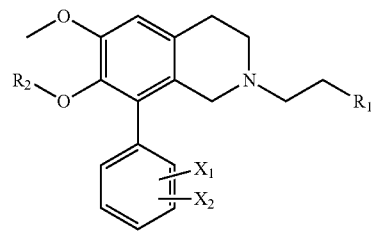

8 Claims, 12 Drawing Sheets

Fig. 5
Fig. 5(A)
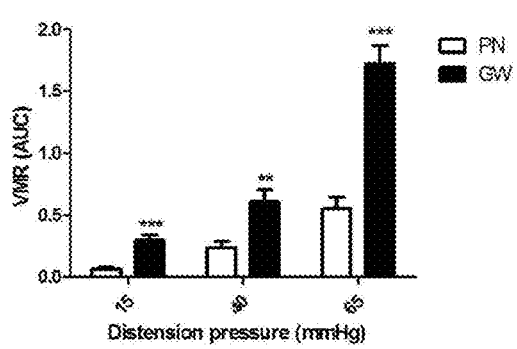
Fig. 5(B)
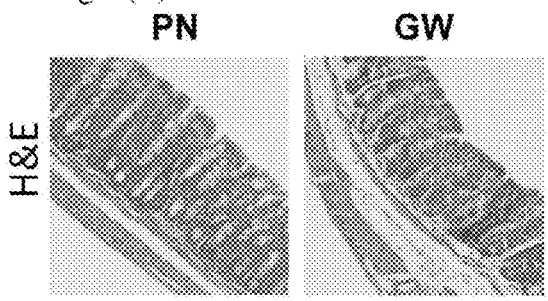
Fig. 5(C)
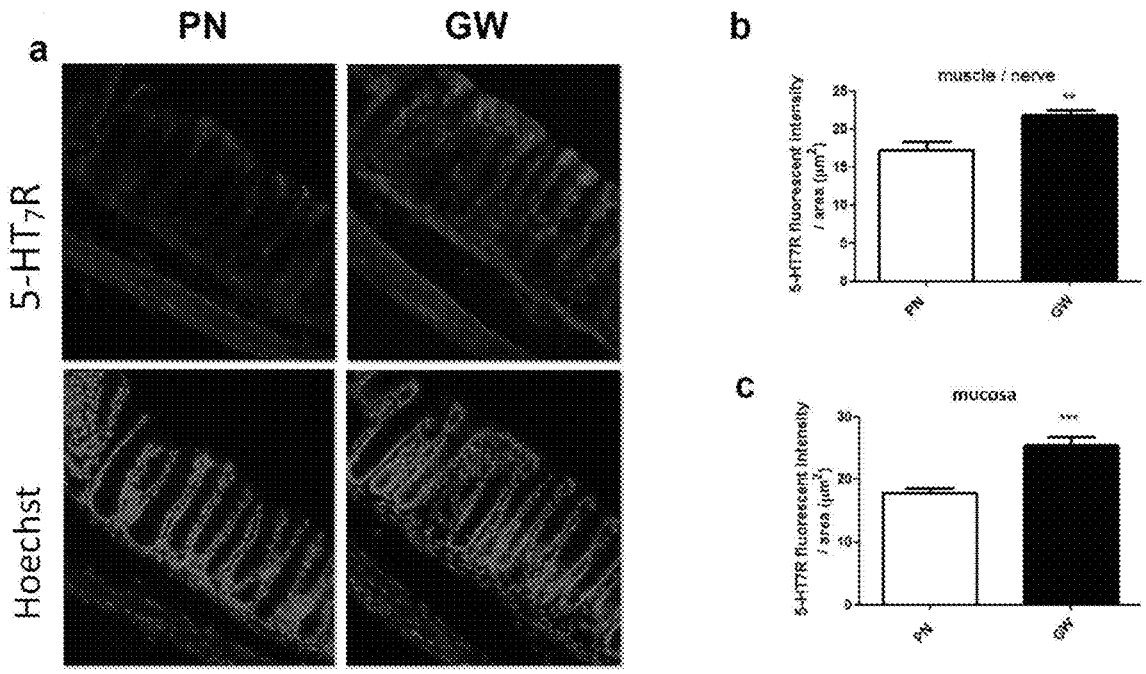
Fig. 5(D)
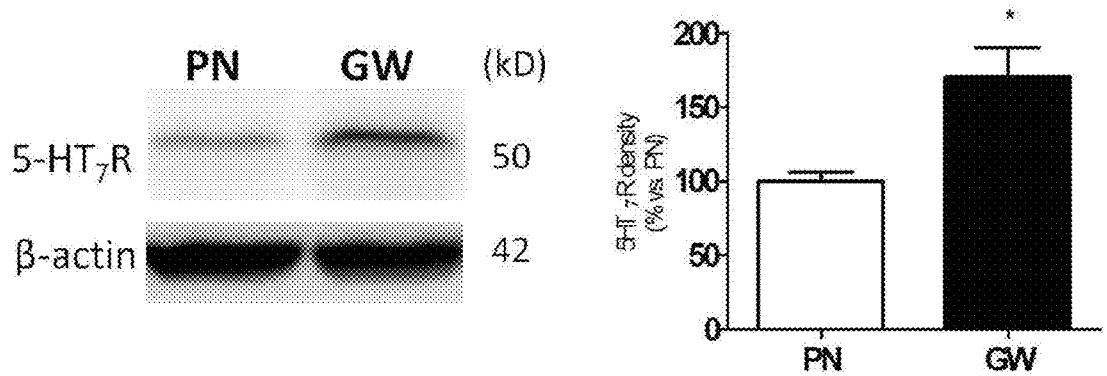

Fig. 6
Fig. 6(A)
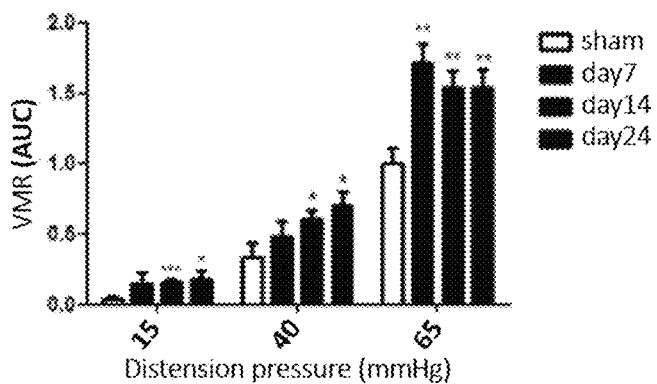
Fig. 6(B)
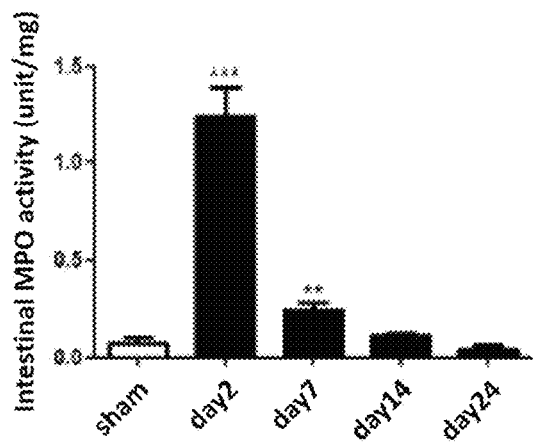
Fig. 6(C)
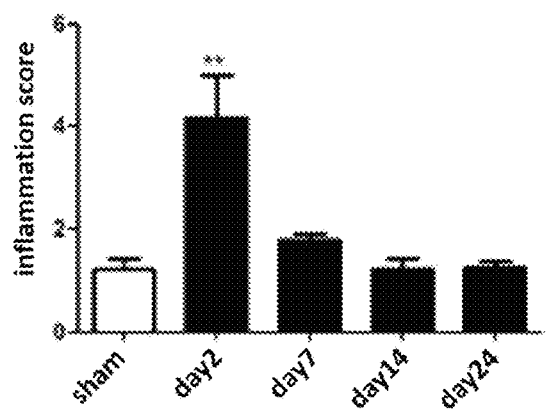

Fig. 9
Fig. 9(A)
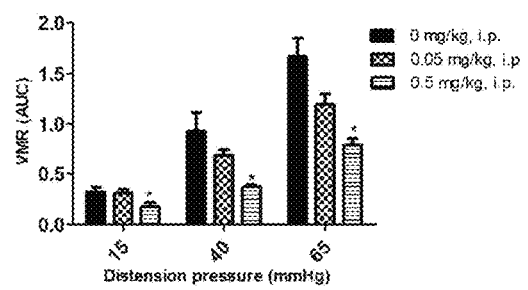
Fig. 9(B)
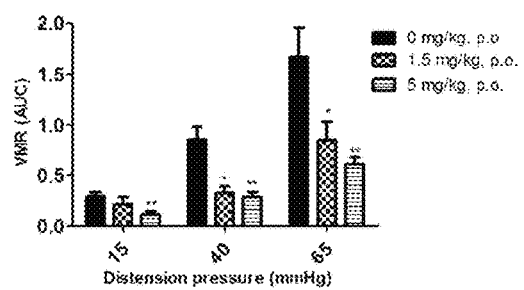
Fig. 9(C)
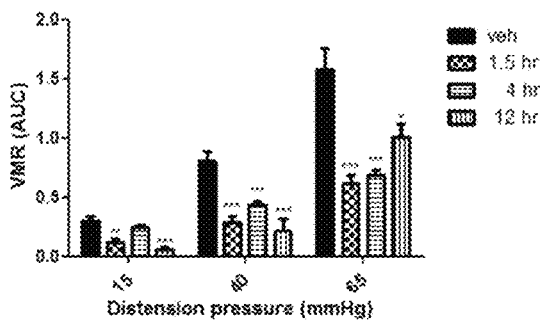
Fig. 9(D)
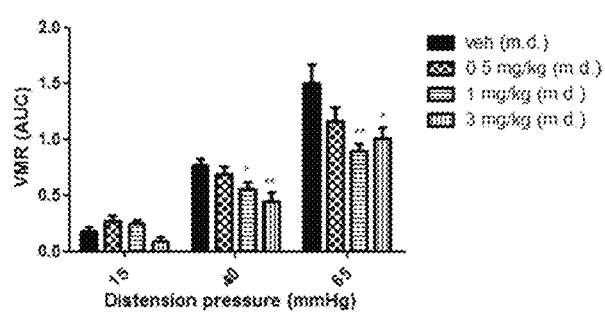

Fig. 10(A) TNBS mice

Fig. 11(A) GW Mice

Fig. 11(B) TNBS Mice

8-PHENYL-ISOQUINOLINES AND PHARMACEUTICAL COMPOSITION THEREOF USED IN THE TREATMENT OF IRRITABLE BOWEL SYNDROME

CROSS-REFERENCES TO RELATED APPLICATIONS

This patent application is a U.S. National Stage Application of PCT/CA2018/000043 filed Mar. 2, 2018 and claims the benefit of priority from U.S. Provisional Application Ser. No. 62/466,370, filed Mar. 3, 2017, the contents of each of which is incorporated herein by reference in their entirety.

FIELD OF THE INVENTION

The present invention relates to a series of 8-phenylisoquinoline derivatives used in the treatment of irritable bowel syndrome (IBS).

BACKGROUND OF THE INVENTION

The 5-$HT_7$ receptor (5-$HT_7$R) is the latest member among the 14 subtypes in 5-HT receptor family. It is widely distributed in both central nervous system (CNS) (most abundant in hypothalamus, thalamus, hippocampus, and cortex) and peripheral organs (e.g. spleen, kidney, intestine, heart and coronary artery), which implicates its role in various physiological functions and pathologic processes. 5-$HT_7$R is positively coupled to adenylate cyclase and has a low sequence homology with other 5-HT receptor subtypes (less than 40%). Based on the studies conducted by using selective 5-$HT_7$R ligands and knock-out mice models, 5-$HT_7$R is involved in circadian rhythm regulation, thermoregulation, sleep disorders, mood disorders, pain, learning and memory. Therefore, the 5-$HT_7$R ligands are potential therapeutic agents for the treatment of a variety of 5-$HT_7$R-related diseases and disorders. The 5-$HT_7$R antagonists may be effective treatment of depression, anxiety, schizophrenia, and dementia, whereas the 5-$HT_7$R agonists could be potential treatment for pain and symptoms of pain (especially neuropathic pain and inflammatory pain).

In addition, 5-$HT_7$R is also a potential drug target for migraine (WO2009029439 A1), hypertention, various mucosal inflammation (WO2012058769 A1), such as irritable bowel syndrome, and urinary incontinence, through its effective smooth muscle relaxation of central and peripheral blood vessels and intestinal, colon, and bladder tissues, respectively. Several therapeutic agents, such as tricyclic antidepressants, typical and atypical antipsychotics and some 5-$HT_2$ receptor antagonists, were found to display moderate to high affinity for 5-$HT_7$R.

In consideration of the versatile therapeutic potential of 5-$HT_7$R ligands, numerous efforts have been focused on the discovery and development of selective 5-$HT_7$R agonists and antagonists. Different structural classes of 5-$HT_7$R ligands have been reported, including 5-$HT_7$R agonists, such as AS-19, LP-44, LP-12, LP-211, and E-55888, and 5-$HT_7$R antagonists, such as SB-258719, SB-269970, SB-656104, DR-4004 and JNJ-18038683. Despite of the numerous efforts, there is no 5-$HT_7$R ligand has been used in clinic and still a need to discover and develop novel 5-$HT_7$R ligands with desirable physicochemical and pharmacokinetic properties as potential therapeutic agents for the treatment of 5-$HT_7$R-related diseases and disorders.

Irritable bowel syndrome (IBS) is mainly characterized by recurrent abdominal pain associated with bowel habit changes, in the absence of identifiable organic cause or macroscopic lesions. IBS represents a substantial clinical problem that accounts for 10-40% of gastroenterology outpatients in Asian and Western countries. Severe abdominal pain is the clinical hallmark of IBS, the most likely symptom to result in medical consultation. Subtypes of IBS include diarrhea-predominant IBS-D, constipation predominant IBS-C, or alternating IBS-A. The development of IBS disorder is believed to be related to a disturbed brain-gut axis; however, the pathogenesis is still poorly understood.

Altered intestinal serotonin (5-HT) level in patients is a validated biomarker for IBS. However, clinical drugs targeting 5-HT receptors for IBS treatment are limited nowadays and prescribed only under emergency investigational drug protocol. Alosetron, a 5-$HT_3$R antagonist for treatment of IBS-D, had been withdrawn by FDA for severe side effects (e.g. ischemic colitis, cerebrovascular or cardiovascular ischemia), and reintroduced later for women only with severe symptoms. Other available symptom-relieving agents (e.g. antispasmodics, antidiarrheals, osmotics, sedatives, antidepressants etc.) are not globally effectively for patients. Medical research for IBS pathogenesis relies heavily on analysis of patient biopsy samples. Animal models with visceral hypersensitivity have been established, albeit each with weaknesses and strengths regarding its translational value to IBS. As such, progress in therapeutic development for IBS has been hindered. To date, development of novel targeted drugs for clinical management of IBS is much in need.

Diverse risk factors, including psychological stress, intestinal infection, immune and inflammatory responses, genetic predisposition, and changes in the gut microbiota, have been found to contribute to the development of IBS symptoms. A high rate of IBS patients reported past traumatic events in childhood or adulthood. IBS symptoms may begin after a bout of infectious gastroenteritis, termed post-infectious (PI)-IBS. Follow-up studies of a waterborne giardiasis outbreak in Norway reported that more than 40% of patients experience IBS-like symptoms lasting for three years after acute *Giardia* lamblia infection. The post-infective symptom exacerbation was correlated with the experience of physical or mental stress. Experimental models of post-clearance of pathogen infection and post-resolution of chemical-induced enterocolitis exhibited intestinal hyperalgesia. Moreover, animals subjected to psychological stress also showed visceral hypersensitivity to colorectal distension. Two mouse models with IBS-like visceral hypersensitivity, including dual challenge with *Giardia* postinfection combined with psychological stress and post-resolution of trinitrobenzene sulfonic acid (TNBS)-induced colitis were used for testing of the analgesic effects of novel 5-$HT_7$R ligands.

Among the receptor subtypes, 5-$HT_7$R is the most recently discovered family member with unknown pathophysiological role. Stimulation of 5-$HT_7$R induces exaggerated relaxation of circular smooth muscle, which has been implicated in ineffective gas propulsion and abdominal bloating. Expression of 5-$HT_7$R has been identified in the enteric neurons (i.e. myenteric afferent neurons and mucosal nerve fibers), smooth muscles, and dendritic cells in the colon, as well as lumbar dorsal root ganglions and brain. The present invention proves a series of 8-phenylisoquinoline derivatives, on alleviation of intestinal pain in two animal models of IBS.

SUMMARY OF THE INVENTION

The present invention relates to a novel compound of the following general formula or a pharmaceutically acceptable salt thereof:

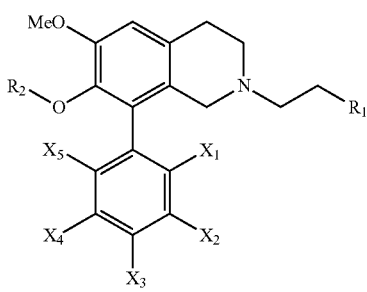

wherein $R_1$ is selected from a group consisting of hydrogen, a $C_{1-10}$ linear chain alkyl group, a $C_{1-10}$ branched chain alkyl group, a $(CH_2)_n(Hete)R_{10}R_{11}R_{12}$ and a $(CH_2)_nArR_{10}R_{11}R_{12}$, wherein the n is an integer from 0 to 6, Hete is a heteroaromatic group, Ar is an aromatic group, and $R_{10}$, $R_{11}$ and $R_{12}$ are independently selected from a group consisting of hydrogen, halo group, a nitro group, an amino group, a cyano group, an acetyl group, a $C_{1-6}$ linear chain saturated alkyl group, a $C_{1-6}$ linear chain saturated alkoxy group and a $C_{1-6}$ linear chain saturated haloalkyl group;

$R_2$ is a hydrogen or a $C_{1-6}$ linear chain saturated alkyl group; and $X_1$, $X_2$, $X_3$, $X_4$ and $X_5$ are independently selected from a group consisting of hydrogen, a halo group, a nitro group, an amino group, a cyano group, an acetyl group, a $C_{1-6}$ linear chain saturated alkyl group, a $C_{1-6}$ branched chain saturated alkyl group, a $C_{1-6}$ linear chain saturated alkoxy group, a $C_{1-6}$ branched chain saturated alkoxy group, a $C_{1-6}$ linear chain saturated alkylthio group, a $C_{1-6}$ branched chain saturated alkylthio group, a $C_{1-6}$ linear chain saturated haloalkyl group and a $C_{1-6}$ branched chain saturated haloalkyl group.

The present invention also relates to a pharmaceutical composition comprising a pharmaceutically acceptable carrier and a therapeutically effective amount of this novel compound or a pharmaceutically acceptable salt thereof. Further, the present invention relates to a method of using the aforementioned pharmaceutical composition in the treatment of irritable bowel syndrome.

BRIEF DESCRIPTION OF THE DRAWINGS

FIG. 5 shows the visceral hypersensitivity observed in an IBS-like mouse model by dual challenge of *Giardia* combined with stress. FIG. 5(A) The visceromoter response (VMR) to colorectal distension was expressed as area under curve (AUC) and determined in each mouse as an indicator of intestinal pain. FIG. 5(B) Representative images of colon histology in PN and GW mice. FIG. 5(C) Representative images of immunostained 5-HT$_7$R in colonic tissues of PN and GW mice (panel a) and quantification of 5-HT$_7$R immunoreactivity in muscle/nerve and mucosal layers (panel b and c). FIG. 5(D) The results of Western blotting showing increased 5-HT$_7$R protein levels in GW mice.

FIG. 9 shows dose and time response of compound 8 in intestinal pain of GW mice. FIG. 9(A) Compound 8 was i.p. administered at various doses 90 minutes before pain analysis. FIG. 9(B) Compound 8 was p.o. administered at various doses 90 minutes before pain analysis. FIG. 9(C) Compound 8 (5 mg/Kg) was p.o. administered at 1.5, 4 or 12 hours before pain analysis. FIG. 9(D) Compound 8 (3 mg/Kg) was repeatedly administered p.o. over a course of 10 days as multiple doses (m.d.) before pain analysis.

FIG. 11(A) Intestinal pain levels in GW mice. FIG. 11(B) Intestinal pain levels in TNBS mice.

DETAILED DESCRIPTION OF THE INVENTION

Figure 1:
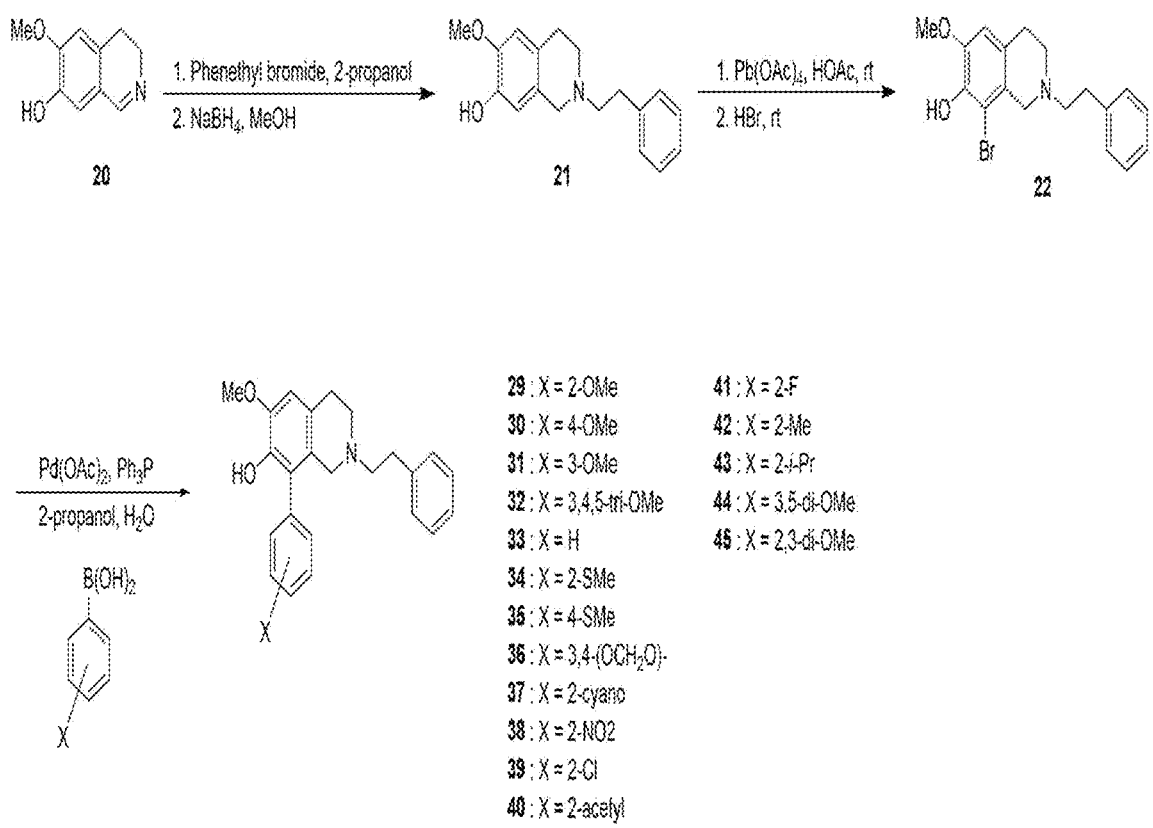
FIG. 1 shows the synthetic scheme 1 of novel derivatives of 8-phenylisoquinoline.

The present invention provides a novel compound of the following general formula or a pharmaceutically acceptable salt thereof:

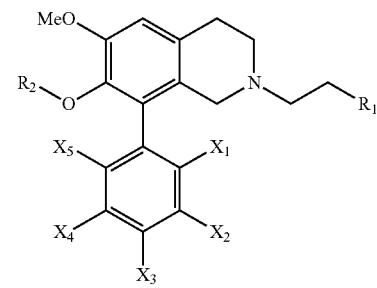

wherein $R_1$ is selected from a group consisting of hydrogen, a $C_{1-10}$ linear chain alkyl group, a $C_{1-10}$ branched chain alkyl group, a $(CH_2)_n(Hete)R_{10}R_{11}R_{12}$ and a $(CH_2)_nArR_{10}R_{11}R_{12}$, wherein n is an integer from 0 to 6, Hete is a heteroaromatic group, Ar is an aromatic group, and $R_{10}$, $R_{11}$ and $R_{12}$ are independently selected from a group consisting of hydrogen, a halo group, a nitro group, an amino group, a cyano group, an acetyl group, a $C_{1-6}$ linear chain saturated alkyl group, a $C_{1-6}$ linear chain saturated alkoxy group and a $C_{1-6}$ linear chain saturated haloalkyl group;

$R_2$ is a hydrogen or a $C_{1-6}$ linear chain saturated alkyl group; and $X_1$, $X_2$, $X_3$, $X_4$ and $X_5$ are independently selected from a group consisting of hydrogen, a halo group, a nitro group, an amino group, a cyano group, an acetyl group, a $C_{1-6}$ linear chain saturated alkyl group, a $C_{1-6}$ branched chain saturated alkyl group, a $C_{1-6}$ linear chain saturated alkoxy group, a $C_{1-6}$ branched chain saturated alkoxy group, a $C_{1-6}$ linear chain saturated alkylthio group, a $C_{1-6}$ branched chain saturated alkylthio group, a $C_{1-6}$ linear chain saturated haloalkyl group and a $C_{1-6}$ branched chain saturated haloalkyl group.

In one embodiment of the present invention, the halo group of the novel compound is selected from a group consisting of fluorine, chlorine, bromine and iodine. In another embodiment of the present invention, the heteroaromatic group of the novel compound is selected from a group consisting of a pyrrolyl group, a furanyl group, a thiophenyl group, a pyridinyl group, a pyrimidinyl group, a thiazolyl group, an indolyl group, an isoindolyl group, an indazolyl group, a benzofuranyl group, an isobenzofuranyl group, a benzothiophenyl group, a benzimidazolyl group, a benzoxazolyl group and a benzothiazolyl group.

In a preferred embodiment of the present invention, the novel compound is one selected from 6-methoxy-8-(2-methoxyphenyl)-2-(3-(4-nitrophenyl)propyl)-1,2,3,4-tetrahydroisoquinolin-7-ol (compound 7), 6-methoxy-8-(2-methoxyphenyl)-2-(3-(pyridin-4-yl)propyl)-1,2,3,4-tetrahydroisoquinolin-7-ol (compound 8), 6-methoxy-8-(2-methoxyphenyl)-2-(3-(pyridin-3-yl)propyl)-1,2,3,4-tetrahydroisoquinolin-7-ol (compound 9), and 6,7-dimethoxy-8-(2-methoxyphenyl)-2-(3-(pyridin-4-yl)propyl)-1,2,3,4-tetrahydroisoquinoline (compound 10), or a pharmaceutically acceptable salt. In a more preferred embodiment of the present invention, the novel compound is 6-methoxy-8-(2-methoxyphenyl)-2-(3-(pyridin-4-yl)propyl)-1,2,3,4-tetrahydroisoquinolin-7-ol (compound 8) or a pharmaceutically acceptable salt.

The present invention further provides a pharmaceutical composition comprising: a pharmaceutically acceptable carrier, and a therapeutically effective amount of a novel compound of the following general formula:

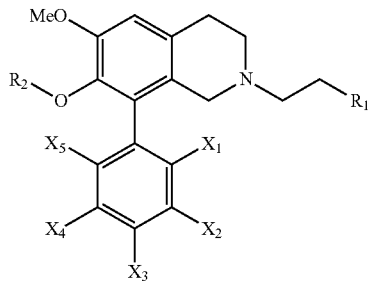

wherein $R_1$ is selected from a group consisting of hydrogen, a $C_{1-10}$ linear chain alkyl group, a $C_{1-10}$ branched chain alkyl group, $(CH_2)_n(Hete)R_{10}R_{11}R_{12}$ and $(CH_2)_nArR_{10}R_{11}R_{12}$, wherein n is an integer from 0 to 6, Hete is a heteroaromatic group, Ar is an aromatic group, and $R_{10}$, $R_{11}$ and $R_{12}$ are independently selected from a group consisting of hydrogen, a halo group, a nitro group, an amino group, a cyano group, an acetyl group, a $C_{1-6}$ linear chain saturated alkyl group, a $C_{1-6}$ linear chain saturated alkoxy group and a $C_{1-6}$ linear chain saturated haloalkyl group;

$R_2$ is a hydrogen or a $C_{1-6}$ linear chain saturated alkyl group; and $X_1$, $X_2$, $X_3$, $X_4$ and $X_5$ are independently selected from a group consisting of hydrogen, a halo group, a nitro group, an amino group, a cyano group, an acetyl group, a $C_{1-6}$ linear chain saturated alkyl group, a $C_{1-6}$ branched chain saturated alkyl group, a $C_{1-6}$ linear chain saturated alkoxy group, a $C_{1-6}$ branched chain saturated alkoxy group, a $C_{1-6}$ linear chain saturated alkylthio group, a $C_{1-6}$ branched chain saturated alkylthio group, a $C_{1-6}$ linear chain saturated haloalkyl group and a $C_{1-6}$ branched chain saturated haloalkyl group.

In one embodiment of the present invention, the halo group of the novel compound of the pharmaceutical composition is selected from a group consisting of fluorine, chlorine, bromine and iodine. In another embodiment of the present invention, the heteroaromatic group of the novel compound of the pharmaceutical composition is selected from a group consisting of a pyrrolyl group, a furanyl group, a thiophenyl group, a pyridinyl group, a pyrimidinyl group, a thiazolyl group, an indolyl group, an isoindolyl group, an indazolyl group, a benzofuranyl group, an isobenzofuranyl group, a benzothiophenyl group, a benzimidazolyl group, a benzoxazolyl group and a benzothiazolyl group.

In a preferred embodiment of the present invention, comprising: a pharmaceutically acceptable carrier, and a therapeutically effective amount of 6-methoxy-8-(2-methoxyphenyl)-2-(3-(pyridin-4-yl)propyl)-1,2,3,4-tetrahydroisoquinolin-7-ol (compound 8) or a pharmaceutically acceptable salt thereof.

The "pharmaceutically acceptable carrier" or "excipient" or "pharmaceutically acceptable carrier or excipient" or "bioavailable carrier" or "bioavailable carrier or excipient" includes but not limited to a solvent, a dispersant, a coating, an antimicrobial agent, an antifungal agent to preserve or a delay-absorbed agent and any other known compound to prepare formulation. In general, these carriers or excipients themselves do not have activity of treating disease. Pharmaceutical compositions or formulations prepared by using the novel compound or its derivatives disclosed in the present invention in combination with a pharmaceutically acceptable carrier or excipient do not cause adverse effect, allergy or other inappropriate reaction of animals or humans. Therefore, the novel compound or its derivatives disclosed in the present invention in combination with a pharmaceutically acceptable carrier or excipient can be applied to human clinically. The pharmaceutical compositions or formulations comprising the novel compound or its derivatives of the present invention can achieve therapeutic effect through intravenous injection, oral administration, inhalation or through local administration of nose, rectum, vagina or hypoglottis. In one embodiment, 0.1 mg to 100 mg of the active ingredient of the compound per day is administered to patients having different diseases.

The carrier to be used is different depending on the pharmaceutical composition or formulation to be prepared. The composition for sterile injection can be suspended in sterile intravenous injection diluents or solvents, such as 1,3-butanediol. The acceptable carrier could be mannitol or water. In addition, the oil fixed or synthesized monoglyceride/diglyceride suspension medium are commonly used solvents. Fatty acids, such as oleic acid, olive oil, castor oil, glyceride derivatives, especially the polyoxyethylenated form could be prepared for injection and natural pharmaceutically acceptable oil. These oil solutions or suspensions include long-chain alcohol diluents, dispersant, carboxymethyl cellulose or similar dispersant. Other surfactants for common use include Tween, Spans, other similar emulsifier, pharmaceutically acceptable solid for pharmaceutical manufacture industry, liquid, or other bioavailable enhancer for formulation development.

The composition for oral administration is adapted to oral acceptable composition or formulation, wherein the types include capsule, lozenge, troche, emulsifier, liquid suspension, dispersant and solvent. The common carrier used for oral administration such as lozenge, for example, can be lactose, corn starch, lubricant, magnesium stearate as basic additives. The diluents used for capsule include lactose, dry corn starch. The preparation for liquid suspension or emulsifier formulation is to suspend or dissolve active ingredients with binding emulsifiers or oil interface of suspending agent. Sweetening agents, flavoring agents or coloring matters can also be included.

The aerosol spray for oral use or inhalation composition is prepared by known formulation technologies. For example, the composition is dissolved in physiological saline, added with benzyl alcohol, other suitable preservatives or absorbefacients to enhance bioavailable properties. The composition of the compound provided by the present invention can also be prepared as a suppository which is administered through rectum or vagina.

The injections include hypodermic, peritoneal cavity, vein, muscle, joint cavity, intracranial, synovial fluid, intrathecal injection, aorta injection, thoracic injection, lesion injection or other suitable administration technologies.

Furthermore, the present invention provides a method for treating irritable bowel syndrome, comprising the step of administering to a subject in need thereof an effective amount of the aforementioned pharmaceutical composition. In one embodiment of the present invention, the halo group of the pharmaceutical composition is selected from a group consisting of fluorine, chlorine, bromine and iodine. In another embodiment of the present invention, the heteroaromatic group of the pharmaceutical composition is selected from a group consisting of a pyrrolyl group, a furanyl group, a thiophenyl group, a pyridinyl group, a pyrimidinyl group, a thiazolyl group, an indolyl group, an isoindolyl group, an indazolyl group, a benzofuranyl group, an isobenzofuranyl group, a benzothiophenyl group, a benzimidazolyl group, a benzoxazolyl group and a benzothiazolyl group, providing an antagonism to a 5-$HT_7$ receptor.

In another embodiment of the present invention, the irritable bowel syndrome is treated by providing an antagonism to 5-$HT_7$ receptors. In yet another embodiment of the present invention, the irritable bowel syndrome comprises a pain induced by infection followed by stress and a pain induced by chemically induced inflammation.

In yet another embodiment of the present invention, the irritable bowel syndrome is treated by inhibiting a pain induced by infection followed by stress. In another embodiment of the present invention, the irritable bowel syndrome is treated by inhibiting a pain induced by chemically induced inflammation.

The above aspects and advantages of the present invention will become apparent to those ordinarily skilled in the art after reviewing the detailed descriptions and accompanying drawing.

EXAMPLES

The present invention will now be described more specifically with reference to the following examples. It is to be noted that the following descriptions of this invention are presented herein for the purposes of illustration and description only; it is not intended to be exhaustive or to be limited to the precise form disclosed.

The present invention provides a library of novel derivatives of 8-phenylisoquinoline. The synthesis includes the following 4 schemes.

Scheme 1 (as shown in FIG. 1): The N-phenylethyl-substituted 8-phenyl-tetrahydroisoquinolin-7-ol derivatives were synthesized starting from the commercially available 7-hydroxy-6-methoxy-3,4-dihydroisoquinoline (compound 20) as depicted in FIG. 1. N-alkylation of compound 20 with phenylethyl bromide followed by $NaBH_4$ reduction provided amine 21. Treatment of phenethylamine 21 with $Pb(OAc)_4$ followed by aromatic substitution with HBr produced 8-bromo-tetrahydroisoquinoline 22. The desired target compounds 29-45 were then synthesized from 22 with various substituted-arylboranes using Suzuki coupling reaction condition in moderate yields.

Figure 2:
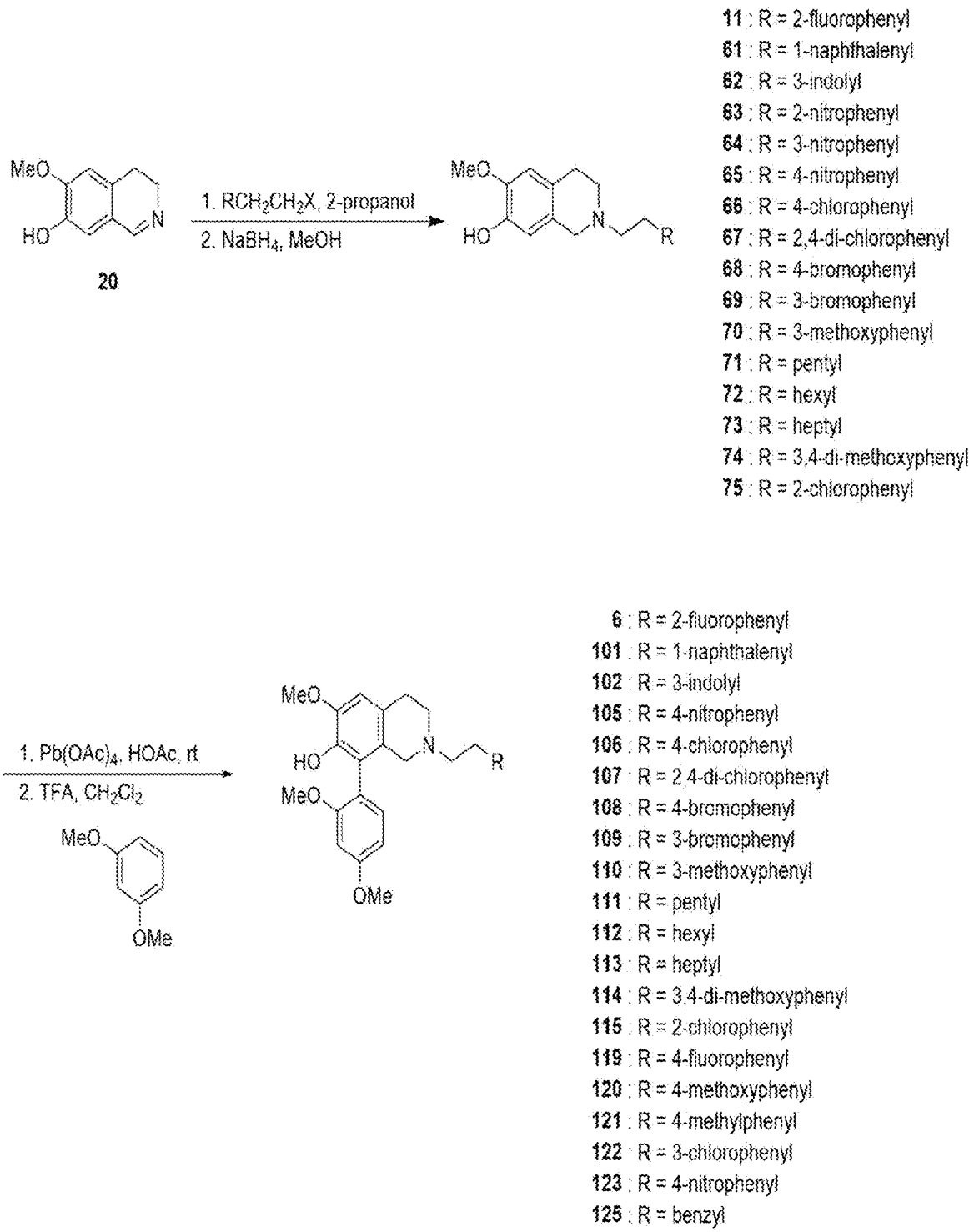
FIG. 2 shows the synthetic scheme 2 of novel derivatives of 8-phenylisoquinoline.

Scheme 2 (as shown in FIG. 2): The N-substituted 8-(2, 4-dimethoxyphenyl)-tetrahydroisoquinolin-7-ols were also prepared starting from the commercially available compound 20 as shown in Scheme 2. Treatment of compound 20 with various halides followed by $NaBH_4$ reduction yielded N-substituted tetrahydroisoquinolin-7-ols 11, and 61-75. Oxidation of compounds 11, and 61-75 with $Pb(OAc)_4$ in acetic acid followed by TFA-catalyzed aromatic substitution with 1,3-dimethoxybenzene afforded the corresponding N-substituted 8-(2,4-dimethoxyphenyl)-6-methoxy-tetrahydroisoquinolin-7-ols 6, and 101-125, respectively.

Figure 3:
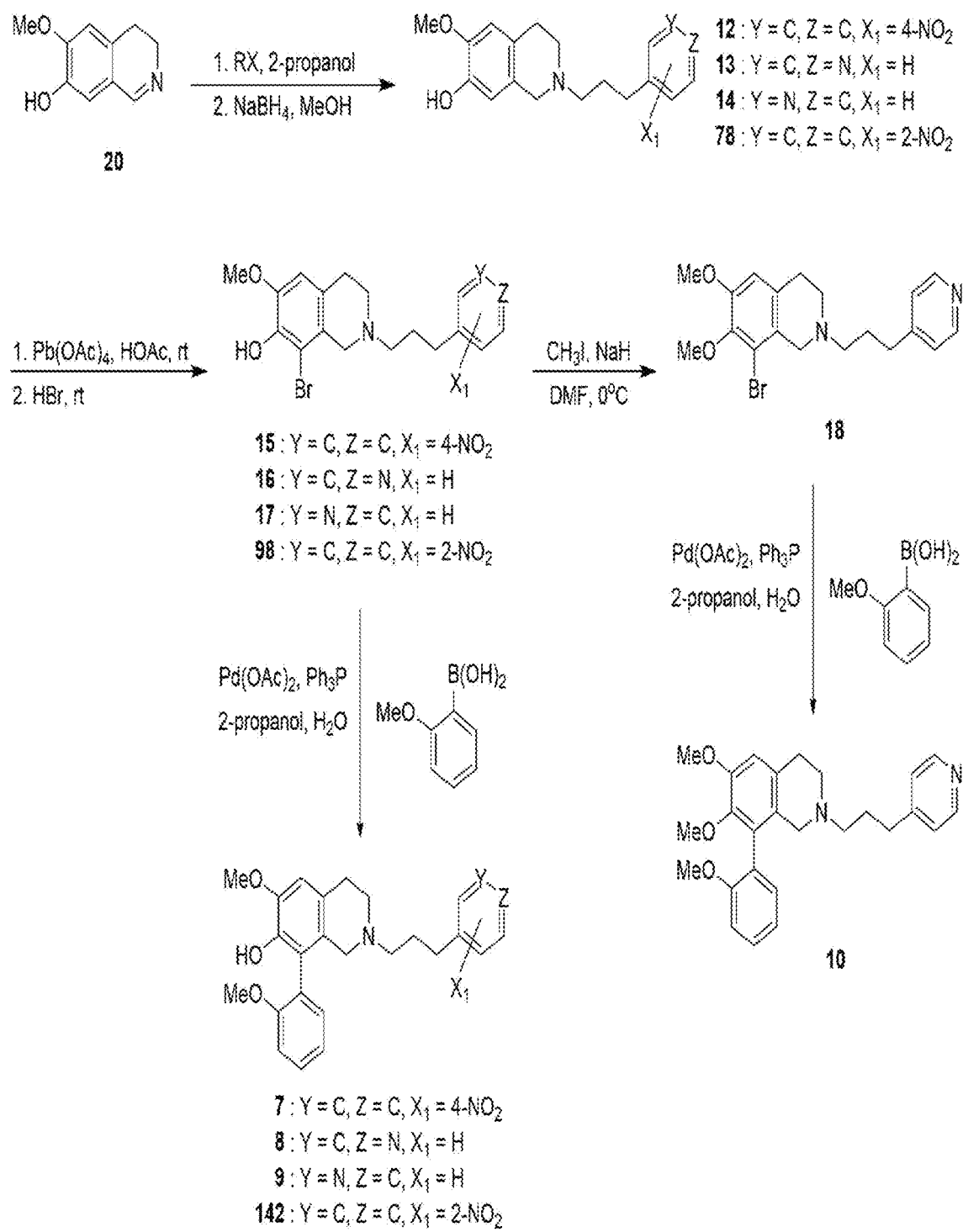
FIG. 3 shows the synthetic scheme 3 of novel derivatives of 8-phenylisoquinoline.

Scheme 3 (as shown in FIG. 3): Treatment of compound 20 with various 3-arylpropyl bromides followed by $NaBH_4$ reduction provided the corresponding N-3-arylpropyl-substituted tetrahydroisoquinolin-7-ol derivatives 12-14 and 78 as depicted in Scheme 3. Bromides 15-17 and 98 were obtained by treatment of compounds 12-14 and 78 with $Pb(OAc)_4$ followed by aromatic substitution with HBr, respectively. O-Methylation of phenols 16 with methyl iodide in the presence of NaH yielded 6,7-dimethoxy-tetrahydroisoquinoline 18. Aryl coupling reaction of compounds 15-18 and 98 under Suzuki reaction condition with various substituted-arylboranes afforded the N-3-arylpropyl-substituted 6-methoxy-8-phenyl-tetrahydroisoquinolin-7-ols 7-10 and 142 in moderate yields, respectively.

Figure 4:
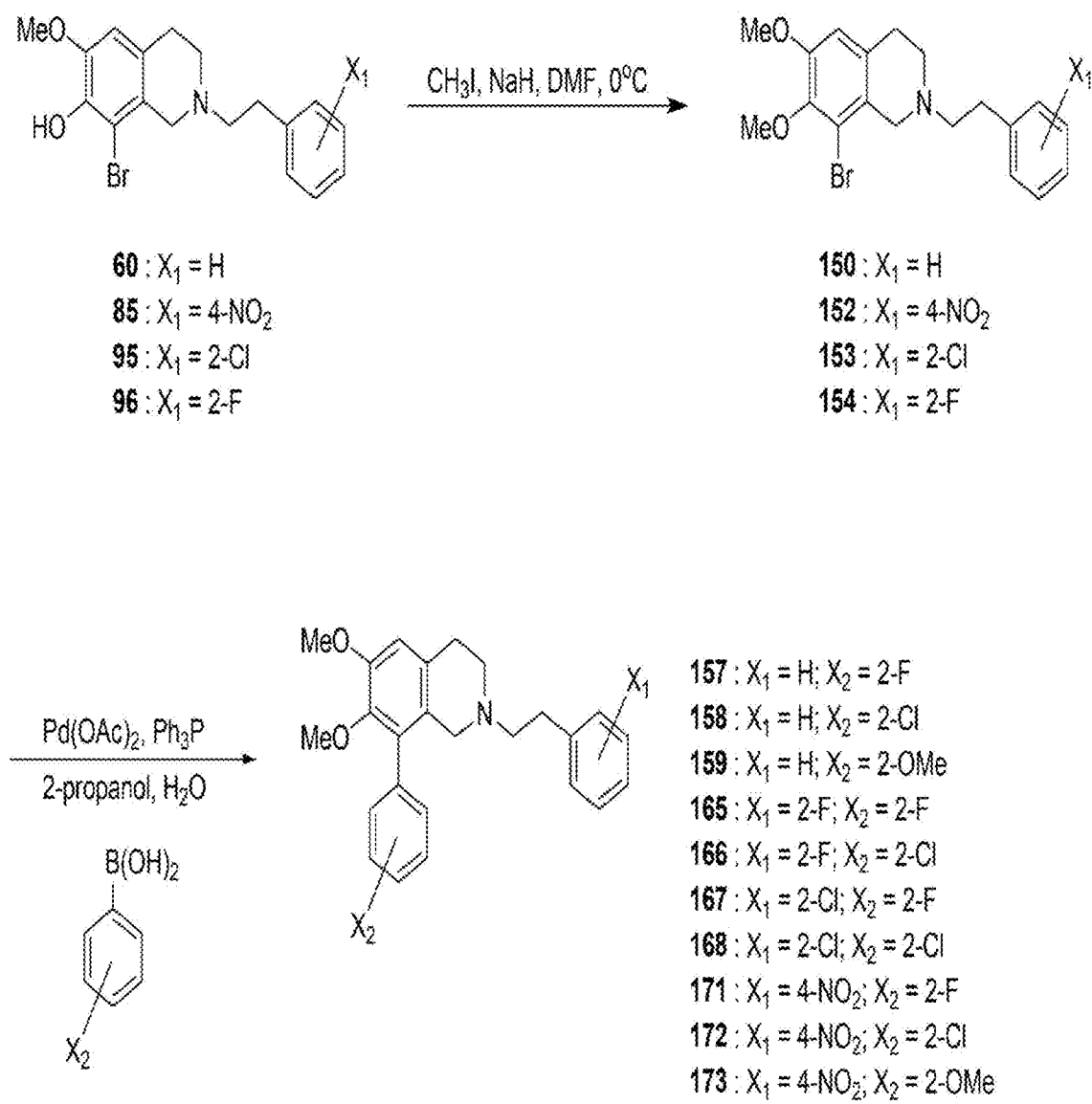
FIG. 4 shows the synthetic scheme 4 of novel derivatives of 8-phenylisoquinoline.

Scheme 4 (as shown in FIG. 4): The N-phenylethyl-substituted 6,7-dimethoxy-8-phenyl-tetrahydroisoquinoline derivatives 157-173 were prepared using N-phenylethyl-substituted 8-bromo-6-methoxy-tetrahydroisoquinolin-7-ols 60-96 as depicted in Scheme 4. O-Methylation of phenols 60-96 with methyl iodide in the presence of NaH gave 6,7-dimethoxy-tetrahydroisoquinolines 150-154, respectively. Aryl coupling reaction of compounds 150-154 with various substituted-arylboranes under Suzuki reaction condition furnished 6,7-dimethoxy-8-phenyl-tetrahydroisoquinolines 157-173, respectively.

The specific synthesizing steps of those compounds depicted in the above schemes 1-4 are as follows:

Compound 21: A mixture of compound 20 (100 mg, 0.56 mmol), 2-phenylethyl bromide (311 mg, 1.68 mmol), and 2-propanol (3.5 mL) was refluxed for 15 hours. The resulting solution was concentrated and MeOH (5 mL) was added to dissolve the residue. The solution was cooled in an ice-bath and then $NaBH_4$ (49 mg, 1.29 mmol) was added slowly under $N_2$. The mixture was stirred for another 10 minutes and then concentrated. The residue was treated with $H_2O$ (20 mL) and $CHCl_3$ (20 mL), and then the organic layer was washed with brine, dried over $MgSO_4$, filtered, and evaporated. The crude residue was chromatographed (silica gel, MeOH/CH$_2$Cl$_2$=1/100) to afford compound 21 as a white solid (146 mg, 0.52 mmol, 92%).

Compound 30: To a solution of C$_{18}$H$_{20}$BrNO$_2$ (50 mg, 0.14 mmol) in 2-propanol (2.0 mL) in a 10-mL thick walled Pyrex reaction vessel, 4-methoxyphenylboronic acid (26 mg, 0.19 mmol) was added. After stirring for 30 min, Pd(OAc)$_2$ (1.3 mg, 0.006 mmol), PPh$_3$ (4.7 mg, 0.02 mmol), 2 M Na$_2$CO$_{3(aq)}$ (0.09 mL, 0.17 mmol), and H$_2$O (0.1 mL) were added. Then the mixture was heated at 140° C. for 10 min in a microwave synthesizer, and H$_2$O (0.35 mL) was added before cooling to room temperature. The resulting solution was diluted with H$_2$O (5 mL) and extracted with EtOAc (5 mL). The organic layer was washed with 5% NaHCO$_{3(aq)}$ and brine. The organic solution was treated with Darco G-60 (100 mg) and stirred at room temperature for 30 min, and then dried over MgSO$_4$, filtered (the sintered glass funnel was charged with Celite to a depth of 1 cm and Florisil was spread evenly on the top of the Celite), and evaporated. The crude residue was chromatographed (silica gel, EtOAc/n-hexane=2/1) to afford an orange oil (40 mg, 0.10 mmol, 73%).

Compounds 29 and 31-40: Table 1 is a parameter table. "Parameter 1" was added into the reaction vessel for microwave-assisted heating and dissolved with "parameter 2" mL 2-propanol. The appearance of the solution was "parameter 3" and the reagent "parameter 4" was added thereinto, and stirred for "parameter 5" minutes. The appearance of the resulting solution was "parameter 6". The Pd(OAc)$_2$ "parameter 7", PPh$_3$ "parameter 8", 2 M Na$_2$CO$_{3(aq)}$ "parameter 9" and "parameter 10" mL H$_2$O were added and heated under the condition of "parameter 11". Before the temperature of the solution was decreased, "parameter 12" mL H$_2$O was added, stirred in the air until reaching room temperature, diluted with "parameter 13" mL EtOAc, and extracted with "parameter 14" mL H$_2$O. The organic layer was washed with 5% NaHCO$_{3(aq)}$, washed with brine, added in "parameter 15" mg Darco G-60, stirred for "parameter 16" minutes, added in MgSO$_4$ for drying, stirred for "parameter 17" minutes, filtered by the sintered glass funnel covered with about 1 cm of Celite and a thin layer of Florisil, concentrated for drying and purified by flash column chromatography (silica gel, "parameter 18") to obtain "parameter 19."

TABLE 1

The parameter table for the synthesis of compounds 29 and 31-40

| | 29 | 31 | 32 | 33 | 34 | 35 |
|---|---|---|---|---|---|---|
| 1 | 2-methoxyphenylboronic acid (65 mg, 0.43 mmol) | C$_{18}$H$_{20}$BrNO$_2$ (100 mg, 0.28 mmol) | C$_{18}$H$_{20}$BrNO$_2$ (150 mg, 0.41 mmol) | phenylboronic acid (43 mg, 0.35 mmol) | 2-(methylthio)phenylboronic acid (59 mg, 0.35 mmol) | 4-(methylthio)phenylboronic acid (125 mg, 0.74 mmol) |
| 2 | 2.0 | 2.0 | 2.0 | 2.0 | 2.0 | 3.0 |
| 3 | transparent colorless | — | — | — | transparent light yellow | transparent colorless |
| 4 | C$_{18}$H$_{20}$BrNO$_2$ (100 mg, 0.28 mmol) | 3-methoxyphenylboronic acid (62 mg, 0.41 mmol) | 3,4,5-trimethoxybenzeneboronic acid (106 mg, 0.50 mmol) | C$_{18}$H$_{20}$BrNO$_2$ (100 mg, 0.28 mmol) | C$_{18}$H$_{20}$BrNO$_2$ (100 mg, 0.28 mmol) | C$_{18}$H$_{20}$BrNO$_2$ (150 mg, 0.41 mmol) |
| 5 | 30 | 30 | 10 | 30 | 30 | 25 |
| 6 | turbid dirt yellow | turbid beige white | turbid beige white | turbid beige white | turbid orange yellow | turbid white |
| 7 | 2.5 mg, 0.011 mmol | 1.2 mg, 0.005 mmol | 1.9 mg, 0.008 mmol | 1.9 mg, 0.008 mmol | 2.2 mg, 0.01 mmol | 2.7 mg, 0.01 mmol |
| 8 | 5.6 mg, 0.021 mmol | 3.1 mg, 0.01 mmol | 5.2 mg, 0.02 mmol | 5.4 mg, 0.02 mmol | 7.0 mg, 0.027 mmol | 10 mg, 0.04 mmol |
| 9 | 0.18 mL, 0.34 mmol | 0.18 mL, 0.34 mmol | 0.27 mL, 0.50 mmol | 0.18 mL, 0.34 mmol | 0.17 mL, 0.34 mmol | 0.25 mL, 0.49 mmol |
| 10 | 0.2 | 0.2 | 0.3 | 0.2 | 0.2 | 0.3 |
| 11 | 120° C. for 20 minutes | 120° C. for 10 minutes | 120° C. for 10 minutes | 120° C. for 10 minutes | 140° C. for 20 minutes | 140° C. for 20 minutes |
| 12 | 0.7 | 0.7 | 1.0 | 0.7 | 0.7 | 1.1 |
| 13 | 10 | 5 | 10 | 10 | 20 | 20 |
| 14 | 10 | 0 | 0 | 0 | 10 | 20 |
| 15 | 100 | 100 | 150 | 117 | 106 | 180 |
| 16 | 5 | 30 | 5 | 15 | 20 | 10 |
| 17 | 10 | 30 | 10 | 10 | 10 | 10 |
| 18 | EA/n-hexane = 1/1 | EA/n-hexane = 1/1 | EA/n-hexane = 1/1 | EA/n-hexane = 1/3 | EA/n-hexane = 1/2 | EA/n-hexane = 1/2 |
| 19 | orange yellow oil products (106 mg, 0.27 mmol, 97%) | light yellow oil products (97 mg, 0.23 mmol, 83%) | light yellow oil products (102 mg, 0.23 mmol, 55%) | light yellow oil products (90 mg, 0.25 mmol, 89%) | orange oil products (66 mg, 0.16 mmol, 58%) | orange oil products (148 mg, 0.37 mmol, 89%) |

| | 36 | 37 | 38 | 39 | 40 |
|---|---|---|---|---|---|
| 1 | 3,4-(methylenedioxy)benzene boronic acid (86 mg, 0.52 mmol) | 2-cyanophenylboronic acid (74 mg, 0.50 mmol) | 2-nitrophenylboronic acid (124 mg, 0.74 mmol) | 2-chlorophenyl boronic acid (77 mg, 0.49 mmol) | 2-acetylphenylboronic acid (80 mg, 0.49 mmol) |
| 2 | 3.0 | 3.0 | 3.0 | 3.0 | 3.0 |

TABLE 1-continued

The parameter table for the synthesis of compounds 29 and 31-40

| 3 | transparent light orange | transparent light yellow | transparent light yellow | transparent colorless | turbid white |
|---|---|---|---|---|---|
| 4 | $C_{18}H_{20}BrNO_2$ (150 mg, 0.41 mmol) | $C_{18}H_{20}BrNO_2$ (151 mg, 0.42 mmol) | $C_{18}H_{20}BrNO_2$ (152 mg, 0.42 mmol) | $C_{18}H_{20}BrNO_2$ (150 mg, 0.41 mmol) | $C_{18}H_{20}BrNO_2$ (149 mg, 0.41 mmol) |
| 5 | 30 | 35 | 30 | 25 | 30 |
| 6 | turbid beige white | turbid white | turbid light yellow | turbid beige white | turbid beige yellow |
| 7 | 3.0 mg, 0.01 mmol | 3.0 mg, 0.01 mmol | 4 mg, 0.018 mmol | 3.0 mg, 0.01 mmol | 3.0 mg, 0.012 mmol |
| 8 | 11 mg, 0.04 mmol | 10 mg, 0.037 mmol | 16 mg, 0.06 mmol | 11 mg, 0.042 mmol | 10 mg, 0.037 mmol |
| 9 | 0.25 mL, 0.49 mmol | 0.25 mL, 0.49 mmol | 0.37 mL, 0.74 mmol | 0.25 mL, 0.49 mmol | 0.25 mL, 0.50 mmol |
| 10 | 0.3 | 0.3 | 0.3 | 0.3 | 0.3 |
| 11 | 140° C. for 20 minutes | 140° C. for 20 minutes | 120° C. for 20 minutes | 140° C. for 20 minutes | 140° C. for 20 minutes |
| 12 | 1.1 | 1.1 | 1.1 | 1.1 | 1.1 |
| 13 | 20 | 20 | 20 | 20 | 20 |
| 14 | 20 | 20 | 20 | 20 | 20 |
| 15 | 197 | 195 | 176 | 160 | 150 |
| 16 | 10 | 10 | 10 | 10 | 10 |
| 17 | 10 | 10 | 10 | 10 | 10 |
| 18 | EA/n-hexane = 1/3 | EA/n-hexane = 1/3 | EA/n-hexane = 1/2 | EA/n-hexane = 1/2 | EA/n-hexane = 1/2 |
| 19 | white solid products (134 mg, 0.33 mmol, 81%) | light yellow oil products (33 mg, 0.09 mmol, 20%) | light yellow oil products (20 mg, 0.05 mmol, 12%) | light yellow oil products (105 mg, 0.27 mmol, 65%) | white solid products (40 mg, 0.10 mmol, 24%) |

Compound 44: To a solution of $C_{18}H_{20}BrNO_2$ (100 mg, 0.28 mmol) in 2-propanol (1.5 mL) in a 10-mL thick walled Pyrex reaction vessel, 3,5-dimethoxybenzeneboronic acid (62 mg, 0.34 mmol) was added. After stirring for 30 min, Pd(OAc)$_2$ (2.2 mg, 0.01 mmol), PPh$_3$ (8.0 mg, 0.03 mmol), 2 M Na$_2$CO$_{3(aq)}$ (0.17 mL, 0.34 mmol), and H$_2$O (0.7 mL) were added. Then the mixture was heated at 140° C. for 10 min in a microwave synthesizer, and H$_2$O (0.35 mL) was added before cooling to room temperature. The resulting solution was diluted with H$_2$O (10 mL) and extracted with EtOAc (10 mL). The organic layer was washed with 5% NaHCO$_{3(aq)}$ (10 mL) and brine. The organic solution was treated with Darco G-60 (100 mg) and stirred at room temperature for 30 min, and then dried over MgSO$_4$, filtered (the sintered glass funnel was charged with Celite to a depth of 1 cm and Florisil was spread evenly on the top of the Celite), and evaporated. The crude residue was chromatographed (silica gel, EtOAc/n-hexane=1/1) to afford a yellow oil (76 mg, 0.18 mmol, 65%).

Compound 45: To a solution of $C_{18}H_{20}BrNO_2$ (100 mg, 0.28 mmol) in 2-propanol (2.0 mL) in a 10-mL thick walled Pyrex reaction vessel, 2,3-dimethoxyphenylboronic acid (62 mg, 0.34 mmol) was added. After stirring for 30 min, Pd(OAc)$_2$ (2.0 mg, 0.009 mmol), PPh$_3$ (3.7 mg, 0.014 mmol), 2 M Na$_2$CO$_3$(aq) (0.18 mL, 0.36 mmol), and H$_2$O (0.2 mL) were added. Then the mixture was heated at 120° C. for 10 min in a microwave synthesizer, and H$_2$O (0.7 mL) was added before cooling to room temperature. The resulting solution was diluted with H$_2$O (5 mL) and extracted with EtOAc (5 mL). The organic layer was washed with 5% NaHCO$_{3(aq)}$ (5 mL) and brine. The organic solution was treated with Darco G-60 (100 mg) and stirred at room temperature for 30 min, and then dried over MgSO$_4$, filtered (the sintered glass funnel was charged with Celite to a depth of 1 cm and Florisil was spread evenly on the top of the Celite), and evaporated. The crude residue was chromatographed (silica gel, EtOAc/n-hexane=1/1) to afford a yellow oil (82 mg, 0.20 mmol, 71%).

Compounds 15, 60, 85, 95-96, and 98: Table 2 is a parameter table. The starting material "parameter 1" was added into a reaction flask at room temperature under N$_2$, and "parameter 2" mL HOAc was added thereinto. The Pb(OAc)$_4$ "parameter 3" was added, and then the solution was "parameter 4", poured into a conical flask and added with "parameter 5" mL Na$_2$CO$_3$ (sat) slowly. The pH of the aqueous layer was alkaline (pH="parameter 6"). The solids produced in neutralization was filtered. The filter cake was washed with CH$_2$Cl$_2$. The filtrate was extracted with "parameter 7" mL CH$_2$Cl$_2$. The organic layer was washed with brine, added with MgSO$_4$ for drying, stirred for 5 minutes, filtered with the sintered glass funnel and concentrated for drying to obtain "parameter 8" product. The crude product was used in the following reaction without further purification.

The solution which was added in HBr "parameter 9" in the room temperature air and the appearance of the solution was "parameter 10." After stirring for "parameter 11" hours, "parameter 12" mL Na$_2$CO$_3$ (sat) and "parameter 13" mL CH$_2$Cl$_2$ were added slowly to the solution. The pH of the aqueous layer was alkaline (pH="parameter 14"), and then the "parameter 15" mL CH$_2$Cl$_2$ and "parameter 16" mL H$_2$O were added for extraction. The organic layer was washed with brine, added with MgSO$_4$ for drying, stirred for 5 minutes, filtered with the sintered glass funnel and concentrated for drying to obtain crude product "parameter 17" mg. The "parameter 19" was afforded after flash column chromatography (silica gel, "parameter 18").

TABLE 2

The parameter table for the synthesis of compounds 15, 60, 85, 95-96, and 98

| | 15 | 60 | 85 | 95 | 96 | 98 |
|---|---|---|---|---|---|---|
| 1 | $C_{19}H_{22}N_2O_4$ (320 mg, 0.93 mmol) | $C_{18}H_{21}NO_2$ (351 mg, 1.24 mmol) | $C_{18}H_{20}N_2O_4$ (503 mg, 1.53 mmol) | $C_{18}H_{20}ClNO_2$ (1000 mg, 3.15 mmol) | $C_{18}H_{20}FNO_2$ (1002 mg, 3.32 mmol) | $C_{19}H_{22}N_2O_4$ (285 mg, 0.83 mmol) |
| 2 | 4.7 | 6.2 | 7.6 | 15.5 | 16.5 | 4.2 mL |
| 3 | 636 mg, 1.43 mmol | 830 mg, 1.87 mmol | 1034 mg, 2.33 mmol | 2101 mg, 4.74 mmol | 2262 mg, 5.10 mmol | 562 mg, 1.27 mmol |
| 4 | red brown | deep red coffee color | transparent red coffee color | transparent deep red brown | tranparent burgundy red | transparent red brown |
| 5 | 25 | 40 | 60 | 100 | 130 | 25 |
| 6 | 8-9 | 8-9 | 8-9 | 8-9 | 8-9 | 8-9 |
| 7 | 40 | 50 | 80 | 100 | 130 | 40 |
| 8 | deep orange red solid (303 mg, 0.76 mmol) | deep orange red solid (282 mg, 0.83 mmol) | red brown solid (498 mg, 1.29 mmol) | red brown solid (1089 mg, 2.91 mmol) | red brown solid (1088 mg, 3.04 mmol) | brown oil (263 mg, 0.66 mmol) |
| 9 | 5 mL, 48% wt | 6 mL, 48% wt | 10 mL, 48% wt | 15 mL, 48% wt | 15 mL, 48% wt | 5 mL, 48% wt |
| 10 | turbid orange | turbid yellow | turbid orange | turbid orange | turbid orange | turbid orange |
| 11 | 1 | 3 | 2 | 1.5 | 1.5 | 0.5 |
| 12 | 35 | 35 | 70 | 100 | 100 | 35 |
| 13 | 20 | 20 | 50 | 50 | 50 | 20 |
| 14 | 8-9 | 8-9 | 8-9 | 9-10 | 9-10 | 8-9 |
| 15 | 20 | 15 | 50 | 80 | 60 | 50 |
| 16 | 0 | 0 | 30 | 30 | 10 | 0 |
| 17 | 225 | 344 | 433 | 1013 | 973 | 195 |
| 18 | MeOH/$CH_2Cl_2$ = 1/100 | EA/n-hexane = 1/2 | EA/n-hexane = 1/1 | MeOH/$CH_2Cl_2$ = 1/100 | EA/n-hexane = 1/3 | MeOH/$CH_2Cl_2$ = 1/90 |
| 19 | orange yellow oil products (179 mg, 0.42 mmol, 46%) | beige white solid products (260 mg, 0.72 mmol, 58%) | yellow solid products (363 mg, 0.89 mmol, 59%) | white solid products (747 mg, 1.88 mmol, 60%) | white solid products (752 mg, 1.98 mmol, 60%) | orange yellow oil products (170 mg, 0.40 mmol, 49%) |

Compounds 11-12, 63-67, 67-70, 74-75, and 78: Table 3 is a parameter table. The starting material "parameter 1" was added into a flask at room temperature under $N_2$, and then the "parameter 2" mL IPA and "parameter 3" were added thereinto. The starting material was dissolved at "parameter 4" ° C. The appearances of reaction solution were "parameter 5" and "parameter 7" in about "parameter 6" minutes, and then the solution was heated at 110~120° C. for "parameter 8" hours and concentrated in room temperature. The "parameter 9" mL MeOH was added and the resulting mixture was stirred for "parameter 10" minutes. To the solution, which is "parameter 11" in a ice-bath, $NaBH_4$(s) "parameter 12" was added slowly under $N_2$ and stirred for "parameter 13" minutes. The solution, which is "parameter 14," was added with "parameter 15" mL $H_2O$ and extracted with "parameter 16" mL $CHCl_3$. The organic layer was added with $MgSO_4$ for drying, stirred for "parameter 17" minutes, filtered, and concentrated to obtain "parameter 18". The "parameter 20" was afforded after flash column chromatography (silica gel, "parameter 19").

TABLE 3

The parameter table for the synthesis of compounds 11-12, 63-67, 67-70, 74-75, and 78

| | | 11 | 12 | 63 | 64 | 65 | 66 |
|---|---|---|---|---|---|---|---|
| | 1 | $C_{10}H_{11}NO_2$ (20, 1000 mg, 5.64 mmol) | $C_{10}H_{11}NO_2$ (20, 300 mg, 1.69 mmol) | $C_{10}H_{11}NO_2$ (20, 300 mg, 1.69 mmol) | $C_{10}H_{11}NO_2$ (20, 300 mg, 1.69 mmol) | $C_{10}H_{11}NO_2$ (20, 1001 mg, 5.65 mmol) | $C_{10}H_{11}NO_2$ (20, 301 mg, 1.70 mmol) |
| | 2 | 35 | 10 | 10 | 10 | 35 | 14 |
| | 3 | 2-fluorophenethyl bromide (3438 mg, 16.93 mmol) | $C_9H_{10}BrNO_2$ (1215 mg, 4.98 mmol) | $C_8H_8NO_2Br$ (1127 mg, 4.89 mmol) | $C_8H_8NO_2Br$ (866 mg, 3.76 mmol) | $C_8H_8NO_2Br$ (3810 mg, 16.56 mmol) | 4-chlorophenethyl bromide (1115 mg, 5.08 mmol) |
| | 4 | 80 | 88 | 60 | 75 | — | 80 |
| | 5 | transparent orange | transparent white | transparent light yellow | transparent light yellow | — | transparent yellow |
| | 6 | — | 210 | 30 | 10 | — | 120 |

TABLE 3-continued

The parameter table for the synthesis of compounds
11-12, 63-67, 67-70, 74-75, and 78

|  |  |  |  |  |  |  |
|---|---|---|---|---|---|---|
| 7 | — | turbid yellow | turbid yellow | turbid yellow | transparent orange yellow | turbid yellow |
| 8 | 18 | 19.5 | 18 | 16 | 17 | 24 |
| 9 | 35 | 15 | 15 | 15 | 35 | 15 |
| 10 | 10 | 10 | 10 | 10 | 10 | 10 |
| 11 | transparent light brown | turbid yellow | turbid yellow | turbid yellow | — | transparent yellow |
| 12 | 836 mg, 22.1 mmol | 266 mg, 7.03 mmol | 264 mg, 6.97 mmol | 206 mg, 3.39 mmol | 853 mg, 22.53 mmol | 576 mg, 15.2 mmol |
| 13 | 20 | 20 | 20 | 20 | 10 | 20 |
| 14 | opaque pinky orange | transparent brown | turbid yellow | turbid orange | — | opaque orange |
| 15 | 100 | 30 | 30 | 0 | 0 | 30 |
| 16 | 100 | 30 | 30 | 30 | 100 | 30 |
| 17 | 5 | 5 | 5 | 5 | 5 | 5 |
| 18 | light orange solid products | orange oil products | orange solid crude produts | orange solid crude produts | — | orange solid crude produts |
| 19 | MeOH/CH$_2$Cl$_2$ = 1/90 | MeOH/CH$_2$Cl$_2$ = 1/90 | MeOH/CH$_2$Cl$_2$ = 1/60 | MeOH/CH$_2$Cl$_2$ = 1/60 | MeOH/CH$_2$Cl = 1/80 | MeOH/CH$_2$Cl$_2$ = 1/90 |
| 20 | white solid products (1501 mg, 4.98 mmol, 88%) | yellow oil products (503 mg, 1.47 mmol, 87%) | canary yellow solid products (439 mg, 1.34 mmol, 79%) | white solid products (541 mg, 1.65 mmol, 97%) | beige yellow solid products (1558 mg, 4.74 mmol, 84%) | white solid products (448 mg, 1.41 mmol, 81%) |

|  | 67 | 69 | 70 | 74 | 75 | 78 |
|---|---|---|---|---|---|---|
| 1 | C$_{10}$H$_{11}$NO$_2$ (20, 300 mg, 1.69 mmol) | C$_{10}$H$_{11}$NO$_2$ (20, 300 mg, 1.69 mmol) | C$_{10}$H$_{11}$NO$_2$ (20, 301 mg, 1.70 mmol) | C$_{10}$H$_{11}$NO$_2$ (20, 300 mg, 1.69 mmol) | C$_{10}$H$_{11}$NO$_2$ (20, 1002 mg, 5.64 mmol) | C$_{10}$H$_{11}$NO$_2$ (20, 300 mg, 1.69 mmol) |
| 2 | 10 | 10 | 10 | 10 | 35 | 10 |
| 3 | C$_8$H$_7$BrCl$_2$ (1.00 g, 3.94 mmol) | C$_8$H$_8$Br$_2$ (1.00 g, 3.79 mmol) | C$_{10}$H$_{13}$O$_2$Br (1.0 g, 4.65 mmol) | C$_{10}$H$_{13}$O$_2$Br (1.0 g, 4.08 mmol) | 2-chlorophenethyl bromide (3716 mg, 16.93 mmol) | C$_9$H$_{10}$BrNO$_2$ (989 mg, 4.05 mmol) |
| 4 | 80 | 80 | 70 | 80 | 80 | 75 |
| 5 | transparent yellow | transparent yellow | transparent light yellow | transparent orange yellow | transparent yellow | transparent white |
| 6 | 120 | 90 | 120 | 120 | — | 60 |
| 7 | turbid yellow | turbid yellow | turbid yellow | turbid yellow | — | turbid yellow |
| 8 | 25 | 19 | 19 | 18 | 17 | 19.5 |
| 9 | 15 | 15 | 15 | 15 | 35 | 15 |
| 10 | 10 | 10 | — | — | 10 | 10 |
| 11 | transparent yellow | transparent yellow | transparent yellow | transparent orange yellow | turbid yellow | turbid yellow |
| 12 | 257 mg, 6.78 mmol | 270 mg, 7.14 mmol | 272 mg, 7.17 mmol | 270 mg, 7.13 mmol | 825 mg, 21.8 mmol | 271 mg, 7.16 mmol |
| 13 | 20 | 20 | 20 | 20 | 20 | 20 |
| 14 | opaque orange | opaque orange | transparent orange | transparent orange | opaque pinky orange | transparent light orange |
| 15 | 30 | 30 | 30 | 30 | 100 | 30 |
| 16 | 30 | 30 | 30 | 30 | 100 | 30 |
| 17 | 5 | 5 | 5 | 5 | 5 | 5 |
| 18 | orange solid crude products | orange solid crude produts | orange solid products | orange yellow solid products | light orange solid products | orange oil products |
| 19 | MeOH/CH$_2$Cl$_2$ = 1/100 | MeOH/CH$_2$Cl$_2$ = 1/100 | MeOH/CH$_2$Cl$_2$ = 1/100 | MeOH/CH$_2$Cl$_2$ = 1/60 | MeOH/CH$_2$Cl$_2$ = 1/90 | MeOH/CH$_2$Cl$_2$ = 1/90 |
| 20 | yellow solid products (442 mg, 1.26 mmol, 74%) | white solid products (626 mg, 1.73 mmol, 102%) | white solid products (504 mg, 1.61 mmol, 95%) | beige white solid products (452 mg, 1.32 mmol, 78%) | white solid products (1601 mg, 5.04 mmol, 89%) | yellow oil products (492 mg, 1.44 mmol, 85%) |

Compound 68: A mixture of $C_{10}N_{11}NO_2$ (300 mg, 1.69 mmol), $C_8H_8Br_2$ (1.00 g, 3.79 mmol), and 2-propanol (10 mL) was heated to reflux for 23 h. The resulting solution was cooled to room temperature, and evaporated. The crude was dissolved in MeOH (15 mL), cooled to 0° C. in ice-bath, and then $NaBH_4$ (420 mg, 11.1 mmol) was added in portions under $N_2$. The mixture was stirred for another 20 min and then concentrated. The residue was treated with $CHCl_3$ (30 mL) and $H_2O$ (30 mL) and then the organic layer was dried over $MgSO_4$, filtered and evaporated. The purification was performed by the precipitation method. The crude product was dissolved with 5 mL of EtOAc, and then the product was precipitates with 10 mL of n-hexane to afford a beige solid (620 mg, 1.71 mmol).

Compound 121: To a solution of $C_{19}H_{23}NO_2$ (250 mg, 0.84 mmol) in HOAc (4.2 mL), $Pb(OAc)_4$ (579 mg, 1.31 mmol) was added and the mixture was stirred at room temperature under $N_2$ for 15 min. The reaction mixture was diluted with $CH_2Cl_2$ and $Na_2CO_3$ (sat) (20 mL) was added slowly. The solids formed in neutralization were removed by filtration and washed with $CH_2Cl_2$. The combined filtrate was extracted with $CH_2Cl_2$ (35 mL), and then the organic layer was washed with brine, dried over $MgSO_4$, filtered, and evaporated to afford a brown oil (480 mg, 1.35 mmol), which was used in the following reaction without further purification. To a solution of the crude oil in $CH_2Cl_2$ (17 mL), 1,3-dimethoxybenzene (0.17 mL, 1.3 mmol) and trifluoroacetic acid (0.84 mL) were added. The resulting mixture was stirred at room temperature for 30 min, and then $Na_2CO_3$ (sat) (20 mL) was added slowly. The resulting solution was extracted with $CH_2Cl_2$ (18 mL) and then the organic layer was washed with brine, dried over $MgSO_4$, filtered, and evaporated. The crude residue was chromatographed (silica gel, $MeOH/CH_2Cl_2=1/10$) to afford a red-brown oil (214 mg, 0.49 mmol, 59%).

Compounds 6, 105-110, 114-115, 120, 122, 123 and 125: Table 4 is a parameter table. The starting material "parameter 1" was added into a flask at room temperature under $N_2$ and dissolved with "parameter 2" mL HOAc. The solution which was "parameter 3" was added with $Pb(OAc)_4$ "parameter 4," and then the resulting solution which was "parameter 5" was stirred for "parameter 6" minutes, poured into a 125 mL conical flask, stirred and added slowly with "parameter 7" mL $Na_2CO_3$(sat). The pH of the aqueous layer was alkaline (pH=8-9). The solid produced by neutralization was filtered and washed with $CH_2Cl_2$. The filtrate was extracted with "parameter 8" mL $CH_2Cl_2$. The organic layer was washed with brine, added with $MgSO_4$ for drying, stirred for 5 minutes, filtered, and concentrated to afford "parameter 9". The crude product was used in the following reaction without further purification.

The crude product was dissolved in "parameter 10" mL $CH_2Cl_2$ at room temperature under $N_2$. The solution which was "parameter 11" was added with 1,3-dimethoxybenzene "parameter 12" and trifluoroacetic acid "parameter 13". The color of the solution turned into "parameter 14". After the solution was stirred for "parameter 15" minutes, "parameter 16" mL $Na_2CO_3$(sat) was added slowly. The pH of the aqueous layer was alkaline (pH=8-9), and "parameter 17" mL $CH_2Cl_2$ was added for extraction. The organic layer was washed with brine, added with $MgSO_4$ for drying, stirred for 5 minutes, filtered, and concentrated to obtain "parameter 18" mg crude product. The "parameter 20" was afforded after flash column chromatography (silica gel, "parameter 19").

TABLE 4

The parameter table for the synthesis of compounds 6, 105-110, 114-115, 120, 122, 123 and 125

| | 6 | 105 | 106 | 107 | 108 |
|---|---|---|---|---|---|
| 1 | $C_{18}H_{20}FNO_2$ (251 mg, 0.83 mmol) | $C_{18}H_{20}N_2O_4$ (250 mg, 0.76 mmol) | $C_{18}H_{20}ClNO_2$ (160 mg, 0.50 mmol) | $C_{18}H_{19}Cl_2NO_2$ (250 mg, 0.71 mmol) | $C_{18}H_{20}BrNO_2$ (250 mg, 0.69 mmol) |
| 2 | 4.2 | 3.8 | 2.5 | 3.6 | 3.5 |
| 3 | light orange yellow | transparent light yellow | transparent light yellow | transparent light green | transparent light yellow |
| 4 | 605 mg, 1.36 mmol | 509 mg, 1.15 mmol | 337 mg, 0.76 mmol | 473 mg, 1.07 mmol | 459 mg, 1.04 mmol |
| 5 | translucent red coffee color | transparent red brown | deep coffee color | red black | transparent coffee color |
| 6 | 15 | 15 | 60 | 27 | 15 |
| 7 | 25 | 25 | 20 | 25 | 40 |
| 8 | 35 | | 40 | 40 | 50 |
| 9 | red coffee color oil products (285 mg, 0.79 mmol) | red coffee color oil products (240 mg, 0.62 mmol) | coffee color oil products (218 mg, 0.58 mmol) | red coffe color oil products (291 mg, 0.71 mmol) | deep coffee color oil products (214 mg, 0.51 mmol) |
| 10 | 16 | 15 | 12 | 14 | 10 |
| 11 | transparent red coffee color | transparent deep red brown | transparent red coffee color | transparent red coffee color | transparent red coffee color |
| 12 | 0.16 mL, 1.2 mmol | 0.14 mL, 1.1 mmol | 0.11 mL, 0.87 mmol | 0.14 mL, 1.06 mmol | 0.10 mL, 0.77 mmol |
| 13 | 0.79 mL | 0.73 mL | 0.58 mL | 0.71 mL | 0.51 mL |
| 14 | transparent red coffee color to transparent light coffee color | transparent deep black tea color to transparent tea color | transparent red coffee brown to transparent light coffee color | transparent red coffee brown to transparent light coffee color | transparent red coffee brown to transparent light coffee color |

TABLE 4-continued

The parameter table for the synthesis of compounds 6,
105-110, 114-115, 120, 122, 123 and 125

| | | | | | |
|---|---|---|---|---|---|
| 15 | 30 | 30 | 60 | 30 | 30 |
| 16 | 20 | 25 | 10 | 20 | 30 |
| 17 | 19 | 20 | 23 | 26 | 30 |
| 18 | 417 | 480 | 327 | 490 | 325 |
| 19 | MeOH/CH$_2$Cl$_2$/NH$_4$OH = 1/100/0.1 | EA/n-hexane = 1/1 | MeO/CH$_2$Cl$_2$/NH$_4$OH = 1/100/0.1 | MeOH/CH$_2$Cl$_2$/NH$_4$OH = 1/100/0.1 | MeOH/CH$_2$Cl$_2$/NH$_4$OH = 1/100/0.1 |
| 20 | light orange yellow solid products (126 mg, 0.29 mmol, 35%) | light orange yellow solid products (151 mg, 0.33 mmol, 43%) | coffee color oil products (130 mg, 0.29 mmol, 57%) | coffee color oil products (152 mg, 0.31 mmol, 44%) | red coffee color oil products (39 mg, 0.11 mmol, 11%) |

| | 109 | 110 | 114 | 115 | 120 |
|---|---|---|---|---|---|
| 1 | C$_{18}$H$_{20}$BrNO$_2$ (250 mg, 0.69 mmol) | C$_{19}$H$_{23}$NO$_3$ (250 mg, 0.80 mmol) | C$_{19}$H$_{23}$NO$_2$ (250 mg, 0.73 mmol) | C$_{18}$H$_{20}$ClNO$_2$ (250 mg, 0.79 mmol) | C$_{19}$H$_{23}$NO$_3$ (250 mg, 0.798 mmol) |
| 2 | 3.6 | 4 | 3.7 | 4 | 4 |
| 3 | transparent light green | transparent light yellow | transparent light yellow | transparent light orange yellow | light yellow |
| 4 | 470 mg, 1.06 mmol | 569 mg, 1.28 mmol | 505 mg, 1.14 mmol | 570 mg, 1.29 mmol | 532 mg, 1.20 mmol |
| 5 | transparent coffee color | transparent red coffee color | transparent red coffee color | translucent red coffee color | deep coffee color |
| 6 | 15 | 15 | 15 | 15 | 15 |
| 7 | 25 | 25 | 30 | 25 | 25 |
| 8 | 35 | 40 | 35 | 35 | 35 |
| 9 | red coffee color oil products (262 mg, 0.62 mmol) | red coffee color oil products (243 mg, 0.65 mmol) | red coffee color oil products (253 mg, 0.63 mmol) | red coffee color oil products (300 mg, 0.80 mmol) | red coffee color oil products (290 mg, 0.781 mmol) |
| 10 | 13 | 13 | 13 | 16 | 16 |
| 11 | transparent red coffee color | transparent red coffee color | coffee color | transparent red coffee color | transparent red coffee color |
| 12 | 0.12 mL, 0.93 mmol | 0.13 mL, 0.98 mmol | 0.13 mL, 0.95 mmol | 0.16 mL, 1.2 mmol | 0.15 mL, 1.2 mmol |
| 13 | 0.62 mL | 0.65 mL | 0.63 mL | 0.79 mL | 0.78 mL |
| 14 | transparent red coffee brown to transparent light coffee color | transparent red coffee color to transparent light coffee color | coffee color to light coffee color | transparent red coffee color to transparent light coffee color | transparent red coffee color to transparent coffee color |
| 15 | 70 | 30 | 30 | 30 | 30 |
| 16 | 15 | 20 | 20 | 25 | 25 |
| 17 | 27 | 22 | 22 | 19 | 19 |
| 18 | 342 | 450 | 433 | 480 | 560 |
| 19 | EtOAc/n-hexane = 1/2 | EA/n-hexane = 1/1 | MeOH/CH$_2$Cl$_2$ = 1/100 | EA/n-hexane = 1/2 | MeOH/CH$_2$Cl$_2$/NH$_4$OH = 1/100/0.1 |
| 20 | light brown oil products (80 mg, 0.18 mmol, 26%) | light brown oil products (217 mg, 0.48 mmol, 60%) | red coffee color oil products (129 mg, 0.26 mmol, 36%) | orange solid products (128 mg, 0.28 mmol, 36%) | coffee color oil products (162 mg, 0.36 mmol, 45%) |

| | 122 | 123 | 125 |
|---|---|---|---|
| 1 | C$_{18}$H$_{20}$ClNO$_2$ (250 mg, 0.79 mmol) | C$_{19}$H$_{23}$NO$_3$ (250 mg, 0.80 mmol) | C$_{19}$H$_{23}$NO$_2$ (251 mg, 0.84 mmol) |
| 2 | 4.2 | 4 | 4.3 |
| 3 | transparent orange yellow | transparent orange yellow | transparent light orange yellow |
| 4 | 540 mg, 1.22 mmol | 578 mg, 1.30 mmol | 580 mg, 1.31 mmol |
| 5 | deep coffee color | deep coffee color | transparent red coffee color |
| 6 | 17 | 15 | 15 |
| 7 | 25 | 25 | 35 |
| 8 | 35 | 35 | 35 |

TABLE 4-continued

The parameter table for the synthesis of compounds 6,
105-110, 114-115, 120, 122, 123 and 125

| | | | |
|---|---|---|---|
| 9 | red coffee color oil products (286 mg, 0.76 mmol) | deep red coffee color oil products (290 mg, 0.78 mmol) | red coffee color oil products (283 mg, 0.80 mmol) |
| 10 | 13 | 16 | 16 |
| 11 | transparent red coffee color | transparent deep red coffee color | transparent red coffee color |
| 12 | 0.15 mL, 1.1 mmol | 0.15 mL, 1.2 mmol | 0.16 mL, 1.2 mmol |
| 13 | 0.76 mL | 0.78m | 0.8 mL |
| 14 | transparent red coffee color to transparent coffee color | transparent deep red coffee color to deep coffee color | transparent deep red coffee color to transparent light coffee color |
| 15 | 33 | 30 | 30 |
| 16 | 25 | 25 | 25 |
| 17 | 22 | 19 | 19 |
| 18 | 430 | 430 | 506 |
| 19 | EA/n-hexane = 1/1 | EA/n-hexane = 1/1 | MeOH/CH$_2$Cl$_2$ = 1/200 |
| 20 | orange yellow solid products (151 mg, 0.33 mmol, 42%) | light brown oil products (140 mg, 0.31 mmol, 39%) | light orange yellow solid products (135 mg, 0.31 mmol, 37%) |

Compounds 7 and 142: Table 5 is a parameter table. "Parameter 1" and 2-methoxyphenylboronic acid (46 mg, 0.30 mmol) were added into the reaction vessel for microwave-assisted heating and dissolved with 2-propanol (2 mL), and stirred for 30 minutes. Pd(OAc)$_2$ "parameter 2", PPh$_3$ "parameter 3", 2 M Na$_2$CO$_{3(aq)}$ (0.14 mL, 0.28 mmol), and H$_2$O (0.2 mL) were added and the mixture was heated at 120° C. for 20 minutes using a microwave synthesizer. Before the temperature of the solution was decreased, the solution was added with H$_2$O (0.7 mL), stirred in the air until reaching room temperature, diluted with 10 mL of EtOAc, and extracted with 10 mL of H$_2$O. The organic layer was washed with 5% NaHCO$_{3(aq)}$, washed with brine, added in "parameter 4" mg Darco G-60, stirred for 10 minutes, added in MgSO$_4$ for drying, stirred for 10 minutes, filtered by the sintered glass funnel covered with about 1 cm of Celite and a thin layer of Florisil, and concentrated. The crude product was purified by flash column chromatography (silica gel, "parameter 5") to obtain a yellow oil "parameter 6." Free base "parameter 7" was dissolved in CH$_2$Cl$_2$, and then a solution of HCl in CH$_2$Cl$_2$ was added until pH=1. The resulting mixture was concentrated to obtain hydrochloride salt "parameter 8".

TABLE 5

The parameter table for the synthesis of compounds 7 and 142

| | 7 | 142 |
|---|---|---|
| 1 | 103 mg, 0.24 mmol | 104 mg, 0.25 mmol |
| 2 | 1.4 mg, 0.006 mmol | 2.0 mg, 0.009 mmol |
| 3 | 6.5 mg, 0.024 mmol | 5.9 mg, 0.022 mmol |
| 4 | 112 | 117 |
| 5 | 1/4 | 2/1 |
| 6 | 88 mg, 0.20 mmol, 83% | 76 mg, 0.17 mmol, 72% |
| 7 | 83 mg, 0.20 mmol | 18 mg, 0.04 mmol |
| 8 | beige white solid products (100 mg, 0.20 mmol) | light yellow oil products (20 mg, 0.04 mmol) |

Compound 150: To a solution of C$_{18}$H$_{20}$BrNO$_2$ (100 mg, 0.28 mmol) in DMF (2 mL), trimethylphenyl-ammonium chloride ((CH$_3$)$_3$PhNCl, 102 mg, 0.59 mmol) and t-BuOK (67 mg, 0.60 mmol) were added. The suspension was heated to 60° C. under N$_2$ for 3.5 h, and then (CH$_3$)$_3$PhNCl (102 mg, 0.59 mmol) was added and heated to 70° C. for 4.5 h. After cooling to room temperature, the reaction mixture was treated with CHCl$_3$ (10 mL) and 5% NaOH$_{(aq)}$ (20 mL). The organic layer was washed with brine, dried over MgSO$_4$, filtered, and evaporated. The crude residue was chromatographed (silica gel, EtOAc/n-hexane=1/4) to afford a yellow solid (83 mg, 0.22 mmol, 79%).

Compound 152: To a solution of C$_{18}$H$_{19}$BrN$_2$O$_4$ (406 mg, 1.00 mmol) in DMF (9 mL), which was cooled to 0° C. and degassed, NaH (40 mg, 1.67 mmol) and CH$_3$I (0.06 mL, 0.98 mmol) in DMF (1 mL) were added. After stirring for 10 min, NH$_4$Cl (111 mg, 2.08 mmol) was added, and then the reaction mixture was treated with diethyl ether (100 mL) and H$_2$O (100 mL). The organic layer was washed with brine, dried over MgSO$_4$, filtered and evaporated. The crude residue was chromatographed (silica gel, EtOAc/n-hexane=1/2) to afford a yellow solid (123 mg, 0.29 mmol, 30%).

Compound 153: To a solution of C$_{18}$H$_{19}$BrClNO (300 mg, 0.75 mmol) in DMF (6 mL), (CH$_3$)$_3$PhNCl (542 mg, 3.16 mmol) and t-BuOK (333 mg, 2.97 mmol) were added. The suspension was heated to 60° C. under N$_2$ for 16 h, and then heated to 70° C. for 1 h. After cooling to room temperature, the reaction mixture was treated with Et$_2$O (100 mL) and H$_2$O (100 mL). The organic layer was washed with brine, dried over MgSO$_4$, filtered, and evaporated. The crude residue was chromatographed (silica gel, EtOAc/n-hexane=1/4) to afford a white solid (189 mg, 0.46 mmol, 61%).

Compound 154: To a solution of C$_{18}$H$_{19}$BrFNO$_2$ (400 mg, 1.05 mmol) in DMF (8 mL), (CH$_3$)$_3$PhNCl (727 mg, 4.23 mmol) and t-BuOK (468 mg, 4.17 mmol) were added. The suspension was heated to 70° C. under N$_2$ for 16 h. After cooling to room temperature, the reaction mixture was treated with Et$_2$O (100 mL) and H$_2$O (100 mL). The organic layer was washed with brine, dried over MgSO$_4$, filtered, and evaporated. The crude residue was chromatographed (silica gel, EtOAc/n-hexane=1/4) to afford a white solid (247 mg, 0.63 mmol, 60%).

Compounds 157-159, 165-168 and 171-173: Table 6 is a parameter table. "Parameter 1" was added into a reaction vessel for microwave-assisted heating and dissolved with "parameter 2" mL 2-propanol. "Parameter 3" was added thereinto, and stirred for 30 minutes. Pd(OAc)$_2$ "parameter 4", PPh$_3$ "parameter 5", 2 M Na$_2$CO$_{3(aq)}$ "parameter 6" and "parameter 7" mL H$_2$O were added and heated to 120° C. for 20 min using a microwave synthesizer. Before the temperature of the solution was decreased, "parameter 8" mL H$_2$O was added, and then cooled to room temperature, diluted with 10 mL EtOAc, and extracted with 10 mL H$_2$O. The organic layer was washed with 5% NaHCO$_{3(aq)}$ followed by brine, added in "parameter 9" mg Darco G-60, stirred for 10 min, filtered by the sintered glass funnel covered with about 1 cm of Celite and a thin layer of Florisil, concentrated, and purified by flash column chromatography (silica gel, "parameter 10") to obtain "parameter 11."

TABLE 6

The parameter table for the synthesis of compounds 157-159, 165-168 and 171-173

| | 157 | 158 | 159 | 165 | 166 |
|---|---|---|---|---|---|
| 1 | 2-fluorophenylboronic acid (58 mg, 0.41 mmol) | 2-chlorophenylboronic acid (55 mg, 0.35 mmol) | 2-methoxyphenylboronic acid (55 mg, 0.36 mmol) | 2-fluorophenyl boronic acid (55 mg, 0.39 mmol) | 2-chlorophenyl boronic acid (60 mg, 0.38 mmol) |
| 2 | 2 | 1.8 | 1.8 | 2 | 2 |
| 3 | C$_{19}$H$_{24}$BrNO$_2$ (102 mg, 0.27 mmol) | C$_{19}$H$_{24}$BrNO$_2$ (90 mg, 0.24 mmol) | C$_{19}$H$_{24}$BrNO$_2$ (89 mg, 0.24 mmol) | C$_{19}$H$_{21}$BrFNO2 (105 mg, 0.27 mmol) | C$_{19}$H$_{21}$BrFNO$_2$ (101 mg, 0.26 mmol) |
| 4 | 1.5 mg, 0.007 mmol | 1.6 mg, 0.007 mmol | 1.7 mg, 0.0076 mmol | 1.6 mg, 0.007 mmol | 1.4 mg, 0.006 mmol |
| 5 | 4.2 mg, 0.016 mmol | 8.0 mg, 0.03 mmol | 4.7 mg, 0.018 mmol | 6.0 mg, 0.023 mmol | 5.6 mg, 0.021 mmol |
| 6 | 0.20 mL, 0.40 mmol | 0.18 mL, 0.36 mmol | 0.18 mL, 0.36 mmol | 0.19 mL, 0.38 mmol | 0.19 mL, 0.38 mmol |
| 7 | 0.2 | 0.18 | 0.18 | 0.2 | 0.2 |
| 8 | 0.7 | 0.63 | 0.63 | 0.7 | 0.7 |
| 9 | 117 | 113 | 99 | 101 | 117 |
| 10 | 1/3 | 1/3 | 1/2 | 1/4 | 1/4 |
| 11 | beige yellow oil products (103 mg, 0.26 mmol, 97%) | light yellow oil products (58 mg, 0.14 mmol, 59%) | light yellow oil products (69 mg, 0.17 mmol, 71%) | yellow oil products (108 mg, 0.26 mmol, 99%) | light yellow oil products (50 mg, 0.12 mmol, 47%) |
| 12 | C$_{25}$H$_{26}$FNO$_2$ (103 mg, 0.26 mmol) | C$_{25}$H$_{26}$ClNO$_2$ (31 mg, 0.08 mmol) | C$_{26}$H$_{29}$NO$_3$ (69 mg, 0.17 mmol) | C$_{25}$H$_{25}$F$_2$NO$_2$ (108 mg, 0.26 mmol) | C$_{25}$H$_{25}$ClFNO$_2$ (50 mg, 0.12 mmol) |
| 13 | white solid products (113 mg, 0.26 mmol) | light yellow solid products (36 mg, 0.08 mmol) | light yellow solid products (66 mg, 0.15 mmol) | light yellow solid products (116 mg, 0.26 mmol) | beige white solid muriate products (55 mg, 0.12 mmol) |

| | 167 | 168 | 171 | 172 | 173 |
|---|---|---|---|---|---|
| 1 | 2-fluorophenylboronic acid (45 mg, 0.32 mmol) | 2-chlorophenylboronic acid (48 mg, 0.31 mmol) | 2-fluorophenylboronic acid (50 mg, 0.36 mmol) | 2-chlorophenyl boronic acid (56 mg, 0.36 mmol) | 2-methoxyphenylboronic acid (56 mg, 0.37 mmol) |
| 2 | 1.8 | 1.7 | 2 | 2 | 2 |
| 3 | C$_{19}$H$_{21}$BrClNO$_2$ (90 mg, 0.22 mmol) | C$_{19}$H$_{21}$BrClNO$_2$ (84 mg, 0.20 mmol) | C$_{19}$H$_{22}$BrN$_2$O$_4$ (98 mg, 0.23 mmol) | C$_{19}$H$_{22}$BrN$_2$O$_4$ (100 mg, 0.24 mmol) | C$_{19}$H$_{22}$BrN$_2$O$_4$ (101 mg, 0.24 mmol) |
| 4 | 2.0 mg, 0.009 mmol | 1.0 mg, 0.004 mmol | 1.7 mg, 0.0076 mmol | 1.8 mg, 0.0072 mmol | 1.8 mg, 0.008 mmol |
| 5 | 4.7 mg, 0.02 mmol | 4.4 mg, 0.02 mmol | 5.7 mg, 0.022 mmol | 6.0 mg, 0.023 mmol | 6.5 mg, 0.025 mmol |
| 6 | 0.19 mL, 0.38 mmol | 0.16 mL, 0.32 mmol | 0.18 mL, 0.36 mmol | 0.18 mL, 0.36 mmol | 0.18 mL, 0.36 mmol |
| 7 | 0.2 | 0.17 | 0.2 | 0.2 | 0.2 |
| 8 | 0.7 | 0.6 | 0.7 | 0.7 | 0.7 |
| 9 | 105 | 90 | 112 | 101 | 115 |
| 10 | 1/3 | 1/3 | 1/1 | 1/2 | 1/1 |
| 11 | yellow oil products (91 mg, 0.21 mmol, 97%) | beige yellow solid products (66 mg, 0.15 mmol, 73%) | beige solid products (75 mg, 0.17 mmol, 71%) | beige white solid products (72 mg, 0.16 mmol, 66%) | beige yellow solid products (88 mg, 0.20 mmol, 81%) |

TABLE 6-continued

The parameter table for the synthesis of compounds 157-159, 165-168 and 171-173

| 12 | $C_{25}H_{25}ClFNO_2$ (91 mg, 0.21 mmol) | $C_{25}H_{25}Cl_2NO_2$ (66 mg, 0.15 mmol) | $C_{25}H_{25}FN_2O_4$ (56 mg, 0.13 mmol) | $C_{25}H_{25}ClN_2O_4$ (72 mg, 0.16 mmol) | $C_{26}H_{28}N_2O_5$ (72 mg, 0.16 mmol) |
|---|---|---|---|---|---|
| 13 | light yellow solid products (94 mg, 0.20 mmol) | beige solid products (72 mg, 0.15 mmol) | beige white solid products (61 mg, 0.13 mmol) | beige yellow solid products (81 mg, 0.17 mmol) | beige white solid products (80 mg, 0.16 mmol) |

TABLE 7

The analytical data of the compounds in this invention

Compound number 7

| | |
|---|---|
| Name | 6-Methoxy-8-(2-methoxyphenyl)-2-(3-(4-nitrophenyl)propyl)-1,2,3,4-tetrahydroisoquinolin-7-ol |
| $^1$H NMR (200 MHz, CDCl$_3$) | 1.69-1.90 (m, 2H), 2.29-2.45 (m, 2H), 2.60-2.78 (m, 4H), 2.83-2.96 (m, 2H), 3.11 (d, J = 15.2 Hz, 1H), 3.19 (d, J = 15.2 Hz, 1H), 3.75 (s, 3H), 3.88 (s, 3H), 5.37 (bs, 1H), 6.64 (s, 1H), 6.96-7.09 (m, 2H), 7.14 (dd, J = 7.3, 1.9 Hz, 1H), 7.22-7.32 (m, 2H), 7.32-7.43 (m, 1H), 8.05-8.16 (m, 2H) |
| $^{13}$C NMR (50 MHz, CDCl$_3$) | 28.4, 29.4, 33.5, 50.6, 54.2, 55.8, 56.0, 57.0, 110.3, 111.4, 121.0, 122.7, 123.7, 124.2, 125.2, 126.2, 129.3, 131.6, 141.2, 145.2, 146.4, 150.4, 157.1 |
| ESI-MS | m/z 449 ([M + H]$^+$) |
| EIHR-MS | calcd for $C_{26}H_{29}N_2O_5$ [M + H]$^+$, 449.2076; found, 449.2087 |

Compound number 8

| | |
|---|---|
| Name | 6-Methoxy-8-(2-methoxyphenyl)-2-(3-(pyridin-4-yl)propyl)-1,2,3,4-tetrahydroisoquinolin-7-ol |
| $^1$H NMR (200 MHz, CDCl$_3$) | 1.66-1.87 (m, 2H), 2.29-2.44 (m, 2H), 2.51-2.73 (m, 4H), 2.89 (t, J = 5.8 Hz, 2H), 3.15 (dd, J = 17.1, 15.3 Hz, 2H), 3.74 (s, 3H), 3.87 (s, 3H), 5.47 (s, 1H), 6.63 (s, 1H), 6.94-7.09 (m, 4H), 7.14 (dd, J = 7.4, 2.0 Hz, 1H), 7.30-7.44 (m, 1H), 8.44 (dd, J = 4.4, 1.6 Hz, 2H) |
| 13C NMR (50 MHz, CDCl$_3$) | 27.7, 29.3, 32.9, 50.6, 54.2, 55.8, 56.0, 57.1, 110.3, 111.4, 120.9, 122.8, 124.0, 124.2, 125.2, 126.3, 129.4, 131.6, 141.2, 145.3, 149.7, 151.4, 157.1 |
| ESIHRMS | calcd for $C_{25}H_{29}N_2O_3$ [M + H]$^+$, 405.2178; found, 405.2170 |

Compound number 9

| | |
|---|---|
| Name | 6-Methoxy-8-(2-methoxyphenyl)-2-(3-(pyridin-3-yl)propyl)-1,2,3,4-tetrahydroisoquinolin-7-ol |
| $^1$H NMR (200 MHz, CDCl$_3$) | 1.65-1.87 (m, 2H), 2.30-2.46 (m, 2H), 2.50-2.75 (m, 4H), 2.89 (t, J = 5.7 Hz, 2H), 3.16 (s, 2H), 3.74 (s, 3H), 3.78 (s, 3H), 6.63 (s, 1H), 6.91-7.09 (m, 2H), 7.09-7.22 (m, 2H), 7.29-7.49 (m, 2H), 8.32-8.46 (m, 2H) |
| $^{13}$C NMR (50 MHz, CDCl$_3$) | 28.5, 29.3, 30.7, 50.6, 54.2, 55.7, 56.0, 57.2, 110.3, 111.4, 120.9, 122.8, 123.4, 124.2, 125.2, 126.3, 129.4, 131.6, 135.9, 137.5, 141.2, 145.3, 147.3, 150.0, 157.1 |
| ESIHRMS | calcd for $C_{25}H_{29}N_2O_3$ [M + H]$^+$, 405.2178; found, 405.2170 |

Compound number 10

| | |
|---|---|
| Name | 6,7-dimethoxy-8-(2-methoxyphenyl)-2-(3-(pyridin-4-yl)propyl)-1,2,3,4-tetrahydroisoquinoline |
| $^1$H NMR (200 MHz, CDCl$_3$) | 1.74-1.80 (m, 2H), 2.37 (t, J = 7.3 Hz, 2H), 2.59 (t, J = 7.7 Hz, 2H), 2.63-2.72 (m, 2H), 2.92 (t, J = 5.8 Hz, 2H), 3.12 (q, J = 14.8 Hz, 2H), 3.52 (s, 3H), 3.73 (s, 3H), 3.85 (s, 3H), 6.69 (s, 1H), 7.00 (q, J = 8.5 Hz, 2H), 7.06 (d, J = 5.8 Hz, 2H), 7.09 (dd, J = 7.4, 1.8 Hz, 2H), 7.36 (dt, J = 7.8, 1.8 Hz, 1H), 8.45 (d, J = 5.7 Hz, 2H) |
| $^{13}$C NMR (50 MHz, CDCl$_3$) | 27.7, 29.5, 32.8, 50.3, 54.1, 55.5, 55.8, 57.0, 60.6, 110.8, 111.8, 120.5, 124.0 (2C), 125.2, 126.2, 128.9, 129.6 (2C), 131.1, 145.0, 149.7 (2C), 150.9, 151.3, 156.9 |
| ESIHRMS | calcd for $C_{26}H_{31}N_2O_3$ [M + H]$^+$, 419.2335; found, 419.2317 |

Compound number 11

| | |
|---|---|
| Name | 2-(2-Fluorophenethyl)-6-methoxy-1,2,3,4-tetrahydroisoquinolin-7-ol |
| $^1$H NMR (200 MHz, CDCl$_3$) | 2.68-2.89 (m, 6H), 2.89-3.01 (m, 2H), 3.61 (s, 2H), 3.83 (s, 3H), 6.56 (s, 2H), 6.94-7.11 (m, 2H), 7.12-7.30 (m, 2H) |
| $^{13}$C NMR (50 MHz, CDCl$_3$) | 27.2, 28.8, 51.1, 55.5, 56.0, 58.6, 110.8, 112.5, 115.4 (J = 22.1 Hz), 124.1 (J = 3.1 Hz), 125.5, 127.2 (J = 15.9 Hz), 127.3, 127.9 (J = 7.9 Hz), 131.1 (J = 4.8 Hz), 143.8, 145.4, 161.3 (J = 243 Hz) |
| ESI-MS | m/z 302 ([M + H]$^+$) |
| EIHR-MS | calcd for $C_{18}H_{21}FNO_2$ [M + H]$^+$, 302.1556; found, 302.1554 |

Compound number 12

| | |
|---|---|
| Name | 6-Methoxy-2-(3-(4-nitrophenyl)propyl)-1,2,3,4-tetrahydroisoquinolin-7-ol |
| $^1$H NMR (200 MHz, CDCl$_3$) | 1.84-2.05 (m, 2H), 2.44-2.56 (m, 2H), 2.63-2.74 (m, 2H), 2.74-2.88 (m, 4H), 3.50 (s, 2H), 3.83 (s, 3H), 6.54 (s, 1H), 6.56 (s, 1H), 7.30-7.42 (m, 2H), 8.09-8.20 (m, 2H) |
| $^{13}$C NMR (50 MHz, CDCl$_3$) | 28.4, 28.8, 33.6, 51.2, 55.6, 56.0, 57.3, 110.8, 112.4, 123.7, 125.5, 127.2, 129.4, 143.8, 145.4, 146.4, 150.3 |
| EIHR-MS | calcd for $C_{19}H_{23}N_2O_4$ [M + H]$^+$, 343.1658; found, 343.1661 |

Compound number 15

| | |
|---|---|
| Name | 8-Bromo-6-methoxy-2-(3-(4-nitrophenyl)propyl)-1,2,3,4-tetrahydroisoquinolin-7-ol |
| $^1$H NMR (200 MHz, CDCl$_3$) | 1.87-2.06 (m, 2H), 2.49-2.74 (m, 4H), 2.74-2.90 (m, 4H), 3.53 (s, 2H), 3.85 (s, 3H), 6.57 (s, 1H), 7.31-7.43 (m, 2H), 8.07-8.21 (m, 2H) |
| $^{13}$C NMR (50 MHz, CDCl$_3$) | 28.4, 29.3, 33.6, 50.4, 56.2, 56.4, 57.2, 109.0, 110.1, 123.8, 126.4, 127.2, 129.4, 141.3, 145.6, 146.4, 150.2 |
| ESI-MS | m/z 421 ([M + H]$^+$) |
| EIHR-MS | calcd for $C_{19}H_{22}BrN_2O_4$ [M + H]$^+$, 421.0763; found, 421.0757 |

Compound number 21

| | |
|---|---|
| Name | 6-Methoxy-2-phenethyl-1,2,3,4-tetrahydroisoquinolin-7-ol |
| $^1$H NMR (200 MHz, CDCl$_3$) | 2.71-2.96 (m, 8H), 3.61 (s, 2H), 3.84 (s, 3H), 6.57 (s, 2H), 7.16-7.34 (m, 5H) |

TABLE 7-continued

The analytical data of the compounds in this invention

| | |
|---|---|
| $^{13}$C NMR (50 MHz, CDCl$_3$) | 28.8, 34.1, 51.2, 55.6, 56.0, 60.4, 110.8, 112.4, 125.5, 126.2, 127.3, 128.5, 128.9, 140.5, 143.8, 145.4 |

Compound number 29

| | |
|---|---|
| Name | 6-Methoxy-8-(2-methoxyphenyl)-2-phenethyl-1,2,3,4-tetrahydroisoquinolin-7-ol |
| $^1$H NMR (200 MHz, CDCl$_3$) | 2.57-2.66 (m, 2H), 2.72-2.81 (m, 4H), 2.85-2.92 (m, 2H), 3.25 (s, 2H), 3.74 (s, 3H), 3.86 (s, 3H), 6.63 (s, 1H), 6.97-7.06(m, 2H), 7.11-7.28(m, 6H), 7.32-7.40 (m, 1H) |
| $^{13}$C NMR (50 MHz, CDCl$_3$) | 29.2, 34.0, 50.5, 54.2, 55.7, 56.0, 60.0, 110.2, 111.3, 120.9, 122.8, 124.1, 125.2, 126.0, 126.2, 128.4, 128.7, 129.3, 131.6, 140.5, 141.1, 145.2, 157.1 |
| ESI-MS | m/z 390 ([M + H]$^+$) |
| EIHR-MS | calcd for C$_{25}$H$_{28}$NO$_3$ [M + H]$^+$, 390.2069; found, 390.2054 |

Compound number 30

| | |
|---|---|
| Name | 6-Methoxy-8-(4-methoxyphenyl)-2-phenethyl-1,2,3,4-tetrahydroisoquinolin-7-ol |
| $^1$H NMR (200 MHz, CDCl$_3$) | 2.59-2.68 (m, 2H), 2.73-2.82 (m, 4H), 2.92, (t, J = 5.8 Hz, 2H), 3.29 (s, 2H), 3.83 (s, 3H), 3.87 (s, 3H), 6.62 (s, 1H), 6.93-6.94 (m, 1H), 6.98-6.99 (m, 1H), 7.12-7.24 (m, 7H) |
| $^{13}$C NMR (50 MHz, CDCl$_3$) | 29.4, 34.0, 50.6, 55.0, 55.3, 56.1, 60.2, 110.0, 114.1, 125.4, 125.9, 126.0, 127.6, 128.4, 128.7, 130.9, 140.4, 141.2, 145.4, 158.9 |
| ESI-MS | m/z 390 ([M + H]$^+$), 412 ([M + Na]$^+$) |
| EIHR-MS | calcd for C$_{25}$H$_{28}$NO$_3$ [M + H]$^+$, 390.2069; found, 390.2067 |

Compound number 31

| | |
|---|---|
| Name | 6-Methoxy-8-(3-methoxyphenyl)-2-phenethyl-1,2,3,4-tetrahydroisoquinolin-7-ol |
| $^1$H NMR (200 MHz, CDCl$_3$) | 2.59-2.68 (m, 2H), 2.74-2.80 (m, 4H), 2.89-2.95 (m, 2H), 3.31 (s, 2H), 3.78 (s, 3H), 3.86 (s, 3H), 6.63 (s, 1H), 6.78-6.83 (m, 2H), 6.86-6.94 (m, 1H), 7.11-7.24 (m, 5H), 7.30-7.40 (m. 1H) |
| $^{13}$C NMR (50 MHz, CDCl$_3$) | 29.2, 33.8, 50.4, 54.7, 55.2, 56.0, 60.0, 110.1, 113.3, 115.2, 122.1, 125.3, 125.4, 126.1, 126.2, 128.4, 128.7, 129.6, 136.9, 140.3, 141.0, 145.4, 159.7 |
| ESI-MS | m/z 390.2 ([M + H]$^+$), 412.2 ([M + Na]$^+$) |
| EIHR-MS | calcd for C$_{25}$H$_{28}$NO$_3$ [M + H]$^+$, 390.2069; found, 390.2064 |

Compound number 32

| | |
|---|---|
| Name | 6-Methoxy-8-(3,4,5-trimethoxyphenyl)-2-phenethyl-1,2,3,4-tetrahydroisoquinolin-7-ol |
| $^1$H NMR (200 MHz, CDCl$_3$) | 2.62-2.71 (m, 2H), 2.78-2.85 (m, 4H), 2.91-2.96 (m, 2H), 3.32 (s, 2H), 3.90 (s, 6H), 3.91 (s, 3H), 3.92 (s, 3H), 5.41 (s, 1H), 6.46 (s, 2H), 6.65 (s, 1H), 7.13-7.30 (m, 5H) |
| $^{13}$C NMR (50 MHz, CDCl$_3$) | 29.5, 34.1, 50.5, 54.5, 56.2, 60.3, 61.0, 106.6, 110.3, 125.7, 126.2, 126.3, 128.5, 128.8, 131.0, 137.1, 140.3, 140.9, 145.4, 153.5 |
| ESI-MS | m/z 449 ([M]$^+$) |
| EIHR-MS | calcd for C$_{27}$H$_{32}$NO$_5$ [M + H]$^+$, 450.2280; found, 450.2268 |

Compound number 33

| | |
|---|---|
| Name | 6-Methoxy-2-phenethyl-8-phenyl-1,2,3,4-tetrahydroisoquinolin-7-ol |
| $^1$H NMR (200 MHz, CDCl$_3$) | 2.57-2.66 (m, 2H), 2.72-2.79 (m, 4H), 2.89-2.94 (m, 2H), 3.28 (s, 2H), 3.85 (s, 3H), 6.63 (s, 1H), 7.10-7.14 (m, 2H), 7.19-7.25 (m, 5H), 7.32-7.48 (m, 3H) |
| $^{13}$C NMR (50 MHz, CDCl$_3$) | 29.3, 33.9, 50.5, 54.9, 56.1, 60.1, 110.1, 125.4, 126.1, 126.4, 127.5, 128.4, 128.6, 128.7, 129.8, 135.7, 140.3, 141.0, 145.4 |
| ESI-MS | m/z 360 ([M + H]$^+$) |
| EIHR-MS | calcd for C$_{24}$H$_{26}$NO$_2$ [M + H]$^+$, 360.1964; found, 360.1956 |

Compound number 34

| | |
|---|---|
| Name | 6-Methoxy-8-(2-methylthiophenyl)-2-phenethyl-1,2,3,4-tetrahydroisoquinolin-7-ol |
| $^1$H NMR (200 MHz, CDCl$_3$) | 2.37 (s, 3H), 2.57-2.66 (m, 2H), 2.72-2.81 (m, 4H), 2.89-2.92 (m, 2H), 3.22 (s, 2H), 3.88 (s, 3H), 6.67 (s, 1H), 7.12-7.22 (m, 8H), 7.25-7.29 (m, 1H) |
| $^{13}$C NMR (50 MHz, CDCl$_3$) | 15.2, 29.2, 34.0, 50.5, 53.8, 56.0, 60.0, 110.6, 124.1, 124.7, 125.0, 125.6, 125.9, 126.1, 128.4, 128.6, 128.8, 130.1, 133.9, 138.6, 140.5, 141.0, 145.2 |
| ESI-MS | m/z 406 ([M + H]$^+$) |
| EIHR-MS | calcd for C$_{25}$H$_{28}$NO$_2$S [M + H]$^+$, 406.1841; found, 406.1836 |

Compound number 35

| | |
|---|---|
| Name | 6-Methoxy-8-(4-methylthiophenyl)-2-phenethyl-1,2,3,4-tetrahydroisoquinolin-7-ol |
| $^1$H NMR (200 MHz, CDCl$_3$) | 2.51 (s, 3H), 2.63-2.68 (m, 2H), 2.74-2.81 (m, 4H), 2.89-2.95 (m, 2H), 3.29 (s, 2H), 3.88 (s, 3H), 6.63 (s, 1H), 7.14-7.21 (m, 6H), 7.25-7.33 (m, 3H) |
| $^{13}$C NMR (50 MHz, CDCl$_3$) | 15.7, 29.4, 33.9, 50.5, 55.0, 56.1, 60.2, 110.1, 125.5, 125.6, 126.1, 126.5, 128.4, 128.8, 130.3, 137.6, 140.4, 141.1, 145.4 |
| ESI-MS | 406 ([M + H]$^+$) |
| EIHR-MS | calcd for C$_{25}$H$_{28}$NO$_2$S [M + H]$^+$, 406.1841; found, 406.1839 |

Compound number 36

| | |
|---|---|
| Name | 8-(Benzo[1,3]dioxol-5-yl)-6-methoxy-2-phenethyl-1,2,3,4-tetrahydroisoquinolin-7-ol |
| $^1$H NMR (200 MHz, CDCl$_3$) | 2.61-2.70 (m, 2H), 2.73-2.84 (m, 4H), 2.89-2.94 (m, 2H), 3.30 (s, 2H), 3.88 (s, 3H), 5.43 (bs, 1H), 6.00 (bs, 2H), 6.63 (s, 1H), 6.68-6.73 (m, 2H), 6.86-6.90 (m, 1H), 7.16-7.26 (m, 5H) |
| $^{13}$C NMR (50 MHz, CDCl$_3$) | 29.5, 34.1, 50.6, 55.0, 56.2, 60.3, 101.2, 108.7, 110.1, 110.4, 123.1, 125.5, 125.9, 126.1, 128.5, 128.8, 129.0, 140.4, 141.2, 145.3, 147.0, 147.8 |
| ESI-MS | m/z 404 ([M + H]$^+$) |
| EIHR-MS | calcd for C$_{25}$H$_{26}$NO$_4$ [M + H]$^+$, 404.1862; found, 404.1849 |

Compound number 37

| | |
|---|---|
| Name | 8-(2-Cyanophenyl)-6methoxy-2-phenethyl-1,2,3,4-tetrahydroisoquinolin-7-ol |
| $^1$H NMR (200 MHz, CDCl$_3$) | 2.61-2.80 (m, 6H), 2.87-2.94 (m, 2H), 3.12 (d, J = 14.8 Hz, 1H), 3.32 (d, J = 14.9 Hz, 1H), 3.90 (s, 3H), 6.68 (s, 1H), 7.12-7.29 (m, 5H), 7.35 (ddd, J = 7.7, 1.3, 0.6 Hz, 1H), 7.46 (td, J = 7.6, 1.3 Hz, 1H), 7.65 (td, J = 7.6, 1.5 Hz, 1H), 7.77 (ddd, J = 7.7, 1.4, 0.5 Hz, 1H) |
| $^{13}$C NMR (50 MHz, CDCl$_3$) | 29.2, 34.0, 50.3, 54.3, 56.1, 60.0, 111.2, 114.0, 118.2, 122.2, 125.1, 126.0, 126.2, 128.1, 128.5, 128.8, 131.0, 132.8, 133.2, 140.3, 141.3, 145.3 |
| ESI-MS | m/z 385 ([M + H]$^+$) |
| EIHR-MS | calcd for C$_{25}$H$_{25}$N$_2$O$_2$ [M + H]$^+$, 385.1916; found, 385.1910 |

Compound number 38

| | |
|---|---|
| Name | 6-Methoxy-8-(2-nitrophenyl)-2-phenethyl-1,2,3,4-tetrahydroisoquinolin-7-ol |

TABLE 7-continued

The analytical data of the compounds in this invention

| | |
|---|---|
| $^1$H NMR (200 MHz, CDCl$_3$) | 2.63-2.82 (m, 6H), 2.87-2.91 (m, 2H), 3.14 (d, J = 15.0 Hz, 1H), 3.40 (d, J = 14.9 Hz, 1H), 3.87 (s, 3H), 6.65 (s, 1H), 7.12-7.26 (m, 5H), 7.30-7.36 (m, 1H), 7.48-7.58 (m, 1H), 7.60-7.70 (m, 1H), 8.01-8.08 (m, 1H) |
| $^{13}$C NMR (50 MHz, CDCl$_3$) | 28.9, 33.9, 50.3, 54.0, 56.1, 59.7, 110.6, 121.9, 124.6, 124.8, 125.8, 126.2, 128.5, 128.8, 131.0, 132.6, 133.1, 140.3, 140.7, 145.0, 149.6 |
| ESI-MS | m/z 405 ([M + H]$^+$) |
| EIHR-MS | calcd for C$_{24}$H$_{25}$N$_2$O$_4$ [M + H]$^+$, 405.1814; found, 405.1800 |

Compound number
39

| | |
|---|---|
| Name | 8-(2-Chlorophenyl)-6-methoxy-2-phenethyl-1,2,3,4-tetrahydroisoquinolin-7-ol |
| $^1$H NMR (200 MHz, CDCl$_3$) | 2.59-2.69 (m, 2H), 2.72-2.82 (m, 4H), 2.88-2.91 (m, 2H), 3.21 (d, J = 3.7 Hz, 2H), 3.85 (s, 3H), 6.65 (s, 1H), 7.11-7.22 (m, 6H), 7.28-7.33 (m 2H), 7.43-7.52 (m, 1H) |
| $^{13}$C NMR (50 MHz, CDCl$_3$) | 29.1, 33.9, 50.4, 53.9, 56.0, 59.9, 110.5, 123.6, 125.4, 125.6, 126.0, 127.0, 128.4, 128.7, 129.1, 129.7, 131.5, 134.1, 134.9, 140.4, 141.1, 145.2 |
| ESI-MS | m/z 394 ([M + H]$^+$) |
| EIHR-MS | calcd for C$_{24}$H$_{25}$ClNO$_2$ [M + H]$^+$, 394.1574; found, 394.1571 |

Compound number
40

| | |
|---|---|
| Name | 8-(2-Acetylphenyl)-6methoxy-2-phenethyl-1,2,3,4-tetrahydroisoquinolin-7-ol |
| $^1$H NMR (200 MHz, CDCl$_3$) | 2.15 (s, 3H), 2.53-3.00 (m, 8H), 3.05 (d, J = 15.4 Hz, 1H), 3.28 (d, J = 15.1 Hz, 1H), 3.87 (s, 3H), 5.59 (bs, 1H), 6.65 (s, 1H), 7.06-7.61 (m, 8H), 7.76 (dd, J = 7.5, 1.6 Hz, 1H) |
| ESI-MS | m/z 402 ([M + H]$^+$) |
| EIHR-MS | calcd for C$_{26}$H$_{28}$NO$_3$ [M + H]$^+$, 402.2069; found, 402.2061 |

Compound number
41

| | |
|---|---|
| Name | 8-(2-Fluorophenyl)-6-methoxy-2-phenethyl-1,2,3,4-tetrahydroisoquinolin-7-ol |
| $^1$H NMR (200 MHz, CDCl$_3$) | 2.61-2.68 (m, 2H), 2.72-2.84 (m, 4H), 2.88-2.92 (m, 2H), 3.23 (d, J = 15.0 Hz, 1H), 3.37 (d, J = 15.0 Hz, 1H), 3.89 (s, 3H), 5.52 (s, 1H), 6.67 (s, 1H), 7.12-7.35 (m, 9H) |
| $^{13}$C NMR (50 MHz, CDCl$_3$) | 29.3, 34.0, 50.5, 54.3, 56.1, 60.1, 110.7, 115.9 (d, J = 22.3 Hz), 119.7, 123.1 (d, J = 17.7 Hz), 124.2, 125.6, 126.1, 128.4, 128.8, 129.7 (d, J = 7.9 Hz), 132.0, 140.1, 141.5, 145.2, 160.1 (d, J = 244 Hz) |
| ESI-MS | m/z 378.2 ([M + H]$^+$) |

Compound number
42

| | |
|---|---|
| Name | (2-Methylphenyl)-6-methoxy-2-phenethyl-1,2,3,4-tetrahydroisoquinolin-7-ol |
| $^1$H NMR (200 MHz, CDCl$_3$) | 2.09 (s, 3H), 2.57-2.65 (m, 2H), 2.71-2.81 (m, 4H), 2.90-2.92 (m, 2H), 3.02 (d, J = 15.3 Hz, 1H), 3.25 (d, J = 15.2 Hz, 1H), 3.89 (s, 3H), 5.33 (s, 1H), 6.64 (s, 1H), 7.09-7.31 (m, 9H) |
| $^{13}$C NMR (50 MHz, CDCl$_3$) | 19.7, 29.4, 33.9, 50.6, 54.6, 56.1, 60.2, 110.0, 125.5, 125.6, 126.1, 128.0, 128.4, 128.8, 129.8, 130.3, 135.0, 137.0, 140.4, 140.7, 145.3 |
| ESI-MS | m/z 374.2 ([M + H]$^+$) |

Compound number
43

| | |
|---|---|
| Name | 8-(2-Isopropylphenyl)-6-methoxy-2-phenethyl-1,2,3,4-tetrahydroisoquinolin-7-ol |
| $^1$H NMR (200 MHz, CDCl$_3$) | 1.12-1.17 (m, 3H), 1.26-1.30 (m, 3H), 2.65-2.94 (m, 8H), 3.12-3.20 (m, 2H), 3.63-3.65 (m, 1H), 3.91 (s, 3H), 5.30 (s, 1H), 6.67 (s, 1H), 7.06-7.42 (m, 9H) |
| $^{13}$C NMR (50 MHz, CDCl$_3$) | 24.0, 24.5, 29.3, 30.3, 33.9, 50.7, 54.7, 56.0, 60.2, 110.0, 125.5, 125.8, 126.1, 128.4, 128.7, 128.9, 129.9, 133.5, 140.3, 141.0, 145.2, 147.7 |
| ESI-MS | m/z 402.2 ([M + H]$^+$) |

Compound number
44

| | |
|---|---|
| Name | 8-(3,5-Dimethoxyphenyl)-6-methoxy-2-phenethyl-1,2,3,4-tetrahydroisoquinolin-7-ol |
| $^1$H NMR (200 MHz, CDCl$_3$) | 2.58-2.72 (m, 2H), 2.73-2.82 (m, 4H), 2.93 (t, J = 3.0 Hz, 2H), 3.33 (s, 2H), 3.79 (s, 6H), 3.90 (s, 3H), 5.36 (s, 1H), 6.40 (s, 1H), 6.41 (s, 1H), 6.64 (s, 1H), 6.46-6.50 (m, 1H), 7.11-7.23 (m, 4H), 7.27-7.32 (m, 1H) |
| $^{13}$C NMR (50 MHz, CDCl$_3$) | 29.5, 34.1, 50.6, 54.8, 55.5, 56.2, 60.2, 100.0, 107.6, 110.3, 125.6, 126.1, 126.3, 128.5, 128.8, 137.5, 140.4, 140.8, 145.4, 161.0 |
| ESI-MS | m/z 420 ([M + H]$^+$) |
| EIHR-MS | calcd for C$_{26}$H$_{30}$NO$_4$ [M + H]$^+$, 420.2175; found, 420.2167 |

Compound number
45

| | |
|---|---|
| Name | 8-(2,3-Dimethoxyphenyl)-6-methoxy-2-phenethyl-1,2,3,4-tetrahydroisoquinolin-7-ol |
| $^1$H NMR (200 MHz, CDCl$_3$) | 2.54-2.86 (m, 6H), 2.87-3.00 (m, 2H), 3.28 (s, 2H), 3.62 (s, 3H), 3.89 (s, 3H), 3.90 (s, 3H), 5.46 (s, 1H), 6.65 (s, 1H), 6.73 (dd, J = 7.6, 1.5 Hz, 1H), 6.95 (dd, J = 8.2, 1.4 Hz, 1H), 7.07-7.29 (m, 6H) |
| $^{13}$C NMR (50 MHz, CDCl$_3$) | 29.3, 33.9, 50.6, 54.2, 55.8, 56.0, 60.0, 60.8, 110.2, 112.0, 122.6, 123.1, 124.3, 125.3, 126.0, 126.2, 128.4, 128.8, 129.7, 140.5, 140.9, 145.1, 147.0, 153.1 |
| ESI-MS | m/z 420 ([M + H]$^+$) |
| EIHR-MS | calcd for C$_{26}$H$_{30}$NO$_4$ [M + H]$^+$, 420.2175; found, 420.2159 |

Compound number
60

| | |
|---|---|
| Name | 8-Bromo-6-methoxy-2-phenethyl-1,2,3,4-tetrahydroisoquinolin-7-ol |
| $^1$H NMR (200 MHz, CDCl$_3$) | 2.70-3.01 (m, 8H), 3.64 (s, 2H), 3.86 (s, 3H), 6.58 (s, 1H), 7.17-7.37 (m, 5H) |
| $^{13}$C NMR (50 MHz, CDCl$_3$) | 29.3, 34.0, 50.4, 56.2, 56.4, 60.2, 109.0, 110.1, 126.2, 126.5, 127.3, 128.6, 128.9, 140.3, 141.2, 145.6 |
| ESI-MS | calcd for C$_{18}$H$_{21}$BrNO$_2$ m/z 362.1 |
| EIHR-MS | calcd for C$_{18}$H$_{21}$BrNO$_2$ [M + H]$^+$, 362.0755; found, 362.0782 |

Compound number
61

| | |
|---|---|
| Name | 6-Methoxy-2-(2-(1-naphthyl)ethyl)-1,2,3,4-tetrahydroisoquinolin-7-ol |
| $^1$H NMR (200 MHz, CDCl$_3$) | 2.68-2.97 (m, 6H), 3.23-3.47 (m, 2H), 3.68 (s, 2H), 3.83 (s, 3H), 6.58 (s, 1H), 6.60 (s, 1H), 7.28-7.58 (m, 4H), 7.64-7.91 (m, 2H), 8.00-8.17 (m, 1H) |
| $^{13}$C NMR (50 MHz, CDCl$_3$) | 28.8, 31.1, 51.3, 55.6, 56.0, 59.4, 110.8, 112.6, 123.9, 125.4, 125.6, 125.7, 126.1, 126.7, 127.0, 127.1, 128.9, 132.0, 134.0, 136.5, 144.0, 145.6 |
| EIHR-MS | calcd for C$_{22}$H$_{23}$NO$_2$ [M]$^+$, 333.1729; found, 333.1721 |

Compound number
62

| | |
|---|---|
| Name | 2-(2-(3-indolyl)ethyl)-6-methoxy-1,2,3,4-tetrahydroisoquinolin-7-ol |
| $^1$H NMR (200 MHz, CDCl$_3$) | 2.76-2.94 (m, 6H), 3.00-3.15 (m, 2H), 3.66 (s, 2H), 3.85 (s, 3H), 6.59 (s, 1H), 6.61 (s, 1H), 7.02-7.24 (m, 3H), 7.32-7.40 (m, 1H), 7.61-7.69 (m, 1H), 8.03 (s, 1H) |

TABLE 7-continued

The analytical data of the compounds in this invention

| | |
|---|---|
| $^{13}$C NMR (50 MHz, CDCl$_3$) | 23.2, 28.7, 51.1, 55.5, 55.9, 58.9, 110.7, 111.1, 112.3, 114.4, 118.8, 119.2, 121.5, 121.9, 125.5, 127.3, 127.5, 136.2, 143.7, 145.3 |
| EIHR-MS | calcd for C$_{20}$H$_{22}$N$_2$O$_2$ [M]$^+$, 322.1681; found, 322.1675 |

| Compound number | 63 |
|---|---|
| Name | 6-Methoxy-2-(2-nitrophenethyl)-1,2,3,4-tetrahydroisoquinolin-7-ol |
| $^1$H NMR (200 MHz, CDCl$_3$) | 2.78-2.86 (m, 6H), 3.16-3.23 (m, 2H), 3.63 (s, 2H), 3.85 (s, 3H), 6.58 (s, 1H), 6.59 (s, 1H), 7.36-7.44 (m, 2H), 7.49-7.53 (m, 1H), 7.92 (dd, J = 8.1, 1.3 Hz, 1H) |
| $^{13}$C NMR (50 MHz, CDCl$_3$) | 28.9, 31.0, 50.9, 55.5, 56.1, 58.8, 110.8, 112.4, 125.6, 127.4, 132.7, 133.2, 135.5, 143.8, 145.4, 149.6 |
| ESI-MS | m/z 329.2 ([M + H]$^+$), 351.1 ([M + Na]$^+$) |

| Compound number | 64 |
|---|---|
| Name | 6-Methoxy-2-(3-nitrophenethyl)-1,2,3,4-tetrahydroisoquinolin-7-ol |
| $^1$H NMR (200 MHz, CDCl$_3$) | 2.73-2.89 (m, 6H), 2.95-3.03 (m, 2H), 3.58 (s, 2H), 3.82 (s, 3H), 5.73 (s, 1H), 6.55 (s, 1H), 7.42 (t, J = 7.8 Hz, 1H), 7.52 (d, J = 7.6 Hz, 1H), 8.03-8.09 (m, 2H) |
| $^{13}$C NMR (50 MHz, CDCl$_3$) | 28.8, 33.6, 51.2, 55.6, 56.1, 59.4, 110.8, 112.4, 121.4, 123.7, 125.5, 127.0, 129.4, 135.3, 142.5, 143.9, 145.5, 148.4 |
| ESI-MS | m/z 329.2 ([M + H]$^+$), 351.1 ([M + Na]$^+$) |

| Compound number | 65 |
|---|---|
| Name | 6-Methoxy-2-(4-nitrophenethyl)-1,2,3,4-tetrahydroisoquinolin-7-ol |
| $^1$H NMR (200 MHz, CDCl$_3$) | 2.74-2.86 (m, 6H), 2.97-3.04 (m, 2H), 3.60 (s, 2H), 3.85 (s, 3H), 6.57 (s, 2H), 7.36-7.43 (m, 2H), 8.11-8.18 (m, 2H) |
| $^{13}$C NMR (50 MHz, CDCl$_3$) | 28.8, 33.9, 51.2, 55.6, 56.1, 59.3, 110.8, 112.4, 123.8, 125.5, 127.0, 129.7, 143.9, 145.5, 146.6, 148.5 |
| ESI-MS | ESIMS m/z 329.1 ([M + H]$^+$) |

| Compound number | 66 |
|---|---|
| Name | 2-(4-Chlorophenethyl)-6-methoxy-1,2,3,4-tetrahydroisoquinolin-7-ol |
| $^1$H NMR (200 MHz, CDCl$_3$) | 2.66-2.93 (m, 8H), 3.58 (s, 2H), 3.83 (s, 3H), 6.54 (s, 1H), 6.56 (s, 1H), 7.11-7.19 (m, 2H), 7.21-7.28 (m, 2H) |
| $^{13}$C NMR (50 MHz, CDCl$_3$) | 28.7, 33.3, 51.2, 55.5, 56.0, 60.0, 110.8, 112.5, 125.4, 127.0, 128.6, 130.2, 131.9, 138.9, 143.9, 145.5 |
| EIHR-MS | calcd for C$_{18}$H$_{20}$ClNO$_2$ [M], 317.1183; found, 317.1180 |

| Compound number | 67 |
|---|---|
| Name | 2-(2,4-Dichlorophenethyl)-6-methoxy-1,2,3,4-tetrahydroisoquinolin-7-ol |
| $^1$H NMR (200 MHz, CDCl$_3$) | 2.63-2.91 (m, 8H), 3.61 (s, 2H), 3.83 (s, 3H), 6.56 (s, 2H), 7.15-7.24(m, 2H), 7.33-7.43 (m, 1H) |
| $^{13}$C NMR (50 MHz, CDCl$_3$) | 28.8, 31.0, 51.0, 55.5, 56.0, 57.8, 110.8, 112.5, 125.5, 127.1, 127.2, 129.3, 131.7, 132.6, 134.8, 136.6, 143.9, 145.4 |
| EIHR-MS | calcd for C$_{18}$H$_{19}$Cl$_2$NO$_2$ [M]$^+$, 351.0793; found, 351.0799 |

| Compound number | 68 |
|---|---|
| Name | 2-(4-Bromophenethyl)-6-methoxy-1,2,3,4-tetrahydroisoquinolin-7-ol |
| $^1$H NMR (200 MHz, CDCl$_3$) | 2.67-2.92 (m, 8H), 3.59 (s, 2H), 3.84 (s, 3H), 6.57 (s, 2H), 7.07-7.15 (m, 2H), 7.37-7.44 (m, 2H) |
| $^{13}$C NMR (50 MHz, CDCl$_3$) | 28.8, 33.5, 51.2, 55.6, 56.1, 60.0, 110.8, 112.4, 120.0, 125.5, 127.2, 130.6, 130.6, 139.5, 143.9, 145.4 |
| EIHR-MS | calcd for C$_{18}$H$_{20}$BrNO$_2$ [M]$^+$, 313.0677; found, 313.0676 |

| Compound number | 69 |
|---|---|
| Name | 2-(3-Bromophenethyl)-6-methoxy-1,2,3,4-tetrahydroisoquinolin-7-ol |
| $^1$H NMR (200 MHz, CDCl$_3$) | 2.67-2.93 (m, 8H), 3.59 (s, 2H), 3.84 (s, 3H), 6.57 (s, 2H), 7.13-7.19 (m, 2H), 7.28-7.40 (m, 2H) |
| $^{13}$C NMR (50 MHz, CDCl$_3$) | 28.8, 33.7, 51.2, 55.6, 56.1, 60.0, 110.8, 112.4, 122.5, 125.5, 127.2, 127.6, 129.3, 130.1, 131.9, 142.9, 143.9, 145.4 |
| EIHR-MS | calcd for C$_{18}$H$_{20}$BrNO$_2$ [M]$^+$, 313.0677; found, 313.0665 |

| Compound number | 70 |
|---|---|
| Name | 6-Methoxy-2-(3-Methoxyphenethyl)-1,2,3,4-tetrahydroisoquinolin-7-ol |
| $^1$H NMR (200 MHz, CDCl$_3$) | 2.69-2.96 (m, 8H), 3.60 (s, 2H), 3.80 (s, 3H), 3.84 (s, 3H), 6.57 (s, 2H), 6.72-6.88 (m, 3H), 7.16-7.28 (m, 1H) |
| $^{13}$C NMR (50 MHz, CDCl$_3$) | 28.8, 34.1, 51.2, 55.3, 55.6, 56.1, 60.3, 110.8, 111.5, 112.1, 112.4, 114.6, 121.2, 125.5, 127.2, 129.5, 142.1, 143.8, 145.4, 159.7 |
| EIHR-MS | calcd for C$_{19}$H$_{23}$NO$_3$ [M]$^+$, 313.1678; found, 313.1678 |

| Compound number | 71 |
|---|---|
| Name | 2-Heptyl-6-methoxy-1,2,3,4-tetrahydroisoquinolin-7-ol |
| $^1$H NMR (200 MHz, CDCl$_3$) | 0.85-0.88 (m, 3H), 1.18-1.50 (m, 8H), 1.50-1.70 (m, 2H), 2.43-2.51 (m, 2H), 2.66-2.71 (m, 2H), 2.78-2.81 (m, 2H), 3.50 (s, 2H), 3.83 (s, 3H), 6.55 (s, 2H) |
| $^{13}$C NMR (50 MHz, CDCl$_3$) | 14.2, 22.8, 27.3, 27.8, 28.8, 29.4, 32.0, 51.2, 55.7, 56.0, 58.7, 110.8, 112.5, 125.6, 127.6, 143.8, 145.4 |
| ESI-MS | m/z 278.2 ([M + H]$^+$) |

| Compound number | 72 |
|---|---|
| Name | 6-Methoxy-2-octyl-1,2,3,4-tetrahydroisoquinolin-7-ol |
| $^1$H NMR (200 MHz, CDCl$_3$) | 0.88(s, 3H), 1.18-1.50 (m, 10H), 1.50-1.70(m 2H), 2.43-2.51 (m, 2H), 2.66-2.71 (m, 2H), 2.78-2.81 (m, 2H), 3.50 (s, 2H), 3.84 (s, 3H), 6.56 (s, 2H) |
| $^{13}$C NMR (50 MHz, CDCl$_3$) | 14.3, 22.8, 27.3, 27.8, 28.8, 29.4, 29.7, 32.0, 51.2, 55.8, 56.1, 58.7, 110.8, 112.5, 125.6, 127.5, 143.8, 145.4 |
| ESI-MS | m/z 292.2 ([M + H]$^+$) |

| Compound number | 73 |
|---|---|
| Name | 6-Methoxy-2-nonyl-1,2,3,4-tetrahydroisoquinolin-7-ol |
| $^1$H NMR (200 MHz, CDCl$_3$) | 0.88(s 3H), 1.28 (bs, 12H), 1.50-1.70(m 2H), 2.43-2.51 (m, 2H), 2.69-2.72 (m, 2H), 2.79-2.81 (m, 2H), 3.50 (s, 2H), 3.83 (s, 3H), 6.55 (s, 2H) |
| $^{13}$C NMR (50 MHz, CDCl$_3$) | 14.3, 22.8, 27.3, 27.8, 28.8, 29.4, 29.7, 32.0, 51.2, 55.7, 56.1, 58.7, 110.8, 112.5, 125.7, 127.5, 143.8, 145.4 |
| ESI-MS | m/z 306.2 ([M + H]$^+$) |

| Compound number | 74 |
|---|---|
| Name | 2-(3,4-Dimethoxyphenethyl)-6-methoxy-1,2,3,4-tetrahydroisoquinolin-7-ol |

TABLE 7-continued

The analytical data of the compounds in this invention

| | |
|---|---|
| $^1$H NMR (200 MHz, CDCl$_3$) | 2.68-2.93 (m, 8H), 3.60 (s, 2H), 3.84 (s, 3H), 3.86 (s, 3H), 3.87 (s, 3H), 6.57 (s, 2H), 6.73-6.84 (m, 3H) |
| $^{13}$C NMR (50 MHz, CDCl$_3$) | 28.8, 33.6, 51.3, 55.6, 56.0, 60.5, 110.8, 111.3, 112.1, 112.4, 120.6, 125.5, 127.2, 133.0, 143.8, 145.4, 147.4, 148.9 |
| EIHR-MS | calcd for C$_{20}$H$_{25}$NO$_4$ [M]$^+$, 343.1784; found, 343.1788 |

| Compound number | 75 |
|---|---|
| Name | 2-(2-Chlorophenethyl)-6-methoxy-1,2,3,4-tetrahydroisoquinolin-7-ol |
| $^1$H NMR (200 MHz, CDCl$_3$) | 2.68-2.90(m, 6H), 2.98-3.11 (m, 2H), 3.63 (s, 2H), 3.83 (s, 3H), 6.57 (s, 2H), 7.09-7.24 (m, 2H), 7.24-7.39 (m, 2H) |
| $^{13}$C NMR (50 MHz, CDCl$_3$) | 28.8, 31.6, 51.0, 55.5, 56.0, 58.1, 110.8, 112.5, 125.5, 127.0, 127.2, 127.7, 129.6, 131.0, 134.1, 138.0, 143.8, 145.4 |
| ESI-MS | m/z 318 ([M + H]$^+$), 340 ([M + Na]$^+$) |
| EIHR-MS | calcd for C$_{18}$H$_{21}$ClNO$_2$ [M + H]$^+$, 318.1261; found, 318.1253 |

| Compound number | 78 |
|---|---|
| Name | 6-Methoxy-2-(3-(2-nitrophenyl)propyl)-1,2,3,4-tetrahydroisoquinolin-7-ol |
| $^1$H NMR (200 MHz, CDCl$_3$) | 1.80-2.09 (m, 2H), 2.44-2.63 (m, 2H), 2.64-2.75 (m, 2H), 2.76-2.88 (m, 2H), 2.88-3.07 (m, 2H), 3.51 (s, 2H), 3.83 (s, 3H), 6.55 (s, 1H), 6.56 (s, 1H), 7.28-7.43 (m, 2H), 7.45-7.58 (m, 1H), 7.83-7.95 (m, 1H) |
| $^{13}$C NMR (50 MHz, CDCl$_3$) | 28.2, 28.8, 31.0, 51.0, 55.7, 56.0, 57.7, 110.8, 112.4, 124.8, 125.6, 127.1, 127.4, 132.2, 133.0, 137.4, 143.8, 145.4, 149.5 |
| EIHR-MS | calcd for C$_{19}$H$_{23}$N$_2$O$_4$ [M + H]$^+$, 343.1658; found, 343.1661 |

| Compound number | 85 |
|---|---|
| Name | 8-Bromo-6-methoxy-2-(4-nitrophenethyl)-1,2,3,4-tetrahydroisoquinolin-7-ol |
| $^1$H NMR (200 MHz, CDCl$_3$) | 2.71-2.93 (m, 6H), 2.97-3.10 (m, 2H), 3.62 (s, 2H), 3.87 (s, 3H), 6.59 (s, 1H), 7.37-7.46 (m, 2H), 8.12-8.20 (m, 2H) |
| $^{13}$C NMR (50 MHz, CDCl$_3$) | 29.3, 33.9, 50.4, 56.1, 56.4, 59.1, 108.8, 110.1, 123.8, 126.2, 127.1, 129.7, 141.3, 145.6, 146.6, 148.4 |
| ESI-MS | m/z 407 ([M + H]$^+$), 429 ([M + Na]$^+$) |
| EIHR-MS | calcd for C$_{18}$H$_{20}$BrN$_2$O$_4$ [M + H]$^+$, 407.0606; found, 407.0585 |

| Compound number | 95 |
|---|---|
| Name | 8-Bromo-2-(2-chlorophenethyl)-6-methoxy-1,2,3,4-tetrahydroisoquinolin-7-ol |
| $^1$H NMR (200 MHz, CDCl$_3$) | 2.72-2.93 (m, 6H), 2.98-3.15 (m, 2H), 3.66 (s, 2H), 3.86 (s, 3H), 6.11 (bs, 1H), 6.58 (s, 1H), 7.10-7.25 (m, 2H), 7.25-7.41 (m, 2H) |
| $^{13}$C NMR (50 MHz, CDCl$_3$) | 29.4, 31.6, 50.2, 56.2, 56.4, 58.0, 108.9, 110.2, 126.6, 127.0, 127.3, 127.8, 129.7, 131.0, 134.2, 138.0, 141.2, 145.5 |
| ESI-MS | m/z 396 ([M + H]$^+$) |
| EIHR-MS | calcd for C$_{18}$H$_{20}$BrClNO$_2$ [M + H]$^+$, 396.0366; found, 396.0355 |

| Compound number | 96 |
|---|---|
| Name | 8-Bromo-2-(2-fluorophenethyl)-6-methoxy-1,2,3,4-tetrahydroisoquinolin-7-ol |
| $^1$H NMR (200 MHz, CDCl$_3$) | 2.69-2.91 (m, 6H), 2.91-3.05 (m, 2H), 3.63 (s, 2H), 3.85 (s, 3H), 6.57 (s, 1H), 6.94-7.12 (m, 2H), 7.12-7.33 (m, 2H) |
| $^{13}$C NMR (50 MHz, CDCl$_3$) | 27.2, 29.3, 50.2, 56.2, 56.4, 58.4, 109.1, 110.2, 115.4 (J = 21.9 Hz), 124.1 (J = 3.2 Hz), 126.5, 127.0, 127.2, 128.0 (J = 8.1 Hz), 131.1 (J = 5.0 Hz), 141.2, 145.6, 161.3 (J = 243 Hz) |
| ESI-MS | m/z 380 ([M + H]$^+$) |
| EIHR-MS | calcd for C$_{18}$H$_{20}$BrFNO$_2$ [M + H]$^+$, 380.0661; found, 380.0662 |

| Compound number | 98 |
|---|---|
| Name | 8-Bromo-6-methoxy-2-(3-(2-nitrophenyl)propyl)-1,2,3,4-tetrahydroisoquinolin-7-ol |
| $^1$H NMR (200 MHz, CDCl$_3$) | 1.86-2.11 (m, 2H), 2.51-2.75 (m, 4H), 2.75-2.90 (m, 2H), 2.90-3.06 (m, 2H), 3.53 (s, 2H), 3.83 (s, 3H), 6.55 (s, 1H), 7.31-7.43 (m, 2H), 7.45-7.58 (m, 1H), 7.82-7.94 (m, 1H) |
| $^{13}$C NMR (50 MHz, CDCl$_3$) | 28.1, 29.2, 30.9, 50.1, 56.3, 57.5, 109.1, 110.1, 124.8, 126.5, 127.1, 127.3, 132.1, 133.0, 137.3, 141.2, 145.7, 149.4 |
| ESI-MS | m/z 421 ([M + H]$^+$) |

| Compound number | 101 |
|---|---|
| Name | 8-(2,4-Dimethoxyphenyl)-6-methoxy-2-(2-(1-naphthyl)ethyl)-1,2,3,4-tetrahydroisoquinolin-7-ol |
| $^1$H NMR (200 MHz, CDCl$_3$) | 2.69-3.02 (m, 6H), 3.19-3.37 (m, 4H), 3.73 (s, 3H), 3.82-3.93 (m, 6H), 6.54-6.63 (m, 1H), 6.63-6.72 (m, 1H), 7.03-7.12 (m, 1H), 7.25-7.29 (m, 1H), 7.29-7.35 (m, 1H), 7.35-7.43 (m, 1H), 7.43-7.55 (m, 2H), 7.65-7.76 (m, 1H), 7.79-7.89 (m, 1H), 7.95-8.04 (m, 1H) |
| $^{13}$C NMR (50 MHz, CDCl$_3$) | 29.2, 31.1, 50.7, 54.3, 55.5, 55.8, 56.1, 59.2, 99.2, 104.9, 110.3, 116.3, 122.6, 123.9 (x 2), 125.1, 125.6, 125.7, 126.0, 126.7, 127.0, 128.9, 132.0 (x 2), 134.0, 136.6, 141.5, 145.4, 158.2, 160.9 |

| Compound number | 102 |
|---|---|
| Name | 8-(2,4-Dimethoxyphenyl)-2-(2-(3-indolyl)ethyl)-6-methoxy-1,2,3,4-tetrahydroisoquinolin-7-ol |
| $^1$H NMR (200 MHz, CDCl$_3$) | 2.72-3.42 (m, 10H), 3.70 (s, 3H), 3.85 (s, 3H), 3.88 (s, 3H), 6.53-6.70 (m, 2H), 6.73-6.87 (m, 1H), 6.94-7.23 (m, 5H), 7.28-7.40 (m, 1H), 7.51-7.69 (m, 1H) |

| Compound number | 105 |
|---|---|
| Name | 2-(4-Nitrophenethyl)-8-(2,4-dimethoxyphenyl)-6-methoxy-1,2,3,4-tetrahydroisoquinolin-7-ol |
| $^1$H NMR (200 MHz, CDCl$_3$) | 2.61-2.81 (m, 4H), 2.82-2.95 (m, 4H), 3.23 (s, 2H), 3.72 (s, 3H), 3.85 (s, 3H), 3.88 (s, 3H), 6.53-6.61 (m, 2H), 6.63 (s, 1H), 6.91-7.17 (m, 1H), 7.25-7.35 (m, 2H), 8.05-8.13 (m, 2H) |
| $^{13}$C NMR (50 MHz, CDCl$_3$) | 29.3, 33.7, 50.7, 54.2, 55.5, 55.7, 56.0, 59.1, 99.2, 104.8, 110.2, 116.3, 122.4, 123.7, 125.0, 126.4, 129.6, 131.9, 141.4, 145.2, 146.5, 148.6, 158.1, 160.8 |
| EIHR-MS | calcd for C$_{26}$H$_{29}$N$_2$O$_6$ [M + H]$^+$, 465.2025; found, 465.2055 |

| Compound number | 106 |
|---|---|
| Name | 2-(4-Chlorophenethyl)-8-(2,4-dimethoxyphenyl)-6-methoxy-1,2,3,4-tetrahydroisoquinolin-7-ol |
| $^1$H NMR (200 MHz, CDCl$_3$) | 2.47-2.77 (m, 6H), 2.77-2.88 (m, 2H), 3.16 (s, 2H), 3.65 (s, 3H), 3.78 (s, 3H), 3.80 (s, 3H), 6.47-6.54 (m, 2H), 6.55 (s, 1H), 6.93-7.05 (m, 3H), 7.09-7.20 (m, 2H) |
| $^{13}$C NMR (50 MHz, CDCl$_3$) | 29.3, 33.3, 50.6, 54.2, 55.4, 55.7, 56.0, 59.8, 99.2, 104.8, 110.2, 116.3, 122.5, 125.1, 126.6, 128.5, 130.1, 131.7, 131.9, 139.0, 141.4, 145.2, 158.1, 160.7 |
| ESI-MS | m/z 452 ([M − H]$^+$), 476 ([M + Na]$^+$) |
| EIHR-MS | calcd for C$_{26}$H27ClNO$_4$ [M − H]$^+$, 452.1629; found, 452.1623 |

TABLE 7-continued

The analytical data of the compounds in this invention

| | Compound number 107 |
|---|---|
| Name | 2-(2,4-Dichlorophenethyl)-8-(2,4-dimethoxyphenyl)-6-methoxy-1,2,3,4-tetrahydroisoquinolin-7-ol |
| $^1$H NMR (200 MHz, CDCl$_3$) | 2.54-2.65 (m, 2H), 2.69-2.95 (m, 6H), 3.26 (s, 2H), 3.73 (s, 3H), 3.85 (s, 3H), 3.88 (s, 3H), 6.54-6.61 (m, 2H), 6.63 (s, 1H), 7.02-7.07 (m, 1H), 7.12 (s, 1H), 7.12 (s, 1H), 7.30-7.33 (m, 1H) |
| ESI-MS | m/z 488 ([M + H]$^+$) |
| EIHR-MS | calcd for C$_{26}$H$_{26}$Cl$_2$NO$_4$ [M − H]$^+$, 486.1239; found, 486.1233 |

| | Compound number 108 |
|---|---|
| Name | 2-(4-Bromophenethyl)-8-(2,4-dimethoxyphenyl)-6-methoxy-1,2,3,4-tetrahydroisoquinolin-7-ol |
| $^1$H NMR (200 MHz, CDCl$_3$) | 2.53-2.83 (m, 6H), 2.84-2.96 (m, 2H), 3.23 (bd, 2H), 3.72 (s, 3H), 3.85 (s, 3H), 3.87 (s, 3H), 6.53-6.62 (m, 2H), 6.62 (s, 1H), 6.98-7.07 (m, 3H), 7.28-7.42 (m, 2H) |
| $^{13}$C NMR (50 MHz, CDCl$_3$) | 29.3, 33.4, 50.6, 54.2, 55.5, 55.7, 56.0, 59.7, 99.2, 104.8, 110.2, 116.3, 119.8, 122.5, 125.1, 126.6, 130.6, 131.4, 131.9, 139.6, 141.4, 145.3, 158.2, 160.8 |
| ESI-MS | m/z 496 ([M − H]$^+$) |
| EIHR-MS | calcd for C$_{26}$H$_{27}$BrNO$_4$ [M − H]$^+$, 496.1123; found, 496.1118 |

| | Compound number 109 |
|---|---|
| Name | 2-(3-Bromophenethyl)-8-(2,4-dimethoxyphenyl)-6-methoxy-1,2,3,4-tetrahydroisoquinolin-7-ol |
| $^1$H NMR (200 MHz, CDCl$_3$) | 2.54-2.83 (m, 6H), 2.83-2.96 (m, 2H), 3.13-3.33 (m, 2H), 3.72 (s, 3H), 3.85 (s, 3H), 3.87 (s, 3H), 6.54-6.61 (m, 2H), 6.62 (s, 1H), 6.99-7.15 (m, 3H), 7.24-7.35 (m, 1H) |
| $^{13}$C NMR (50 MHz, CDCl$_3$) | 29.2, 33.6, 50.6, 54.2, 55.4, 55.7, 56.0, 59.6, 99.2, 110.2, 116.3, 122.4, 122.5, 125.0, 126.5, 127.5, 129.1, 130.7, 131.7, 131.9, 141.4, 142.9, 145.2, 158.1, 160.8 |
| ESI-MS | m/z 498 ([M + H]$^+$) |
| EIHR-MS | calcd for C$_{26}$H$_{27}$BrNO$_4$ [M − H]$^+$, 496.1123; found, 496.1118 |

| | Compound number 110 |
|---|---|
| Name | 8-(2,4-Dimethoxyphenyl)-6-methoxy-2-(3-methoxyphenethyl)-1,2,3,4-tetrahydroisoquinolin-7-ol |
| $^1$H NMR (200 MHz, CDCl$_3$) | 2.51-2.85 (m, 6H), 2.86-2.98 (m, 2H), 3.25 (s, 2H), 3.71 (s, 3H), 3.76 (s, 3H), 3.84 (s, 3H), 3.86 (s, 3H), 6.53-6.60 (m, 2H), 6.62 (s, 1H), 6.67-6.79 (m, 3H), 7.00-7.07 (m, 1H), 7.10-7.21 (m, 1H) |
| $^{13}$C NMR (50 MHz, CDCl$_3$) | 29.2, 33.9, 50.5, 54.1, 55.2, 55.4, 55.6, 55.9, 59.9, 99.1, 104.8, 110.1, 111.3, 114.4, 116.3, 121.1, 122.4, 125.0, 126.5, 129.3, 131.8, 141.3, 142.0, 145.2, 158.0, 159.6, 160.7 |
| ESI-MS | m/z 448 ([M − H]$^+$), 472 ([M + Na]$^+$) |
| EIHR-MS | calcd for C$_{27}$H$_{31}$NO$_5$ [M]$^+$, 449.2202; found, 449.2197 |

| | Compound number 111 |
|---|---|
| Name | 8-(2,4-Dimethoxyphenyl)-2-heptyl-6-methoxy-1,2,3,4-tetrahydroisoquinolin-7-ol |
| $^1$H NMR (200 MHz, CDCl$_3$) | 0.83-0.89 (m, 3H), 1.10-1.39 (m, 8H), 1.40-1.45 (m, 2H), 2.31-2.38 (m, 2H), 2.63-2.71 (m, 2H), 2.85-2.91 (m, 2H), 3.16 (s, 2H), 3.73 (s, 3H), 3.86 (s, 3H), 3.87 (s, 3H), 5.30 (s, 1H), 6.46-6.61 (m, 2H), 6.67 (d, J = 8.4 Hz, 1H), 7.02-7.06 (m, 1H) |
| $^{13}$C NMR (50 MHz, CDCl$_3$) | 14.2, 22.8, 27.3, 27.7, 29.4, 32.0, 50.5, 54.5, 55.5, 55.7, 56.0, 58.5, 99.2, 104.8, 110.2, 125.3, 132.0, 141.3, 145.1, 158.2, 160.8 |
| ESI-MS | m/z 414.3 ([M + H]$^+$) |

| | Compound number 112 |
|---|---|
| Name | 8-(2,4-Dimethoxyphenyl)-6-methoxy-2-octyl-1,2,3,4-tetrahydroisoquinolin-7-ol |
| $^1$H NMR (200 MHz, CDCl$_3$) | 0.83-0.89 (m, 3H), 1.10-1.38 (m, 10H), 1.40-1.55 (m, 2H), 2.31-2.38 (m, 2H), 2.63-2.71 (m, 2H), 2.85-2.91 (m, 2H), 3.16 (s, 2H), 3.73 (s, 3H), 3.86 (s, 3H), 3.87 (s, 3H), 5.30 (s, 1H), 6.55-6.61 (m, 2H), 6.67 (d, J = 8.4 Hz, 1H), 7.02-7.06 (m, 1H) |
| $^{13}$C NMR (50 MHz, CDCl$_3$) | 14.2, 22.8, 27.2, 27.7, 29.4 (x 2), 29.6, 31.9, 50.5, 54.4, 55.5, 55.7, 56.0, 58.4, 99.2, 104.8, 110.2, 125.3, 126.9, 132.0, 141.4, 145.2, 158.2 |
| ESI-MS | m/s 428.3 ([M + H]$^+$) |

| | Compound number 113 |
|---|---|
| Name | 8-(2,4-Dimethoxyphenyl)-6-methoxy-2-nonyl-1,2,3,4-tetrahydroisoquinolin-7-ol |
| $^1$H NMR (200 MHz, CDCl$_3$) | 0.84-0.90 (m, 3H), 1.24 (bs, 12H), 1.40-1.55 (m, 2H), 2.31-2.38 (m, 2H), 2.61-2.71 (m, 2H), 2.85-2.91 (m, 2H), 3.16 (s, 2H), 3.73 (s, 3H), 3.86 (s, 3H), 3.87 (s, 3H), 5.29 (s, 1H), 6.55-6.61 (m, 2H), 6.67 (d, J = 8.4 Hz, 1H), 7.02-7.06 (m, 1H) |
| $^{13}$C NMR (50 MHz, CDCl$_3$) | 14.2, 22.8, 27.2, 27.7, 29.4, 29.7, 32.0, 50.5, 54.5, 55.5, 55.7, 56.0, 58.4, 99.2, 104.8, 110.2, 122.5, 125.3, 127.0, 131.9, 141.4, 145.2, 158.2, 160.7 |
| ESI-MS | m/z 442.3 ([M + H]$^+$) |

| | Compound number 114 |
|---|---|
| Name | 2-(3,4-Dimethoxyphenethyl)-8-(2,4-dimethoxyphenyl)-6-methoxy-1,2,3,4-tetrahydroisoquinolin-7-ol |
| $^1$H NMR (200 MHz, CDCl$_3$) | 2.54-2.84 (m, 6H), 2.85-2.97 (m, 2H), 3.26 (bd, 2H), 3.71 (s, 3H), 3.83 (s, 3H), 3.83 (s, 6H), 3.86 (s, 3H), 6.53-6.60 (m, 2H), 6.62 (s, 1H), 6.65-6.79 (m, 3H), 7.00-7.07 (m, 1H) |
| $^{13}$C NMR (50 MHz, CDCl$_3$) | 29.2, 33.5, 50.5, 54.1, 55.3, 55.6, 55.8, 55.9, 60.1, 99.0, 104.7, 110.1, 111.1, 111.9, 116.3, 120.5, 122.4, 125.0, 126.5, 131.8, 133.0, 141.3, 145.1, 147.2, 148.7, 158.0, 160.6 |
| ESI-MS | m/z 478 ([M − H]$^+$), 502 ([M + Na]$^+$) |
| EIHR-MS | calcd for C$_{28}$H$_{33}$NO$_6$ [M]$^+$, 479.2308; found, 479.2302 |

| | Compound number 115 |
|---|---|
| Name | 2-(2-Chlorophenethyl)-8-(2,4-dimethoxyphenyl)-6-methoxy-1,2,3,4-tetrahydroisoquinolin-7-ol |
| $^1$H NMR (200 MHz, CDCl$_3$) | 2.48-2.60 (m, 2H), 2.63-2.93 (m, 6H), 3.20 (s, 2H), 3.63 (s, 3H), 3.75 (s, 3H), 3.77 (s, 3H), 6.44-6.52 (m, 2H), 6.54 (s, 1H), 6.92-7.14 (m, 4H), 7.15-7.25 (m, 1H) |
| $^{13}$C NMR (50 MHz, CDCl$_3$) | 29.2, 31.5, 50.4, 54.2, 55.4, 55.6, 55.9, 57.9, 99.1, 104.7, 110.1, 116.3, 122.5, 125.0, 126.7, 126.8, 127.5, 129.4, 130.8, 131.9, 134.0, 138.0, 141.4, 145.2, 158.1, 160.7 |
| EIHR-MS | calcd for C$_{26}$H$_{29}$ClNO$_4$ [M + H]$^+$, 454.1785; found, 454.1799 |

| | Compound number 119 |
|---|---|
| Name | 8-(2,4-Dimethoxyphenyl)-2-(4-fluorophenethyl)-6-methoxy-1,2,3,4-tetrahydroisoquinolin-7-ol |
| $^1$H NMR (200 MHz, CDCl$_3$) | 2.54-2.82 (m, 6H), 2.85-2.96 (m, 2H), 3.24 (d, J = 2.1 Hz, 2H), 3.71 (s, 3H), 3.84 (s, 3H), 3.86 (s, 3H), 6.53-6.60 (m, 2H), 6.62 (s, 1H), 6.84-6.97 (m, 2H), 7.00-7.14 (m, 1H) |
| $^{13}$C NMR (50 MHz, CDCl$_3$) | 29.3, 33.3, 50.7, 54.3, 55.5, 55.8, 56.1, 60.1, 99.3, 104.9, 110.3, 115.0, 115.4, 116.4, 122.7, 125.1, 126.6, 130.1, 130.3, 132.0, 136.2, 141.6, 145.4, 158.2, 160.9, 161.5 (d, J = 242 Hz) |

TABLE 7-continued

The analytical data of the compounds in this invention

| | |
|---|---|
| Compound number | 120 |
| Name | 8-(2,4-Dimethoxyphenyl)-6-methoxy-2-(4-methoxyphenethyl)-1,2,3,4-tetrahydroisoquinolin-7-ol |
| $^1$H NMR (200 MHz, CDCl$_3$) | 2.54-2.80 (m, 6H), 2.84-2.93 (m, 2H), 3.25 (s, 2H), 3.71 (s, 3H), 3.76 (s, 3H), 3.84 (s, 3H), 3.87 (s, 3H), 6.54-6.60 (m, 2H), 6.62 (s, 1H), 6.75-6.83 (m, 2H), 7.01-7.11 (m, 3H) |
| $^{13}$C NMR (50 MHz, CDCl$_3$) | 29.3, 33.1, 50.6, 54.2, 55.3, 55.4, 55.7, 56.0, 60.4, 99.1, 104.8, 110.2, 113.8, 116.4, 122.5, 125.1, 126.7, 129.6, 131.9, 132.6, 141.4, 145.2, 157.9, 158.1, 160.7 |
| ESI-MS | m/z 448 ([M − H]$^+$), 472 ([M + Na]$^+$) |
| EIHR-MS | calcd for C$_{27}$H$_{31}$NO$_5$ [M], 448.2124; found, 448.2118 |

| | |
|---|---|
| Compound number | 121 |
| Name | 8-(2,4-Dimethoxyphenyl)-6-methoxy-2-(4-methylphenethyl)-1,2,3,4-tetrahydroisoquinolin-7-ol |
| $^1$H NMR (200 MHz, CDCl$_3$) | 2.29 (s, 3H), 2.55-2.84 (m, 6H), 2.84-2.96 (m, 2H), 3.25 (bd, 2H), 3.71 (s, 3H), 3.84 (s, 3H), 3.86 (s, 3H), 6.54-6.60 (m, 2H), 6.62 (s, 1H), 7.01 (s, 1H), 7.02-7.07 (m, 4H) |
| $^{13}$C NMR (50 MHz, CDCl$_3$) | 21.1, 29.3, 33.5, 50.6, 54.2, 55.4, 55.7, 56.0, 60.2, 99.1, 104.8, 110.2, 116.4, 122.5, 125.1, 126.7, 128.6, 129.0, 131.9, 135.5, 137.4, 141.4, 145.2, 158.1, 160.7 |
| EIHR-MS | calcd for C$_{27}$H$_{32}$NO$_4$ [M + H]$^+$, 434.2331; found, 434.2348 |

| | |
|---|---|
| Compound number | 122 |
| Name | 2-(3-Chlorophenethyl)-8-(2,4-dimethoxyphenyl)-6-methoxy-1,2,3,4-tetrahydroisoquinolin-7-ol |
| $^1$H NMR (200 MHz, CDCl$_3$) | 2.58-2.99 (m, 8H), 3.12 (d, J = 15.4 Hz, 1H), 3.20 (d, J = 15.3 Hz, 1H), 3.65 (s, 3H), 3.78 (s, 3H), 3.80 (s, 3H), 6.46-6.54 (m, 2H), 6.55 (s, 1H), 6.91-7.01 (m, 2H), 7.03-7.14 (m, 3H) |
| $^{13}$C NMR (50 MHz, CDCl$_3$) | 29.2, 33.7, 50.6, 54.2, 55.4, 55.7, 56.0, 59.6, 99.2, 104.8, 110.1, 116.3, 122.5, 125.0, 126.2, 126.5, 127.0, 128.8, 129.6, 131.9, 134.1, 141.4, 142.5, 145.2, 158.1, 160.8 |
| EIHR-MS | calcd for C$_{26}$H$_{29}$ClNO$_4$ [M + H]$^+$, 454.1785; found, 454.1798 |

| | |
|---|---|
| Compound number | 123 |
| Name | 8-(2,4-Dimethoxyphenyl)-6-methoxy-2-(2-methoxyphenethyl)-1,2,3,4-tetrahydroisoquinolin-7-ol |
| $^1$H NMR (200 MHz, CDCl$_3$) | 2.52-2.86 (m, 6H), 2.87-2.98 (m, 2H), 3.27 (s, 2H), 3.71 (s, 3H), 3.75 (s, 3H), 3.83 (s, 3H), 3.86 (s, 3H), 6.53-6.61 (m, 2H), 6.62 (s, 1H), 6.76-6.89 (m, 2H), 7.01-7.19 (m, 3H) |
| $^{13}$C NMR (50 MHz, CDCl$_3$) | 28.1, 29.3, 50.3, 54.2, 55.2, 55.4, 55.6, 58.3, 99.1, 104.7, 104.7, 110.1, 110.3, 116.4, 120.4, 122.5, 125.2, 126.9, 127.3, 128.8, 130.2, 131.9, 141.3, 145.1, 157.5, 158.1, 160.7 |
| EIHR-MS | calcd for C$_{27}$H$_{32}$NO$_5$ [M + H]$^+$, 450.2280; found, 450.2297 |

| | |
|---|---|
| Compound number | 125 |
| Name | 8-(2,4-Dimethoxyphenyl)-6-methoxy-2-(3-phenylpropyl)-1,2,3,4-tetrahydroisoquinolin-7-ol |
| $^1$H NMR (200 MHz, CDCl$_3$) | 1.70-1.88 (m, 2H), 2.35-2.47 (m, 2H), 2.53-2.74 (m, 4H), 2.83-2.93 (m, 2H), 3.14 (d, J = 15.2 Hz, 1H), 3.23 (d, J = 15.2 Hz, 1H), 3.71 (s, 3H), 3.85 (s, 3H), 3.86 (s, 3H), 5.33 (s, 1H), 6.54-6.60 (m, 1H), 7.00-7.06 (m, 1H), 7.10-7.20 (m, 3H), 7.21-7.31 (m, 2H) |
| $^{13}$C NMR (50 MHz, CDCl$_3$) | 28.7, 29.2, 33.7, 50.5, 54.2, 55.4, 55.7, 56.0, 57.5, 99.1, 104.7, 110.3, 116.3, 122.5, 125.3, 127.0, 128.2, 129.3, 132.0, 138.6, 141.4, 145.2, 158.1, 160.8 |

| | |
|---|---|
| EIHR-MS | calcd for C$_{27}$H$_{32}$NO$_4$ [M + H]$^+$, 434.2331; found, 434.2356 |

| | |
|---|---|
| Compound number | 142 |
| Name | 6-Methoxy-8-(2-methoxyphenyl)-2-(3-(2-nitrophenyl)propyl)-1,2,3,4-tetrahydroisoquinolin-7-ol |
| $^1$H NMR (200 MHz, CDCl$_3$) | 1.69-1.90 (m, 2H), 2.34-2.51 (m, 2H), 2.60-2.78 (m, 2H), 2.78-2.99 (m, 4H), 3.13 (d, J = 15.2 Hz, 1H), 3.23 (d, J = 15.2 Hz, 1H), 3.76 (s, 3H), 3.88 (s, 3H), 6.64 (s, 1H), 6.96-7.10 (m, 2H), 7.15 (dd, J = 7.3, 1.9 Hz, 1H), 7.24-7.29 (m, 1H), 7.32-7.40 (m, 1H), 7.61-7.76 (m, 2H), 7.82-7.92 (m, 1H) |
| $^{13}$C NMR (50 MHz, CDCl$_3$) | 28.1, 29.3, 30.8, 50.2, 54.3, 55.7, 56.0, 57.3, 110.3, 111.4, 120.9, 122.8, 124.1, 124.7, 125.4, 126.3, 127.0, 129.4, 131.6, 132.1, 132.9, 137.4, 141.1, 145.2, 149.4, 157.1 |
| ESI-MS | m/z 449 ([M + H]$^+$) |
| EIHR-MS | calcd for C$_{26}$H$_{29}$N$_2$O$_5$ [M + H]$^+$, 449.2076; found, 449.2098 |

| | |
|---|---|
| Compound number | 150 |
| Name | 8-Bromo-6,7-dimethoxy-2-phenethyl-1,2,3,4-tetrahydroisoquinoline |
| $^1$H NMR (200 MHz, CDCl$_3$) | 2.71-2.94 (m, 8H), 3.63 (s, 2H), 3.82 (s, 3H), 3.83 (s, 3H), 6.63 (s, 1H), 7.20-7.31 (m, 5H) |
| $^{13}$C NMR (50 MHz, CDCl$_3$) | 29.7, 34.1, 50.2, 56.1, 56.4, 60.2, 60.6, 111.7, 118.2, 126.2, 126.8, 128.5, 128.8, 131.9, 140.4, 144.6, 151.7 |
| ESI-MS | m/z 376 ([M + H]$^+$), 398 ([M + Na]$^+$) |
| EIHR-MS | calcd for C$_{19}$H$_{23}$BrNO$_2$ [M + H]$^+$, 376.0912; found, 376.0905 |

| | |
|---|---|
| Compound number | 152 |
| Name | 8-Bromo-6,7-dimethoxy-2-(4-nitrophenethyl)-1,2,3,4-tetrahydroisoquinoline |
| $^1$H NMR (200 MHz, CDCl$_3$) | 2.69-2.80 (m, 2H), 2.80-2.93 (m, 4H), 2.96-3.10 (m, 2H), 3.61 (s, 2H), 3.82 (s, 3H), 3.84 (s, 3H), 6.64 (s, 1H), 7.36-7.46 (m, 2H), 8.10-8.19 (m, 2H) |
| $^{13}$C NMR (50 MHz, CDCl$_3$) | 29.6, 33.9, 50.2, 56.2, 56.3, 59.1, 60.6, 111.7, 118.2, 123.8, 126.5, 129.7, 131.8, 144.7, 146.6, 148.4, 151.8 |
| ESI-MS | m/z 421 ([M + H]$^+$), 443 ([M + Na]$^+$) |
| EIHR-MS | calcd for C$_{19}$H$_{22}$BrN$_2$O$_4$ [M + H]$^+$, 421.0763; found, 421.0730 |

| | |
|---|---|
| Compound number | 153 |
| Name | 8-Bromo-2-(2-chlorophenethyl)-6,7-dimethoxy-1,2,3,4-tetrahydroisoquinoline |
| $^1$H NMR (200 MHz, CDCl$_3$) | 2.73-2.95 (m, 6H), 2.99-3.13 (m, 2H), 3.66 (s, 2H), 3.82 (s, 3H), 3.84 (s, 3H), 6.64 (s, 1H), 7.10-7.25 (m, 2H), 7.29-7.39 (m, 2H) |
| $^{13}$C NMR (50 MHz, CDCl$_3$) | 29.7, 31.7, 50.0, 56.2, 56.4, 58.0, 60.6, 111.8, 118.3, 126.9, 127.0, 127.8, 129.6, 131.0, 131.9, 134.2, 138.0, 144.6, 151.7 |
| ESI-MS | m/z 410 ([M + H]$^+$) |
| EIHR-MS | calcd for C$_{19}$H$_{22}$BrClNO$_2$ [M + H]$^+$, 410.0522; found, 410.0494 |

| | |
|---|---|
| Compound number | 154 |
| Name | 8-Bromo-2-(2-fluorophenethyl)-6,7-dimethoxy-1,2,3,4-tetrahydroisoquinoline |
| $^1$H NMR (200 MHz, CDCl$_3$) | 2.69-2.90 (m, 6H), 2.90-3.04 (m, 2H), 3.63 (s, 2H), 3.82 (s, 3H), 3.84 (s, 3H), 6.63 (s, 1H), 6.95-7.12 (m, 2H), 7.12-7.33 (m, 2H) |
| $^{13}$C NMR (50 MHz, CDCl$_3$) | 27.3, 29.7, 50.0, 56.2, 56.4, 58.4, 60.6, 111.7, 115.3 (J = 22.0 Hz), 118.2, 124.2, 126.8, 127.1 (J = 16.1 Hz), 127.9 (J = 8.0 Hz), 131.1 (J = 4.8 Hz), 131.9, 144.6, |

TABLE 7-continued

The analytical data of the compounds in this invention

| | |
|---|---|
| ESI-MS | 151.6, 161.3 (J = 243 Hz)<br>m/z 394 ([M + H]$^+$) |
| EIHR-MS | calcd for C$_{19}$H$_{22}$BrFNO$_2$ [M + H]$^+$, 394.0818;<br>found, 394.0806 |

Compound number
157

| | |
|---|---|
| Name | 8-(2-Fluorophenyl)-6,7-dimethoxy-2-phenethyl-1,2,3,4-tetrahydroisoquinoline |
| $^1$H NMR<br>(200 MHz,<br>CDCl$_3$) | 2.54-2.88 (m, 6H), 2.88-3.05 (m, 2H), 3.19 (d, J = 15.0 Hz ,1H), 3.30 (d, J = 15.0 Hz, 1H), 3.56 (s, 3H), 3.86 (s, 3H), 6.73 (s, 1H), 7.03-7.41 (m, 9H) |
| $^{13}$C NMR<br>(50 MHz,<br>CDCl$_3$) | 29.5, 34.0, 50.3, 54.2, 55.9, 60.0, 60.8, 112.5, 115.6 (J = 22.2 Hz), 123.6, 124.0 (J = 3.2 Hz), 126.1, 128.1, 128.4, 128.7, 129.4, 130.1, 131.8 (J = 3.5 Hz), 140.4, 145.2, 151.0, 159.9 (J = 234 Hz) |
| ESI-MS | m/z 392 ([M + H]$^+$) |
| EIHR-MS | calcd for C$_{25}$H$_{27}$FNO$_2$ [M + H]$^+$, 390.2026;<br>found, 390.2014 |

Compound number
158

| | |
|---|---|
| Name | 8-(2-Chlorophenyl)-6,7-dimethoxy-2-phenethyl-1,2,3,4-tetrahydroisoquinoline |
| $^1$H NMR<br>(200 MHz,<br>CDCl$_3$) | 2.55-2.68 (m, 2H), 2.68-2.89 (m. 4H), 2.89-3.00 (m, 2H), 3.17 (s, 2H), 3.58 (s, 3H), 3.87 (s, 3H), 6.73 (s, 1H), 7.10-7.27 (m, 6H), 7.27-7.36 (m, 2H), 7.43-7.53 (m, 1H) |
| $^{13}$C NMR<br>(50 MHz,<br>CDCl$_3$) | 29.5, 34.0, 50.4, 53.9, 55.9, 60.0, 60.7, 112.3, 125.7, 126.1, 126.8, 128.4, 128.8, 129.0, 129.5, 130.1, 131.3, 131.8, 133.8, 135.6, 140.4, 144.6, 151.0 |
| ESI-MS | m/z 408 ([M + H]$^+$) |
| EIHR-MS | calcd for C$_{25}$H$_{27}$ClNO$_2$ [M + H]$^+$, 408.1730;<br>found, 408.1730 |

Compound number
159

| | |
|---|---|
| Name | 6,7-Dimethoxy-8-(2-methoxyphenyl)-2-phenethyl-1,2,3,4-tetrahydroisoquinoline |
| $^1$H NMR<br>(200 MHz,<br>CDCl$_3$) | 2.54-2.87 (m, 6H), 2.87-3.00 (m. 2H), 3.15 (d, J = 15.1 Hz, 1H), 3.26 (d, J = 15.1 Hz, 1H), 3.52 (s, 3H), 3.74 (s, 3H), 3.86 (s, 3H), 6.69 (s, 1H), 6.92-7.05 (m, 2H), 7.06-7.15 (m, 2H), 7.15-7.29 (m, 4H), 7.29-7.40 (m, 1H) |
| $^{13}$C NMR<br>(50 MHz,<br>CDCl$_3$) | 29.6, 34.0, 50.4, 54.1, 55.5, 55.8, 60.1, 60.6, 110.8, 111.8, 120.6, 125.2, 126.1, 126.3, 128.4, 128.8, 128.9, 129.6, 131.2, 140.5, 145.0, 151.0, 156.9 |
| ESI-MS | m/z 404 ([M + H]$^+$) |
| EIHR-MS | calcd for C$_{26}$H$_{30}$NO$_3$ [M + H]$^+$, 404.2226;<br>found, 404.2217 |

Compound number
165

| | |
|---|---|
| Name | 2-(2-Fluorophenethyl)-8-(2-fluorophenyl)-6,7-dimethoxy-1,2,3,4-tetrahydroisoquinoline |
| $^1$H NMR<br>(200 MHz,<br>CDCl$_3$) | 2.56-2.68 (m, 2H), 2.68-2.88 (m, 4H), 2.88-3.01 (m. 2H), 3.20 (d, J = 15.1 Hz, 1H), 3.31 (d, J = 15.1 Hz, 1H), 3.56 (s, 3H), 3.86 (s, 3H), 6.73 (s, 1H), 6.89-7.06 (m, 2H), 7.09-7.24 (m, 5H), 7.28-7.42 (m, 1H) |
| $^{13}$C NMR<br>(50 MHz,<br>CDCl$_3$) | 27.2, 29.5, 50.1, 54.2, 55.9, 58.2, 60.8, 112.6?+0 115.3 (J = 21.7 Hz), 115.6 (J = 22.0 Hz), 123.6, 124.0 (J = 3.2 Hz), 126.1, 127.2 (J = 15.9 Hz), 127.8 (J = 7.9 Hz), 128.1, 129.5 (J = 7.9 Hz), 130.2, 131.0 (J = 4.9 Hz), 131.8 (J = 3.0 Hz), 145.2, 151.1, 159.9 (J = 244 Hz), 161.2 (J = 243 Hz) |
| ESI-MS | m/z 410 ([M + H]$^+$) |
| EIHR-MS | calcd for C$_{25}$H$_{26}$F$_2$NO$_2$ [M + H]$^+$, 410.1932;<br>found, 410.1927 |

TABLE 7-continued

The analytical data of the compounds in this invention

Compound number
166

| | |
|---|---|
| Name | 8-(2-Chlorophenyl)-2-(2-fluorophenethyl)-6,7-dimethoxy-1,2,3,4-tetrahydroisoquinoline |
| $^1$H NMR<br>(200 MHz,<br>CDCl$_3$) | 2.55-2.68 (m, 2H), 2.68-2.88 (m, 4H), 2.88-3.00 (m. 2H), 3.18 (s, 2H), 3.57 (s, 3H), 3.87 (s, 3H), 6.73 (s, 1H), 6.88-7.05 (m, 2H), 7.06-7.24 (m, 3H), 7.26-7.36 (m, 2H), 7.42-7.52 (m, 1H) |
| $^{13}$C NMR<br>(50 MHz,<br>CDCl$_3$) | 27.2, 29.4, 50.1, 53.9, 55.9, 58.1, 60.7, 112.4, 115.3 (J = 22.0 Hz), 124.0 (J = 3.2 Hz), 125.6, 126.8, 127.2 (J = 16.0 Hz), 127.8 (J = 7.9 Hz), 129.0, 129.5, 130.1, 131.0 (J = 4.9 Hz), 131.3, 131.8, 133.8, 135.6, 144.7, 151.0, 161.2 (J = 243 Hz) |
| ESI-MS | m/z 426 ([M + H]$^+$) |
| EIHR-MS | calcd for C$_{25}$H$_{26}$ClFNO$_2$ [M + H]$^+$, 426.1636;<br>found, 426.1634 |

Compound number
167

| | |
|---|---|
| Name | 2-(2-Chlorophenethyl)-8-(2-fluorophenyl)-6,7-dimethoxy-1,2,3,4-tetrahydroisoquinoline |
| $^1$H NMR<br>(200 MHz,<br>CDCl$_3$) | 2.55-2.70 (m, 2H), 2.70-3.02 (m, 6H), 3.22 (d, J = 15.1 Hz, 1H), 3.32 (d, J = 15.1 Hz, 1H), 3.56 (s, 3H), 3.87(s, 3H), 6.73 (s, 1H), 7.04-7.24(m, 6H), 7.24-7.42 (m, 2H) |
| $^{13}$C NMR<br>(50 MHz,<br>CDCl$_3$) | 29.5, 31.5, 50.1, 54.3, 55.9, 57.9, 60.8, 112.5, 115.6 (J = 22.1 Hz), 123.6, 124.1, 126.1, 126.9, 127.6, 128.1, 129.4 (J = 7.1 Hz), 129.5, 130.1, 130.9, 131.9, 134.0, 137.9, 145.2, 151.1, 159.9 (J = 243 Hz) |
| ESI-MS | m/z 426 ([M + H]$^+$) |
| EIHR-MS | calcd for C$_{25}$H$_{26}$ClFNO$_2$ [M + H]$^+$, 426.1636;<br>found, 426.1640 |

Compound number
168

| | |
|---|---|
| Name | 2-(2-Chlorophenethyl)-8-(2-chlorophenyl)-6,7-dimethoxy-1,2,3,4-tetrahydroisoquinoline |
| $^1$H NMR<br>(200 MHz,<br>CDCl$_3$) | 2.53-2.69 (m, 2H), 2.69-3.03 (m, 6H), 3.20 (s, 2H), 3.57 (s, 3H), 3.87 (s, 3H), 6.73 (s, 1H), 7.02-7.23 (m, 4H), 7.23-7.38 (m, 3H), 7.42-7.54 (m, 1H) |
| $^{13}$C NMR<br>(50 MHz,<br>CDCl$_3$) | 29.5, 31.6, 50.2, 54.0, 55.9, 57.9, 60.7, 112.4, 125.7, 126.8, 127.6, 129.0, 129.5, 130.1, 130.9, 131.3, 131.8, 133.8, 134.1, 135.7, 138.0, 144.7, 151.0 |
| ESI-MS | m/z 442 ([M + H]$^+$) |
| EIHR-MS | calcd for C$_{25}$H$_{26}$Cl$_2$NO$_2$ [M + H]$^+$, 442.1341;<br>found, 442.1335 |

Compound number
171

| | |
|---|---|
| Name | 8-(2-Fluorophenyl)-6,7-dimethoxy-2-(4-nitrophenethyl)-1,2,3,4-tetrahydroisoquinoline |
| $^1$H NMR<br>(200 MHz,<br>CDCl$_3$) | 2.62-3.00 (m, 8H), 3.20 (dd, J = 17.9, 15.1 Hz, 2H), 3.55 (s, 3H), 3.87 (s, 3H), 6.73 (s, 1H), 7.07-7.24 (m, 3H), 7.25-7.42 (m, 3H), 8.04-8.15 (m, 2H) |
| $^{13}$C NMR<br>(50 MHz,<br>CDCl$_3$) | 29.6, 34.1, 50.5, 54.2, 55.9, 59.0, 60.8, 112.5, 115.7 (J = 22.3 Hz), 123.5, 123.7 (J = 17.4 Hz), 124.0, 125.8, 128.1, 129.5 (J = 7.3 Hz), 129.6, 130.0, 131.8 (J = 3.1 Hz), 145.3, 151.0, 161.2 (J = 243 Hz) |
| ESI-MS | m/z 437 ([M + H]$^+$) |
| EIHR-MS | calcd for C$_{25}$H$_{26}$FN$_2$O$_4$ [M + H]$^+$, 437.1877;<br>found, 437.1874 |

Compound number
172

| | |
|---|---|
| Name | 8-(2-Chlorophenyl)-6,7-dimethoxy-2-(4-nitrophenethyl)-1,2,3,4-tetrahydroisoquinolineee |
| $^1$H NMR<br>(200 MHz,<br>CDCl$_3$) | 2.61-2.99 (m, 8H), 3.13 (dd, J = 16.6, 15.2 Hz, 2H), 3.57 (s, 3H), 3.87 (s, 3H), 6.73 (s, 1H), 7.11-7.22 (m, 2H), 7.24-7.37 (m, 4H), 7.47-7.52 (m, 1H), 8.03-8.14 (m, 2H) |
| $^{13}$C NMR<br>(50 MHz,<br>CDCl$_3$) | 29.5, 34.0, 50.6, 53.9, 58.9, 60.7, 112.3, 123.7, 125.3, 126.9, 129.0. 129.6, 130.0, 131.3, 131.8, 133.7, 135.6, 144.7, 146.5, 148.6, 151.1 |

TABLE 7-continued

The analytical data of the compounds in this invention

| ESI-MS | m/z 453 ([M + H]$^+$) |
| --- | --- |
| EIHR-MS | calcd for $C_{25}H_{26}ClN_2O_4$ [M + H]$^+$, 453.1581; found, 453.1571 |

| | Compound number 173 |
| --- | --- |
| Name | 6,7-Dimethoxy-8-(2-methoxyphenyl)-2-(4-nitrophenethyl)-1,2,3,4-tetrahydroisoquinoline |
| $^1$H NMR (200 MHz, CDCl$_3$) | 2.59-3.00 (m, 8H), 3.17 (dd, J = 19.8, 15.0 Hz, 2H), 3.52 (s, 3H), 3.73 (s, 3H), 3.86 (s, 3H), 6.69 (s, 1H), 6.92-7.04 (m, 2H), 7.07 (dd, J = 7.4, 2.2 Hz, 1H), 7.26-7.41 (m, 3H), 8.03-8.14 (m, 2H) |
| $^{13}$C NMR (50 MHz, CDCl$_3$) | 29.6, 34.0, 50.6, 54.1, 55.5, 55.9, 59.0, 60.6, 110.8, 111.8, 120.6, 123.6, 125.1, 126.0, 129.0, 129.6, 131.1, 145.1, 146.5, 148.7, 151.1, 156.9 |
| ESI-MS | m/z 449 ([M + H]$^+$) |
| EIHR-MS | calcd for $C_{26}H_{29}N_2O_5$ [M + H]$^+$, 449.2076; found, 449.2071 |

The 5-HT$_7$ receptor binding affinity, 5-HT$_{2A}$ receptor binding affinity, and log D data of compounds 6-10 are shown in Table 8.

TABLE 8

The receptor binding affinity and log D of 6-10

| compound | $K_i$ (nM), 5-HT$_7$R | $K_i$ (nM), 5-HT$_{2A}$R | log D |
| --- | --- | --- | --- |
| 6 | 3.5 | 2.2 | 3.98 |
| 7 | 1.4 | 70 | 3.66 |
| 8 | 5.8 | >1000 | 1.68 |
| 9 | 4.9 | >1000 | 1.70 |
| 10 | 7.1 | >1000 | 2.93 |

Animals

Specific pathogen free C57BL/6 mice (4-6 weeks of age) obtained from the Animal Center of the National Taiwan University were used for the study. Animals were raised in a temperature-controlled room (20±2° C.) with 12/12-h light/dark cycles, and fed with regular mice chow and water ad libitum. All experimental procedures were approved by the Animal Care and Use Committee of the National Taiwan University.

Reagents

Novel 8-phenyl-isoquinoline derivatives were prepared by the procedures described below. SB-269970 hydrochloride (SB7) (a 5-HT$_7$R antagonist, Sigma #S7389), alosetron hydrochloride (ALN) (a 5-HT$_3$R antagonist, Sigma #SML0346), and loperamide hydrochloride (LPM) (a μ-opioid receptor agonist; Sigma #L4762) were intraperitoneally (i.p.) or perorally (p.o.) administered by a single dose or multiple doses to mice for the analysis of intestinal pain.

Two Experimental Models of Visceral Hypersensitivity (1) Dual Challenge of Giardia Postinfection Combined with Water Avoidance Stress Two animal models of IBS that had shown visceral hypersensitivity were used in the study, including dual challenge of postinfection combined with psychological stress, and post-inflammation. In the first model, mice were divided into two groups, including one group subjected to dual triggers of Giardia postinfection and water avoidance stress (GW) and the one group pair-fed with saline and non-handled (PN) as uninfected unstressed normal controls. Axenic Giardia lamblia trophozoites (strain GS/M, ATCC 50581) were cultured in vitro and harvested at log-phase as described in Singer et al., (T-cell-dependent control of acute Giardia lamblia infections in mice. Infect. Immun. 2000; 68:170-175) and Davids et al. (Polymeric immunoglobulin receptor in intestinal immune defense against the lumen-dwelling protozoan parasite Giardia. J Immunol 2006; 177: 6281-6290). Mice were orally gavaged with 10$^7$ Giardia trophozoites suspended in 0.2 ml of sterile phosphate-buffered saline (PBS) or pair-fed with the same volume of PBS. The status of Giardia infection was verified after 4-7 days by enumeration of motile trophozoites in the small intestine following a cold-shock protocol (disclosed in Scott K G, Yu L C H, Buret A G. Role of CD8+ and CD4+ T lymphocytes in jejunal mucosal injury during murine giardiasis. Infect. Immun. 2004; 72:3536-3542 and Scott K G, Meddings J B, Kirk D R, et al. Intestinal infection with Giardia spp. reduces epithelial barrier function in a myosin light chain kinase-dependent fashion. Gastroenterology 2002; 123:1179-1190). On the sixth week postinfection in which the trophozoites could not be detected in the small intestine (post-clearance phase), mice were subjected to chronic psychological stress. The procedure of WAS involved placing the mouse on a platform (3×6 cm) in the center of a container (56×50 cm) with 3 cm (vertical height) of room temperature water. Mice remained on the platform for 1 hr to avoid water immersion as a psychological stress without physical harm. The 1-hr stress sessions were carried out for 10 consecutive days to mimic chronic repeated stress, and were performed between 9:00 and 12:00 to minimize the effect of the circadian rhythm. Uninfected and unstressed non-handled animals were kept in their cages as normal controls. On the last day of the stress session, intestinal pain was measured in mice.

For testing of anti-nociceptive effects in the GW model, mice were administered novel 5-HT$_7$R ligands by a single dose 90 or 240 minutes prior to intestinal pain measurement. In additional settings, the novel ligands were repeatedly administered for 10 consecutive days 30 minutes before the start of each stress session and intestinal pain was measured immediately after the last stress session.

(2) Postinflammation Model

In the second model, intestinal inflammation was induced by intracolonic administration of 10% 2,4,6-trinotrobenzene sulfonic acid (TNBS) in 0.2 ml of 50% ethanol (Sigma-Aldrich, St. Louis, Mo., USA) via a 22-gauge feeding needle. Sham controls were given PBS in the same volume. Intestinal inflammatory parameters and pain levels were measured on various time points after TNBS administration.

For testing of anti-nociceptive effects in the post-TNBS model, mice were administered with novel 5-HT$_7$R ligands by a single dose at 90 or 240 minutes before or by repeated administration of multiple doses for 10 consecutive days prior to intestinal pain measurement.

Assessment of Pain Sensation to Colorectal Distension

Abdominal pain was measured by visceromotor response (VMR) to colorectal distension (CRD) in mice following previously described methods with slight modification (Lu C L, Hsieh J C, Dun N J, et al. Estrogen rapidly modulates 5-hydroxytrytophan-induced visceral hypersensitivity via GPR30 in rats. Gastroenterology 2009; 137:1040-1050; Hong S, Zheng G, Wu X, et al. Corticosterone mediates reciprocal changes in CB 1 and TRPV1 receptors in primary sensory neurons in the chronically stressed rat. Gastroenterology 2011; 140:627-637 e4). Briefly, electrodes made from Teflon-coated stainless steel wire (A-M systems, Carlsborg, Wash.) were implanted in the abdominal external oblique muscles of mice at least 15 days prior to VMR experiments. The electrodes were exteriorized onto the back of the neck. Mice were habituated in the plexiglass cylinder for 30 minutes per day for 3 consecutive days before VMR experiments. The cylinder was used for partial restraint of conscious mice during the CRD experiments. For recording, electrodes were connected to an electromyogram acquisition system (AD instruments, New south wales, Australia). The colon was distended by inflating a balloon catheter inserted intra-anally such that it ended 1.5 cm proximal to the anus. Mice were subjected to four 10-second distensions (15, 40, and 65 mmHg) with 3-min rest intervals. The electromyographic (EMG) activity was amplified and digitized using a transducer (AD instruments) connected to a P511 AC amplifier (Grass instruments, Calif., USA) and Powerlab device with Chart 5 software (AD instruments). The EMG activity was rectified, and the response was recorded as the increase in the area under the curve (AUC) of the EMG amplitude during CRD versus the baseline period.

Histopathological Examination

Intestinal tissues were fixed in 4% paraformaldehyde (PFA) and embedded in paraffin wax with proper orientation of the crypt to villus axis before sectioning. Sections of 5-µm thickness were deparaffinized with xylene and graded ethanol, stained with hematoxylin and eosin (H&E), and observed under a light microscope.

Reverse Transcription Polymerase Chain Reaction

Total RNA was extracted from tissue samples using Trizol reagent (Invitrogen) according to the manufacturer's instructions. The RNA (2 µg) was reversely transcribed with oligo(dT)$_{15}$ using RevertAid™ First Strant cDNA Synthesis kit (Thermo) in 20 µL reaction volume. The resulting cDNA corresponding to 0.1 µg of initial RNA was then subjected to PCR by the addition of master mix containing 1X PCR buffer, 1 U DreamTaq™ DNA Polymerase, 0.2 mM dNTPs mixture, 0.4 µM upstream primer, and 0.4 µM downstream primer. The specific primer pairs for PCR reaction were as follows: mouse 5-HT$_7$R (forward, 5'-TCTTCGGATGGGCTCAGAATGT-3' and reverse, 5'-AACTTGTGTTTGGCTGCGCT-3'), and β-actin (forward, 5'-GGGAAATCGTGCGTGAC-3' and reverse, 5'-CAAGAAGGAAGGCTGGAA-3') (as disclosed in Forcen R, Latorre E, Pardo J, et al. Toll-like receptors 2 and 4 modulate the contractile response induced by serotonin in mouse ileum: analysis of the serotonin receptors involved. Neurogastroenterol Motil 2015; 27:1258-66). The DNA thermal cycler was programmed to perform a protocol as follows: 95° C. for 3 min for 1 cycle; 95° C. for 30 sec (denaturation), 55° C. for 30 sec (annealing), and 72° C. for 30 sec (extension) for 30 cycles; and 72° C. for 7 min for final extension. Negative controls were performed with samples lacking cDNA that was not reversely transcribed. RT-PCR products were then electrophoresed in a 1.5% agarose gel in the presence of 0.5 µg/mL ethidium bromide, visualized with an ultraviolet transilluminator, and photographs were taken. The intensity of the DNA bands was analyzed using the Gel-Pro Analyzer 4.0 software.

Immunofluorescent Staining of 5-HT$_7$R

Deparaffinized histological slides were incubated with 10 mM Tri-sodium citrate buffer (pH 6.0) containing 0.05% Tween-20 and boiled in microwave. Sections were left at room temperature to cool down. After quenching with 1 mg/ml NaBH4 in PBS (pH 8.0) for 15 minutes at room temperature, tissues were blocked with 1% bovine serum albumin for 2 hours at room temperature. Tissue sections were incubated with primary antibodies, rabbit polyclonal anti-5-HT$_7$R (1:300, Abcam), rabbit PGP9.5 antibody (1:250, GeneTex) or isotype controls overnight at 4° C. The sections were washed with PBS and incubated with a secondary goat anti-rabbit IgG conjugated to Alexa Fluor 488 (1:250, Molecular Probes) for one hour at room temperature. The tissues were then incubated with a Hoechst dye (1 µg/ml in PBS) (Sigma) for another 30 minutes. The slides were observed under a fluorescent microscope and the images were captured.

Western Blotting

Intestinal mucosal proteins were extracted with complete radio-immunoprecipitation (RIPA) buffer and subjected to SDS/polyacrylamide gel electrophoresis (PAGE) (4-13% polyacrylamide) (as described in Kuo W T, Lee T C, Yang H Y, et al. LPS receptor subunits have antagonistic roles in epithelial apoptosis and colonic carcinogenesis. Cell Death Differ 2015; 22:1590-1604; Wu L L, Peng W H, Kuo W T, et al. Commensal Bacterial Endocytosis in Epithelial Cells Is Dependent on Myosin Light Chain Kinase-Activated Brush Border Fanning by Interferon-gamma. Am J Pathol 2014; 184:2260-2274; and Yu L C, Shih Y A, Wu L L, et al. Enteric dysbiosis promotes antibiotic-resistant bacterial infection: systemic dissemination of resistant and commensal bacteria through epithelial transcytosis. Am J Physiol Gastrointest Liver Physiol 2014; 307:G824-35). The resolved proteins were then electrotransferred onto PVDF or nitrocellulose membranes in a semi-dry blotter. Blots were blocked with 5% (w/v) nonfat dry milk in Tris-buffered saline (TB S) or 5% (w/v) bovine serum albumin in TBS with Tween 20 (TBS-T; 0.1% (v/v) Tween-20 in TBS) for 1 h, washed with TBS-T, and incubated with a primary antibody at 4° C. overnight. The membrane was washed and incubated with a secondary antibody for 1 h. After washing, the membranes were incubated with chemiluminescent solution and signals detected. The primary antibodies used included rabbit polyclonal anti-5-HT$_7$R (1:500, Abcam) and anti-β-actin (1:10000, Sigma). The secondary antibodies used were horseradish peroxidase-conjugated goat anti-rabbit IgG (1:1000, Cell Signaling).

Statistical Analysis

All values were expressed as mean±SEM, and compared by paired Student's t test. Significance was established at $P<0.05$.

Intestinal Hypernociception Correlated with Upregulation of Colonic 5-HT$_7$R Expression in two IBS-Like Mouse Models Two animal models of IBS-like visceral hypersensitivity were utilized to examine anti-nociceptive effects of a series of 8-phenylisoquinoline derivatives which were novel 5-HT$_7$R ligands. Mice were divided into two groups, one group was subjected to *Giardia* postinfection and water avoidance stress (GW) and another group was pair-fed and non-handled (PN) as uninfected unstressed normal controls. The visceromotor response (VMR) to colorectal distension was expressed as the area under a curve (AUC), and was determined in each mouse as an indicator of intestinal pain.

In the first model, by dual challenge of *Giardia* postinfection combined with psychological stress (GW) an increased abdominal pain was observed compared to normal controls (FIG. 5(A)). FIG. 5B shows representative images of the colon histology in PN and GW mice. The colonic morphology was similar between GW mice and the normal controls (FIG. 5(B)). 5-HT$_7$R in colonic tissues of PN and GW mice were immunostained. FIG. 5(C) shows the representative images of of 5-HT$_7$R staining (panel a) and quantification of 5-HT$_7$R immunoreactivity in muscle/nerve and mucosal layers (panel b and c). FIG. 5(D) shows the results of Western blotting showing increased 5-HT$_7$R protein levels in GW mice. Upregulated expression of 5-HT$_7$R was observed in colon tissues of GW mice (FIGS. 5(C) and 5(D)), with higher levels located at the smooth muscle, enteric nerves, and mucosal region (FIG. 5(C)).

Figure 6D:
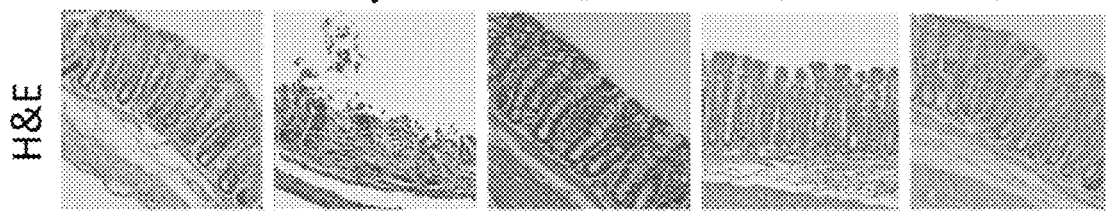
FIG. 6(D) Representative images of colon histology in sham and TNBS mice.
Figure 6E:
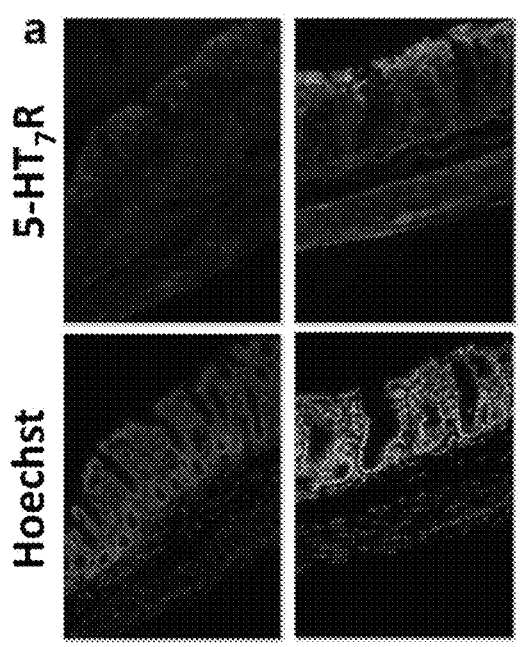
FIG. 6(E) Immunostaining of 5-HT$_7$R in colonic tissues of sham and TNBS-d24 mice. Representative images of 5-HT$_7$R staining (panel a) and quantification of 5-HT$_7$R immunoreactivity in muscle/nerve and mucosal layers (panel b and c).
Figure 6E:
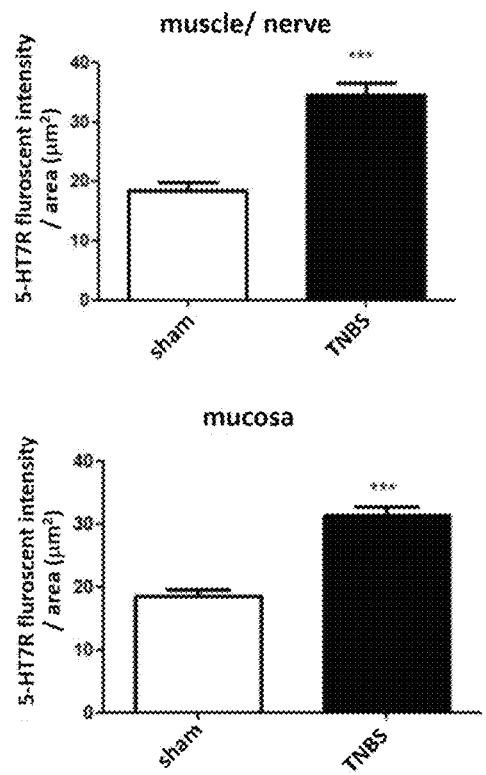
Figure 6F:
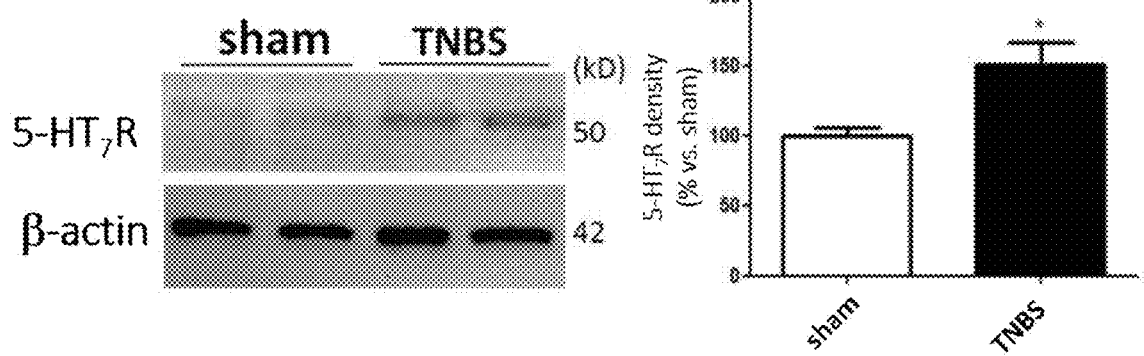
FIG. 6(F) The protein levels of 5-HT$_7$R in mouse colon. (G) The transcript levels of 5-HT$_7$R in mouse colon.
Figure 6G:
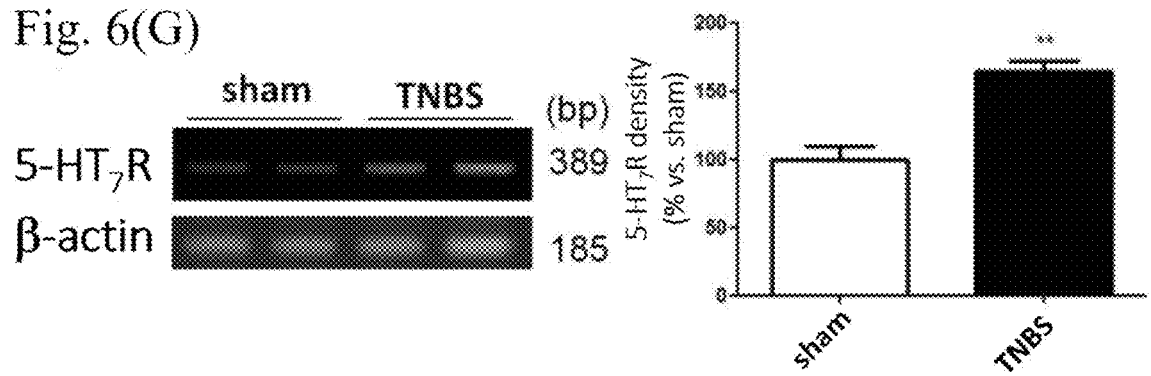
FIG. 6 shows the visceral hypersensitivity noted in an IBS-like mouse model following resolution of TNBS-induced colitis.
FIG. 6(A) The visceromoter response (VMR) to colorectal distension was expressed as area under curve (AUC), and was determined in each mouse as an indicator of intestinal pain.
FIG. 6(B) Intestinal myeloperoxidase (MPO) activity was examined as an indicator of inflammatory leukocyte activation.
FIG. 6(C) Histopathological score of colonic tissues in mice.

In the second model, mice were given one bolus of colitogenic chemical TNBS or PBS intracolonically on day 0 and intestinal inflammation and pain were examined and measured on various days. These animals displayed an increased abdominal pain 7, 14 and 24 days post-TNBS (FIG. 6(A)). However, colonic inflammatory index such as myeloperoxidase activity and histopathological scores peaked by day 2, and showed resolution by day 7 (FIGS. 6B-D). Therefore, post-TNBS on day 24 was used as the time point for examination of IBS-like visceral hypersensitivity. Upregulated expression of 5-HT$_7$R was observed in colon tissues of TNBS mice, with higher levels located at the smooth muscle, enteric nerves, and mucosa region (FIGS. 6E and 6F).

5-HT$_7$R Activation is Involved in Visceral Hypersensitivity in the IBS Models

Figure 7:
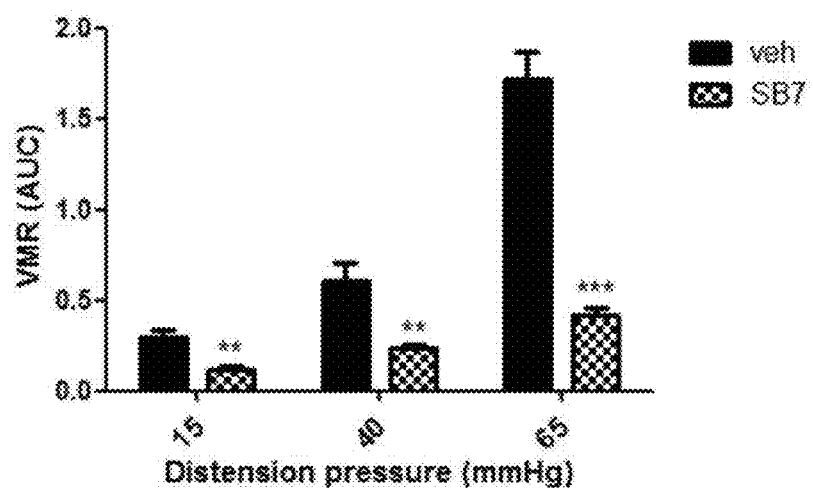
FIG. 7 shows the anti-nociceptive effects of a 5HT$_7$R antagonist SB269970 (SB7) in an IBS-like mouse model.

To verify the role of 5-HT$_7$R on visceral hypersensitivity for proof-of-concept, a putative 5-HT$_7$R antagonist for research use (SB-269970) was intraperitoneally (i.p., 0.5 mg/Kg) injected into the animal models and intestinal pain was measured by VMR. Administration of SB7 through i.p. significantly inhibited intestinal pain levels in mice (FIG. 7).

Anti-Nociceptive Effects of Novel 5-HT$_7$R Ligands

Figure 8:
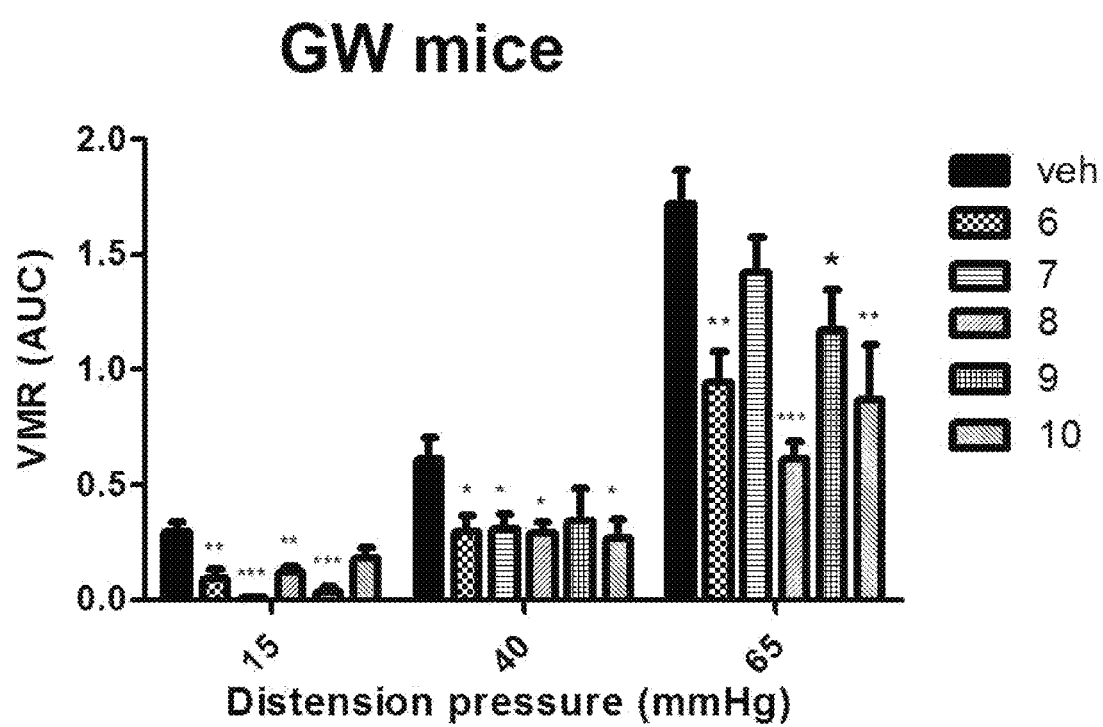
FIG. 8 shows the analgesic effects of oral administration of novel 8-phenylisoquinoline derivatives in GW mice.

Novel 8-phenyl-isoquinoline derivatives (compounds I) targeting 5-HT$_7$R with high binding affinity and water solubility were synthesized (Compounds 6-10 shown in Table 8). In the initial experiments, compounds 6-10 (5-HT$_7$R ligands) were perorally (p.o.) administered at 5 mg/kg in GW mice to assess the inhibitory effect on abdominal pain. A single dose at 5 mg/Kg was administered 90 minutes before the analysis of VMR. All of the compounds tested showed anti-nociceptive effects, among which compound 8 exhibited the strongest inhibition of intestinal pain to baseline levels (FIG. 8).

To examine the dose response on anti-nociceptive effects, compound 8 was injected intraperitoneally (i.p.) at 0.05, and 0.5 mg/kg, or perorally (p.o.) at 1.5, and 5 mg/kg to GW mice. Dose-dependent analgesic effects were observed in GW mice by compound 8 (FIGS. 9A and 9B). To verify whether the analgesic effect was long-lasting, CYY1005 at 5 mg/kg was p.o. administered at either 1.5, 4, or 12 hours prior to pain measurement in GW mice. Reduction of pain levels was seen at three time points (FIG. 9C). Furthermore, repeated administration of compound 8 as multiple doses also decreased intestinal pain in GW mice in a dose-dependent manner (FIG. 9D).

Figure 10:
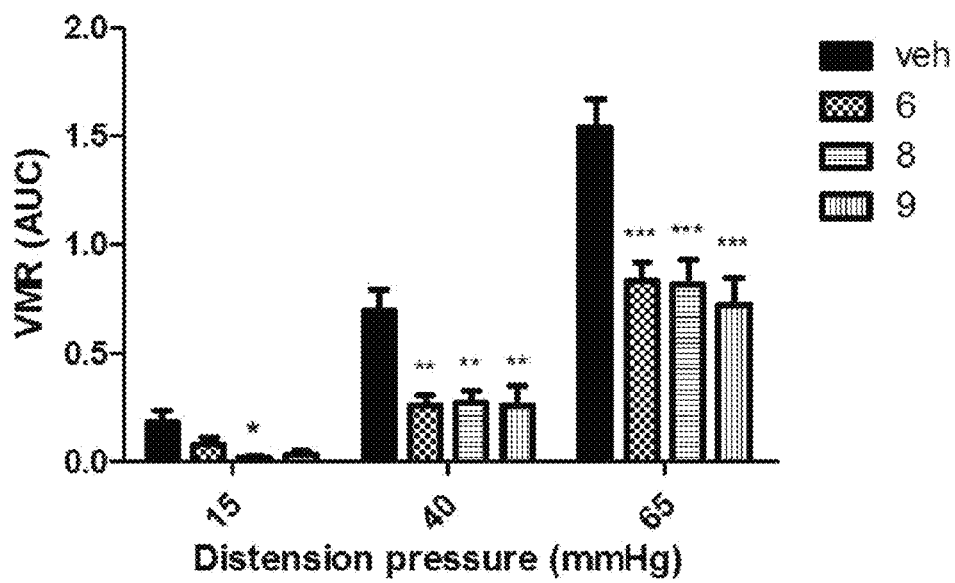
FIG. 10 shows the anti-nociceptive effects of 8-phenylisoquinoline derivatives in TNBS mice.
Figure 10B:
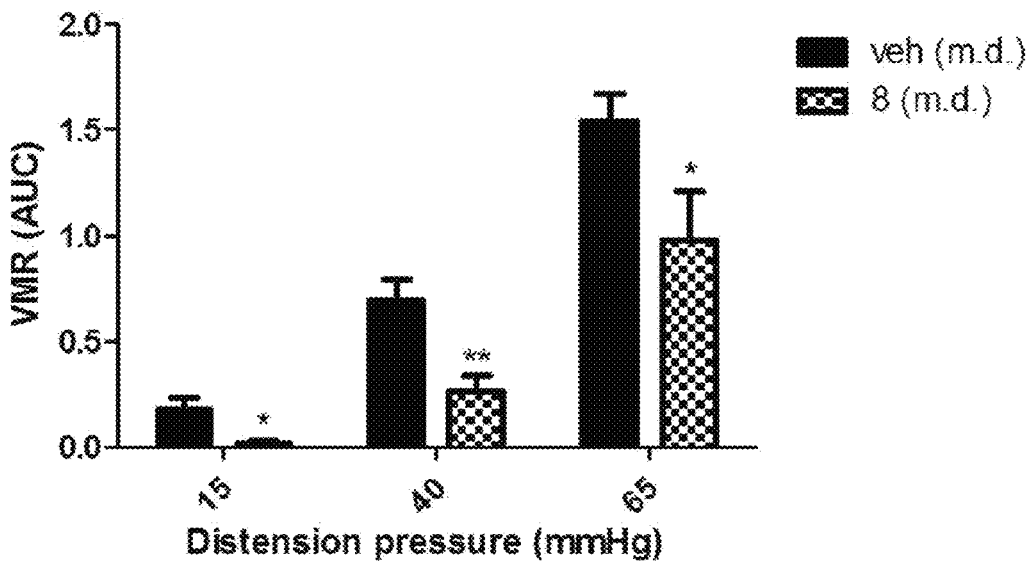

TNBS mice were perorally (p.o.) injected with vehicle or novel 5-HT$_7$R ligands to assess the inhibitory effect on abdominal pain. A single dose at 5 mg/kg was administered 90 minutes before the analysis of VMR. In these TNBS mice, these novel 5-HT$_7$R ligands attenuated intestinal pain at a single dose by p.o. administration (FIG. 10(A)). Similarly, repeated administration of compound 8 as multiple doses also reduced intestinal pain in TNBS mice (FIG. 10(B)).

Figure 11:
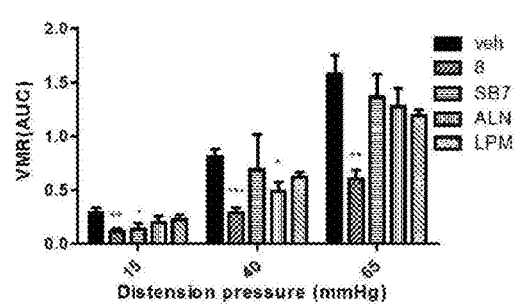
FIG. 11 shows the comparison of analgesic effects and adverse response to compound 8 and reference standards in GW and TNBS mice.
Figure 11:
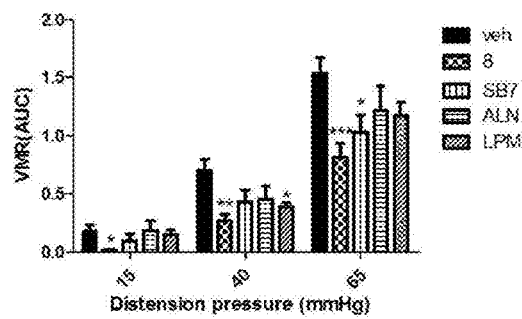

Comparison of analgesic effects and adverse response between 8-phenylisoquinoline derivatives and reference standards The anti-nociceptive potency of compounds I (compounds 6-10) was compared with reference standards by p.o. administration in the two animal models. These compounds and reference standards included SB7 (a 5-HT$_7$R antagonist), alosetron (ALN, a 5-HT$_3$R antagonist), and loperamide (LPM, a μ-opioid receptor agonist) which were administered at 5 mg/Kg 90 minutes before pain analysis. In the GW mice, p.o. administration of ALN reduced intestinal pain but was less efficient compared to compound 8 in GW mice (FIG. 8(A)). On the other hand, p.o. administration of SB7 and LPM had no effect on intestinal nociception in GW mice (FIG. 11(A)). In the second animal model, administration of ALN, SP7, or LPM had no effect on intestinal pain in the TNBS mice (FIG. 11(B)).

Figure 11C:
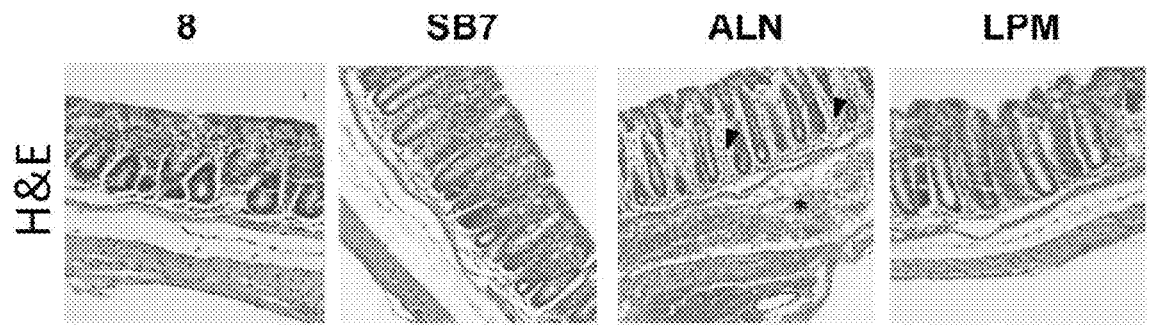
FIG. 11(C) Representative photoimages of colonic histology of each treatment group. Hyperemia (*) and granulocyte infiltration (arrowheads) were observed in the ALN group but not others.

All mice administered vehicle or compounds displayed normal colonic histology, except those given ALN. In 2 out of 14 mice (14%) administered ALN, hyperemia and granulocyte infiltration were observed in the colonic tissues (FIG. 11(C)).

Newly FDA-approved agents, eluxadoline (a mixed μ-opioid agonist) and rifamixin (a nonabsorbable gut-specific antibiotic) had been recent additions to the treatment options for IBS-D. These pharmaceutic agents represented molecular mechanisms or environmental factors different from the 5-HT$_7$R targets. It was noteworthy that any opioid agonist would pose a risk for drug addiction following long-term treatment. Compared to traditional pain-killers (e.g. non-steroidal anti-inflammatory drugs and anticholinergic agents) or anti-diarrheal opioid agonists (e.g. loperamide), this series of 8-phenyl-isoquinoline derivatives, i.e., 5-HT$_7$R antagonists, were more beneficial because they might peripheral-selectively act at the hypernociceptive intestine.

In this invention, 8-phenyl-isoquinoline derivatives (I) (Compounds 6-10) exhibited stronger analgesic actions without adverse effects compared to alosetron in IBS animal models, and therefore they were suitable to be used in both male and female patients as new therapeutic options for IBS treatment.

REFERENCES

The entire context of the following articles is incorporated into the present context by references in their entirieties.

Part I

1. To, Z. P.; Bonhaus, D. W.; Eglen, R. M.; Jakeman, L. B. Characterization and distribution of putative 5-ht7 receptors in guinea-pig brain. *Br J Pharmacol.* 1995, 115, 107-116.
2. Leopoldo, M. Serotonin(7) receptors (5-HT(7)Rs) and their ligands. *Curr Med Chem.* 2004, 11, 629-661.
3. Leopoldo, M.; Lacivita, E.; Berardi, F.; Perrone, R. 5-HT(7) receptor modulators: a medicinal chemistry survey of recent patent literature (2004-2009). *Expert Opin Ther Pat.* 2010, 20, 739-754.
4. Leopoldo, M.; Lacivita, E.; Berardi, F.; Perrone, R.; Hedlund, P. B. Serotonin 5-HT7 receptor agents: Structure-activity relationships and potential therapeutic applications in central nervous system disorders. *Pharmacol Ther.* 2011, 129, 120-148.
5. Tokarski, K.; Bobula, B.; Grzegorzewska-Hiczwa, M.; Kusek, M.; Hess, G. Stress- and antidepressant treatment-induced modifications of 5-HT(7) receptor functions in the rat brain. *Pharmacol Rep.* 2012, 64, 1305-1315.
6. Tokarski, K.; Zelek-Molik, A.; Duszynska, B.; Satala, G.; Bobula, B.; Kusek, M.; Chmielarz, P.; Nalepa, I.; Hess, G. Acute and repeated treatment with the 5-HT7 receptor antagonist SB 269970 induces functional desensitization of 5-HT7 receptors in rat hippocampus. *Pharmacol Rep.* 2012, 64, 256-265.
7. Medina, R. A.; Vazquez-Villa, H.; Gomez-Tamayo, J. C.; Benhamu, B.; Martin-Fontecha, M.; de la Fuente, T.; Caltabiano, G.; Hedlund, P. B.; Pardo, L.; Lopez-Rodriguez, M. L. The extracellular entrance provides selectivity to serotonin 5-HT7 receptor antagonists with antidepressant-like behavior in vivo. *J Med Chem.* 2014, 57, 6879-6884.
8. Mnie-Filali, O.; Faure, C.; Lambas-Senas, L.; El Mansari, M.; Belblidia, H.; Gondard, E.; Etievant, A.; Scarna, H.; Didier, A.; Berod, A.; Blier, P.; Haddjeri, N. Pharmacological blockade of 5-HT7 receptors as a putative fast acting antidepressant strategy. *Neuropsychopharmacology.* 2011, 36, 1275-1288.
9. Nikiforuk, A. Selective blockade of 5-HT7 receptors facilitates attentional set-shifting in stressed and control rats. *Behav Brain Res.* 2012, 226, 118-123.
10. Canale, V.; Kurczab, R.; Partyka, A.; Satala, G.; Lenda, T.; Jastrzebska-Wiesek, M.; Wesolowska, A.; Bojarski, A. J.; Zajdel, P. Towards new 5-HT7 antagonists among arylsulfonamide derivatives of (aryloxy)ethyl-alkyl amines: Multiobjective based design, synthesis, and antidepressant and anxiolytic properties. *Eur J Med Chem.* 2016, 108, 334-346.
11. Zagorska, A.; Kolaczkowski, M.; Bucki, A.; Siwek, A.; Kazek, G.; Satala, G.; Bojarski, A. J.; Partyka, A.; Wesolowska, A.; Pawlowski, M. Structure-activity relationships and molecular studies of novel arylpiperazinylalkyl purine-2,4-diones and purine-2,4,8-triones with antidepressant and anxiolytic-like activity. *Eur J Med Chem.* 2015, 97, 142-154.
12. Roth, B. L.; Craigo, S. C.; Choudhary, M. S.; Uluer, A.; Monsma, F. J., Jr.; Shen, Y.; Meltzer, H. Y.; Sibley, D. R. Binding of typical and atypical antipsychotic agents to 5-hydroxytryptamine-6 and 5-hydroxytryptamine-7 receptors. *J Pharmacol Exp Ther.* 1994, 268, 1403-1410.
13. Andressen, K. W.; Manfra, O.; Brevik, C. H.; Ulsund, A. H.; Vanhoenacker, P.; Levy, F. O.; Krobert, K. A. The atypical antipsychotics clozapine and olanzapine promote down-regulation and display functional selectivity at human 5-HT7 receptors. *Br J Pharmacol.* 2015, 172, 3846-3860.
14. Waters, K. A.; Stean, T. O.; Hammond, B.; Virley, D. J.; Upton, N.; Kew, J. N.; Hussain, I. Effects of the selective 5-HT(7) receptor antagonist SB-269970 in animal models of psychosis and cognition. *Behav Brain Res.* 2012, 228, 211-218.
15. Ivachtchenko, A. V.; Lavrovsky, Y.; Okun, I. AVN-101: A Multi-Target Drug Candidate for the Treatment of CNS Disorders. *J Alzheimers Dis.* 2016, 53, 583-620.
16. Brenchat, A.; Rocasalbas, M.; Zamanillo, D.; Hamon, M.; Vela, J. M.; Romero, L. Assessment of 5-HT(7) Receptor Agonists Selectivity Using Nociceptive and Thermoregulation Tests in Knockout versus Wild-Type Mice. *Adv Pharmacol Sci.* 2012, 2012, 312041.
17. Yesilyurt, O.; Seyrek, M.; Tasdemir, S.; Kahraman, S.; Deveci, M. S.; Karakus, E.; Halici, Z.; Dogrul, A. The critical role of spinal 5-HT7 receptors in opioid and non-opioid type stress-induced analgesia. *Eur J Pharmacol.* 2015, 762, 402-410.
18. Brenchat, A.; Nadal, X.; Romero, L.; Ovalle, S.; Muro, A.; Sanchez-Arroyos, R.; Portillo-Salido, E.; Pujol, M.; Montero, A.; Codony, X.; Burgueno, J.; Zamanillo, D.; Hamon, M.; Maldonado, R.; Vela, J. M. Pharmacological activation of 5-HT7 receptors reduces nerve injury-induced mechanical and thermal hypersensitivity. *Pain.* 2010, 149, 483-494.
19. Tenon, J. A. Role of 5-ht7 receptors in the long-lasting hypotensive response induced by 5-hydroxytryptamine in the rat. *Br J Pharmacol.* 1997, 121, 563-571.
20. Penone-Capano, C.; Adriani, W. Editorial: Further Understanding of Serotonin 7 Receptors' Neuro-psychopharmacology. *Front Behav Neurosci.* 2015, 9, 307.
21. Kim, J. J.; Bridle, B. W.; Ghia, J. E.; Wang, H.; Syed, S. N.; Manocha, M. M.; Rengasamy, P.; Shajib, M. S.; Wan, Y.; Hedlund, P. B.; Khan, W. I. Targeted inhibition of serotonin type 7 (5-HT$_7$) receptor function modulates immune responses and reduces the severity of intestinal inflammation. *J Immunol.* 2013, 190, 4795-4804.
22. De Ponti, F.; Tonini, M. Irritable bowel syndrome: new agents targeting serotonin receptor subtypes. *Drugs.* 2001, 61, 317-332.
23. Yu, F. Y.; Huang, S. G.; Zhang, H. Y.; Ye, H.; Chi, H. G.; Zou, Y.; Lv, R. X.; Zheng, X. B. Comparison of 5-hydroxytryptophan signaling pathway characteristics in diarrhea-predominant irritable bowel syndrome and ulcerative colitis. *World J Gastroenterol.* 2016, 22, 3451-3459.
24. Read, K. E.; Sanger, G. J.; Ramage, A. G. Evidence for the involvement of central 5-HT7 receptors in the micturition reflex in anaesthetized female rats. *Br J Pharmacol.* 2003, 140, 53-60.
25. Schoeffter, P.; Ullmer, C.; Bobirnac, I.; Gabbiani, G.; Lubbert, H. Functional, endogenously expressed 5-hydroxytryptamine 5-ht(7) receptors in human vascular smooth muscle cells. *British Journal of Pharmacology.* 1996, 117, 993-994.
26. Tenon, J. A. Is the 5-HT7 receptor involved in the pathogenesis and prophylactic treatment of migraine? European *Journal of Pharmacology.* 2002, 439, 1-11.
27. Di Pilato, P.; Niso, M.; Adriani, W.; Romano, E.; Travaglini, D.; Berardi, F.; Colabufo, N. A.; Perrone, R.; Laviola, G.; Lacivita, E.; Leopoldo, M. Selective agonists for serotonin 7 (5-HT$_7$) receptor and their applications in preclinical models: an overview. *Rev Neurosci.* 2014, 25, 401-415.
28. Nikiforuk, A. Targeting the Serotonin 5-HT7 Receptor in the Search for Treatments for CNS Disorders: Rationale and Progress to Date. *CNS Drugs.* 2015, 29, 265-275.

Part II
1. Jung I S, Kim H S, Park H, et al. The clinical course of postinfectious irritable bowel syndrome: a five-year follow-up study. J Clin. Gastroenterol. 2009; 43:534-540.
2. Chang F Y, Lu C L, Chen T S. The current prevalence of irritable bowel syndrome in Asia. J. Neurogastroenterol. Motil. 2010; 16:389-400.
3. Elsenbruch S. Abdominal pain in Irritable Bowel Syndrome: a review of putative psychological, neural and neuro-immune mechanisms. Brain Behav Immun 2011; 25:386-94.
4. Stasi C, Bellini M, Bassotti G, et al. Serotonin receptors and their role in the pathophysiology and therapy of irritable bowel syndrome. Tech Coloproctol 2014; 18:613-21.
5. Ford A C, Brandt L J, Young C, et al. Efficacy of 5-HT3 antagonists and 5-HT4 agonists in irritable bowel syndrome: systematic review and meta-analysis. Am J Gastroenterol 2009; 104:1831-43; quiz 1844.
6. Ross C A. Childhood sexual abuse and psychosomatic symptoms in irritable bowel syndrome. J Child Sex Abus 2005; 14:27-38.
7. Qin H Y, Cheng C W, Tang X D, et al. Impact of psychological stress on irritable bowel syndrome. World J Gastroenterol 2014; 20:14126-31.
8. Spiller R, Garsed K. Postinfectious irritable bowel syndrome. Gastroenterology 2009; 136:1979-1988.
9. Beatty J K, Bhargava A, Buret A G. Post-infectious irritable bowel syndrome: Mechanistic insights into chronic disturbances following enteric infection. World J Gastroenterol 2014; 20:3976-3985.
10. Dizdar V, Gilja O H, Hausken T. Increased visceral sensitivity in *Giardia*-induced postinfectious irritable bowel syndrome and functional dyspepsia. Effect of the 5HT3-antagonist ondansetron. Neurogastroenterol. Motil. 2007; 19:977-982.
11. Morch K, Hanevik K, Rortveit G, et al. High rate of fatigue and abdominal symptoms 2 years after an outbreak of giardiasis. Trans. R. Soc. Trop. Med. Hyg. 2009; 103:530-532.
12. Wensaas K A, Langeland N, Hanevik K, et al. Irritable bowel syndrome and chronic fatigue 3 years after acute giardiasis: historic cohort study. Gut 2012; 61:214-9.
13. Halliez M C, Motta J P, Feener T D, et al. *Giardia duodenalis* induces para-cellular bacterial translocation and causes post-infectious visceral hypersensitivity. Am J Physiol Gastrointest Liver Physiol 2016:ajpgi 00144 2015.
14. Lapointe T K, Basso L, Iftinca M C, et al. TRPV1 sensitization mediates postinflammatory visceral pain following acute colitis. Am J Physiol Gastrointest Liver Physiol 2015; 309:G87-99.
15. Feng B, La J H, Tanaka T, et al. Altered colorectal afferent function associated with TNBS-induced visceral hypersensitivity in mice. Am J Physiol Gastrointest Liver Physiol 2012; 303:G817-24.
16. Annahazi A, Dabek M, Gecse K, et al. Proteinase-activated receptor-4 evoked colorectal analgesia in mice: an endogenously activated feed-back loop in visceral inflammatory pain. Neurogastroenterol Motil 2012; 24:76-85, e13.
17. Larauche M, Gourcerol G, Million M, et al. Repeated psychological stress-induced alterations of visceral sensitivity and colonic motor functions in mice: influence of surgery and postoperative single housing on visceromotor responses. Stress 2010; 13:343-54.
18. Hsu L T, Hung K Y, Wu H W, et al. Gut-derived cholecystokinin contributes to visceral hypersensitivity via nerve growth factor-dependent neurite outgrowth. J Gastroenterol Hepatol 2016.
19. Salvioli B, Serra J, Azpiroz F, et al. Origin of gas retention and symptoms in patients with bloating. Gastroenterology 2005; 128:574-9.
20. Tonini M, Vicini R, Cervio E, et al. 5-HT7 receptors modulate peristalsis and accommodation in the guinea pig ileum. Gastroenterology 2005; 129:1557-66.
21. Dickson E J, Heredia D J, Smith T K. Critical role of 5-HT1A, 5-HT3, and 5-HT7 receptor subtypes in the initiation, generation, and propagation of the murine colonic migrating motor complex. Am J Physiol Gastrointest Liver Physiol 2010; 299:G144-57.
22. Hemedah M, Coupar I M, Mitchelson F J. [3H]-Mesulergine labels 5-HT7 sites in rat brain and guinea-pig ileum but not rat jejunum. Br J Pharmacol 1999; 126: 179-88.
23. Kim J J, Bridle B W, Ghia J E, et al. Targeted inhibition of serotonin type 7 (5-HT$_7$) receptor function modulates immune responses and reduces the severity of intestinal inflammation. J Immunol 2013; 190:4795-804.
24. Yaakob N S, Chinkwo K A, Chetty N, et al. Distribution of 5-HT3, 5-HT4, and 5-HT7 Receptors Along the Human Colon. J Neurogastroenterol Motil 2015; 21:361-9.
25. Meuser T, Pietruck C, Gabriel A, et al. 5-HT7 receptors are involved in mediating 5-HT-induced activation of rat primary afferent neurons. Life Sci 2002; 71:2279-89.
26. Hansen H D, Herth M M, Ettrup A, et al. Radiosynthesis and in vivo evaluation of novel radioligands for PET imaging of cerebral 5-HT7 receptors. J Nucl Med 2014; 55:640-6.
27. Zou B C, Dong L, Wang Y, et al. Expression and role of 5-HT7 receptor in brain and intestine in rats with irritable bowel syndrome. Chin Med J (Engl) 2007; 120:2069-74.
28. Singer S M, Nash T E. T-cell-dependent control of acute *Giardia lamblia* infections in mice. Infect. Immun. 2000; 68:170-175.
29. Davids B J, Palm J E, Housley M P, et al. Polymeric immunoglobulin receptor in intestinal immune defense against the lumen-dwelling protozoan parasite *Giardia*. J Immunol 2006; 177:6281-6290.
30. Scott K G, Yu L C H, Buret A G. Role of CD8+ and CD4+ T lymphocytes in jejunal mucosal injury during murine giardiasis. Infect. Immun. 2004; 72:3536-3542.
31. Scott K G, Meddings J B, Kirk D R, et al. Intestinal infection with *Giardia* spp. reduces epithelial barrier function in a myosin light chain kinase-dependent fashion. Gastroenterology 2002; 123:1179-1190.
32. Lu C L, Hsieh J C, Dun N J, et al. Estrogen rapidly modulates 5-hydroxytrytophan-induced visceral hypersensitivity via GPR30 in rats. Gastroenterology 2009; 137:1040-1050.
33. Hong S, Zheng G, Wu X, et al. Corticosterone mediates reciprocal changes in CB 1 and TRPV1 receptors in primary sensory neurons in the chronically stressed rat. Gastroenterology 2011; 140:627-637 e4.
34. Forcen R, Latorre E, Pardo J, et al. Toll-like receptors 2 and 4 modulate the contractile response induced by serotonin in mouse ileum: analysis of the serotonin receptors involved. Neurogastroenterol Motil 2015; 27:1258-66.
35. Kuo W T, Lee T C, Yang H Y, et al. LPS receptor subunits have antagonistic roles in epithelial apoptosis and colonic carcinogenesis. Cell Death Differ 2015; 22:1590-1604.
36. Wu L L, Peng W H, Kuo W T, et al. Commensal Bacterial Endocytosis in Epithelial Cells Is Dependent on Myosin Light Chain Kinase-Activated Brush Border Fanning by Interferon-gamma. Am J Pathol 2014; 184:2260-2274.
37. Yu L C, Shih Y A, Wu L L, et al. Enteric dysbiosis promotes antibiotic-resistant bacterial infection: systemic dissemination of resistant and commensal bacteria through epithelial transcytosis. Am J Physiol Gastrointest Liver Physiol 2014; 307:G824-35.
38. Nee J, Zakari M, Lembo A J. Current and emerging drug options in the treatment of diarrhea predominant irritable bowel syndrome. Expert Opin Pharmacother 2015; 16:2781-92.
39. Dunlop S P, Hebden J, Campbell E, et al. Abnormal intestinal permeability in subgroups of diarrhea-predominant irritable bowel syndromes. Am J Gastroenterol. 2006; 101:1288-1294.
40. Dunlop S P, Jenkins D, Neal K R, et al. Relative importance of enterochromaffin cell hyperplasia, anxiety, and depression in postinfectious IBS. Gastroenterology 2003; 125:1651-1659.
41. Atkinson W, Lockhart S, Whorwell P J, et al. Altered 5-hydroxytryptamine signaling in patients with constipation- and diarrhea-predominant irritable bowel syndrome. Gastroenterology 2006; 130:34-43.
42. Qin H Y, Wu J C, Tong X D, et al. Systematic review of animal models of post-infectious/post-inflammatory irritable bowel syndrome. J Gastroenterol 2011; 46:164-74.

43. Li C P, Ling C, Biancani P, et al. Effect of progesterone on colonic motility and fecal output in mice with diarrhea. Neurogastroenterol Motil 2012; 24:392-e174.
44. Julio-Pieper M, O'Mahony C M, Clarke G, et al. Chronic stress-induced alterations in mouse colonic 5-HT and defecation responses are strain dependent. Stress 2012; 15:218-26.
45. Camilleri M. Pharmacology and clinical experience with alosetron. Expert Opin Investig Drugs 2000; 9:147-59.
46. Berman S M, Chang L, Suyenobu B, et al. Condition-specific deactivation of brain regions by 5-HT3 receptor antagonist Alosetron. Gastroenterology 2002; 123:969-77.
47. Mayer E A, Berman S, Derbyshire S W, et al. The effect of the 5-HT3 receptor antagonist, alosetron, on brain responses to visceral stimulation in irritable bowel syndrome patients. Aliment Pharmacol Ther 2002; 16:1357-66.
48. Bradesi S, Lao L, McLean P G, et al. Dual role of 5-HT3 receptors in a rat model of delayed stress-induced visceral hyperalgesia. Pain 2007; 130:56-65.

What is claimed is:

1. A compound of the following general formula or a pharmaceutically acceptable salt thereof:

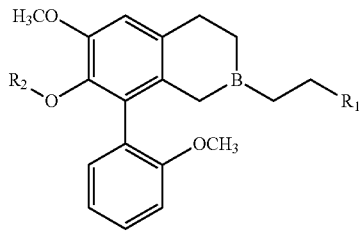

wherein $R_1$ is $CH_2$Hete and the Hete is a heteroaromatic group selected from pyridyl group, pyrrolyl group, pyrimidinyl group, imidazolyl group and thiazolyl group; and $R_2$ is a hydrogen or a methyl group.

2. The compound as claimed in claim 1, which is selected from 6 methoxy-8-(2-methoxyphenyl)-2-(3-(pyridin-4-yl)propyl)-1,2,3,4-tetrahydroisoquinolin-7-ol (compound 8), 6-methoxy-8-(2-methoxyphenyl)-2-(3-(pyridin-3-yl)propyl)-1,2,3,4-tetrahydroisoquinolin-7-ol (compound 9), and 6,7-dimethoxy-8-(2-methoxyphenyl)-2-(3-(pyridin-4-yl)propyl)-1,2,3,4-tetrahydroisoquinoline (compound 10), or a pharmaceutically acceptable salt thereof.

3. The compound as claimed in claim 1, which is 6-methoxy-8-(2-methoxyphenyl)-2-(3-(pyridin-4-yl)propyl)-1,2,3,4-tetrahydroisoquinolin-7-ol (compound 8) or a pharmaceutically acceptable salt thereof.

4. A pharmaceutical composition comprising a pharmaceutically acceptable carrier and a therapeutically effective amount of the compound as claimed in claim 1, 2, or 3 or a pharmaceutically acceptable salt thereof.

5. A method for treating irritable bowel syndrome, comprising the step of administering to a subject in need thereof an effective amount of the pharmaceutical composition as claimed in claim 4.

6. The method as claimed in claim 5, wherein the irritable bowel syndrome is treated by providing an antagonism to 5-$HT_7$ receptors.

7. The method as claimed in claim 5, wherein the irritable bowel syndrome is treated by inhibiting a pain induced by infection followed by stress.

8. The method as claimed in claim 5, wherein the irritable bowel syndrome is treated by inhibiting a pain induced by chemically induced inflammation.

* * * * *

UNITED STATES PATENT AND TRADEMARK OFFICE
CERTIFICATE OF CORRECTION

PATENT NO. : 11,505,529 B2
APPLICATION NO. : 16/490070
DATED : November 22, 2022
INVENTOR(S) : Ling-Wei Hsin, Linda Chia-Hui Yu and Tsung-Chun Lee It is certified that error appears in the above-identified patent and that said Letters Patent is hereby corrected as shown below:

In the Claims

Column 51, Claim 1, Line 29, delete "B" from the general formula and insert --N--.

Signed and Sealed this
Fifth Day of September, 2023

Katherine Kelly Vidal
*Director of the United States Patent and Trademark Office*